(12) United States Patent
Högberg et al.

(10) Patent No.: US 9,006,241 B2
(45) Date of Patent: *Apr. 14, 2015

(54) PYRIMIDINE DERIVATIVES

(75) Inventors: Marita Högberg, Huddinge (SE);
Emma Dahlstedt, Huddinge (SE); Olof Smitt, Huddinge (SE); Tommy Johansson, Huddinge (SE)

(73) Assignee: Noviga Research AB, Tullinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/005,889

(22) PCT Filed: Mar. 23, 2012

(86) PCT No.: PCT/EP2012/055216
§ 371 (c)(1),
(2), (4) Date: Oct. 29, 2013

(87) PCT Pub. No.: WO2012/127032
PCT Pub. Date: Sep. 27, 2012

(65) Prior Publication Data
US 2014/0045845 A1    Feb. 13, 2014

(30) Foreign Application Priority Data
Mar. 24, 2011  (EP) ..................................... 11159589
Nov. 17, 2011  (EP) ..................................... 11189572

(51) Int. Cl.
C07D 401/14    (2006.01)
C07D 403/14    (2006.01)

(52) U.S. Cl.
CPC ..................................... C07D 403/14 (2013.01)

(58) Field of Classification Search
None
See application file for complete search history.

(56) References Cited

U.S. PATENT DOCUMENTS

| | | | |
|---|---|---|---|
| 5,412,091 A | 5/1995 | Boivin et al. | |
| 5,455,348 A | 10/1995 | Austel et al. | |
| 5,491,234 A | 2/1996 | Coe et al. | |
| 5,616,743 A | 4/1997 | Boivin et al. | |
| 6,596,746 B1 | 7/2003 | Das et al. | |
| 6,649,608 B2 | 11/2003 | Pease et al. | |
| 6,881,737 B2 | 4/2005 | Buchanan et al. | |
| 6,897,220 B2 | 5/2005 | Delorme et al. | |
| 6,939,874 B2 | 9/2005 | Harmange et al. | |
| 6,979,694 B2 | 12/2005 | Das et al. | |
| 7,060,827 B2 | 6/2006 | Singh et al. | |
| 7,091,233 B2 | 8/2006 | Fischer et al. | |
| 7,109,335 B2 | 9/2006 | Kath et al. | |
| 7,109,337 B2 | 9/2006 | Kath et al. | |
| 7,112,587 B2 | 9/2006 | Timmer et al. | |
| 7,115,617 B2 | 10/2006 | Buchanan et al. | |
| 7,122,542 B2 | 10/2006 | Singh et al. | |
| 7,125,875 B2 | 10/2006 | Das et al. | |
| 7,132,423 B2 | 11/2006 | Timmer et al. | |
| 7,153,856 B2 | 12/2006 | Barrish et al. | |
| 7,163,943 B2 | 1/2007 | Timmer et al. | |
| 7,169,784 B2 | 1/2007 | Timmer et al. | |
| 7,169,785 B2 | 1/2007 | Timmer et al. | |
| 7,173,032 B2 | 2/2007 | Timmer et al. | |
| 7,189,854 B2 | 3/2007 | Das et al. | |
| 7,235,561 B2 | 6/2007 | Brumby et al. | |
| 7,235,562 B2 | 6/2007 | Kath et al. | |
| 7,238,692 B2 | 7/2007 | Timmer et al. | |
| 7,265,114 B2 | 9/2007 | Timmer et al. | |
| 7,268,134 B2 | 9/2007 | Timmer et al. | |
| 7,291,624 B2 | 11/2007 | Brumby et al. | |
| 7,329,671 B2 | 2/2008 | Singh et al. | |
| 7,329,672 B2 | 2/2008 | Singh et al. | |
| 7,332,484 B2 | 2/2008 | Singh et al. | |
| 7,332,488 B2 | 2/2008 | Timmer et al. | |
| 7,332,489 B2 | 2/2008 | Timmer et al. | |

(Continued)

FOREIGN PATENT DOCUMENTS

AU    2006201229 B2    4/2006
AU    2006201230 B8    4/2006

(Continued)

OTHER PUBLICATIONS

International Search Report issued in PCT/EP2012/055216, mailed on Jun. 4, 2012.
Aliagas-Martin et al., "A Class of 2,4-Bisanilinopyrimidine Aurora A Inhibitors with Unusually High Selectivity against Aurora B," J. Med. Chem., vol. 52, 2009 (Published on Web Apr. 29, 2009), pp. 3300-3307.
Beattie et al., "Cyclin-Dependent Kinase 4 Inhibitors as a Treatment for Cancer. Part 1: Identification and Optimisation of Substituted 4,6-Bis Anilino Pyrimidines," Bioorganic & Medicinal Chemistry Letters, vol. 13, 2003, pp. 2955-2960.

(Continued)

Primary Examiner — Soren Harward
Assistant Examiner — Jeanmarie Calvillo
(74) Attorney, Agent, or Firm — Birch, Stewart, Kolasch & Birch, LLP

(57) ABSTRACT

The invention provides novel pyrimidine derivatives of formula (I), methods of preparing such compounds, pharmaceutical compositions containing such compounds, and methods for using such compounds in treatment of diseases including cancer; wherein $R^1$-$R^{11}$, Z, and Y are as defined in the specification.

45 Claims, No Drawings

(56) References Cited

U.S. PATENT DOCUMENTS

| | | |
|---|---|---|
| 7,332,490 B2 | 2/2008 | Timmer et al. |
| 7,335,656 B2 | 2/2008 | Timmer et al. |
| 7,351,712 B2 | 4/2008 | Kath et al. |
| 7,435,814 B2 | 10/2008 | Singh et al. |
| 7,449,465 B2 | 11/2008 | Freyne et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,501,424 B2 | 3/2009 | Kim et al. |
| 7,504,410 B2 | 3/2009 | Bryant et al. |
| 7,511,137 B2 | 3/2009 | Li |
| 7,514,445 B2 | 4/2009 | Freyne et al. |
| 7,517,886 B2 | 4/2009 | Singh et al. |
| 7,521,453 B2 | 4/2009 | Barlaam et al. |
| 7,521,457 B2 | 4/2009 | Stadtmueller et al. |
| 7,528,143 B2 | 5/2009 | Noronha et al. |
| 7,550,460 B2 | 6/2009 | Singh et al. |
| 7,557,210 B2 | 7/2009 | Singh et al. |
| 7,560,458 B2 | 7/2009 | Freyne et al. |
| 7,560,464 B2 | 7/2009 | Wang et al. |
| 7,560,466 B2 | 7/2009 | Singh et al. |
| 7,582,648 B2 | 9/2009 | Singh et al. |
| 7,589,200 B2 | 9/2009 | Singh et al. |
| 7,595,343 B2 | 9/2009 | Delorme et al. |
| 7,598,260 B2 | 10/2009 | Brumby et al. |
| 7,642,351 B2 | 1/2010 | Singh et al. |
| 7,655,797 B2 | 2/2010 | Singh et al. |
| 7,674,796 B2 | 3/2010 | Kath et al. |
| 7,683,061 B2 | 3/2010 | Penney et al. |
| 7,718,653 B2 | 5/2010 | Barlaam et al. |
| 7,741,336 B2 | 6/2010 | Kath et al. |
| 7,754,714 B2 | 7/2010 | Li et al. |
| 7,767,806 B2 | 8/2010 | Hirakura et al. |
| 7,803,939 B2 | 9/2010 | Singh et al. |
| 7,812,029 B1 | 10/2010 | Singh et al. |
| 7,820,648 B2 | 10/2010 | Bhattacharya et al. |
| 7,820,819 B2 | 10/2010 | Singh et al. |
| 7,825,116 B2 | 11/2010 | Singh et al. |
| 7,825,246 B2 | 11/2010 | Noronha et al. |
| 7,834,024 B2 | 11/2010 | Li et al. |
| 7,838,520 B2 | 11/2010 | Delorme et al. |
| 7,858,633 B2 | 12/2010 | Li et al. |
| 7,858,782 B2 | 12/2010 | Tao et al. |
| 7,863,286 B2 | 1/2011 | Argade et al. |
| 7,868,013 B2 | 1/2011 | Li et al. |
| 7,868,204 B2 | 1/2011 | Delorme et al. |
| 7,884,111 B2 | 2/2011 | Argade et al. |
| 7,893,074 B2 | 2/2011 | Garcia-Echeverria et al. |
| 7,906,644 B2 | 3/2011 | Singh et al. |
| 7,915,273 B2 | 3/2011 | Argade et al. |
| 7,928,109 B2 | 4/2011 | Luzzio et al. |
| 7,943,628 B2 | 5/2011 | Bell et al. |
| 7,947,698 B2 | 5/2011 | Atuegbu et al. |
| 7,956,185 B2 | 6/2011 | Diebold et al. |
| 7,962,290 B1 | 6/2011 | Qu |
| 7,964,592 B2 | 6/2011 | Garcia-Echeverria et al. |
| 7,968,556 B2 | 6/2011 | Mortensen et al. |
| 7,971,443 B2 | 7/2011 | Nishita et al. |
| 7,982,036 B2 | 7/2011 | Singh et al. |
| 7,989,465 B2 | 8/2011 | Singh et al. |
| 8,030,483 B2 | 10/2011 | Argade et al. |
| 8,039,479 B2 | 10/2011 | Michellys et al. |
| 8,044,054 B2 | 10/2011 | Argade et al. |
| 8,101,627 B2 | 1/2012 | Argade et al. |
| 8,114,882 B2 | 2/2012 | Heinrich et al. |
| 8,133,900 B2 | 3/2012 | Hood et al. |
| 8,138,199 B2 | 3/2012 | Noronha et al. |
| 8,143,391 B2 | 3/2012 | Yasugi et al. |
| 8,148,388 B2 | 4/2012 | Freyne et al. |
| 8,148,525 B2 | 4/2012 | Singh et al. |
| 8,158,621 B2 | 4/2012 | Singh et al. |
| 8,178,671 B2 | 5/2012 | Singh et al. |
| 8,188,276 B2 | 5/2012 | Singh et al. |
| 8,211,929 B2 | 7/2012 | Chen et al. |
| 8,222,256 B2 | 7/2012 | Zhang |
| 8,227,455 B2 | 7/2012 | Masuda et al. |
| 8,246,984 B2 | 8/2012 | Parmar |
| 8,247,411 B2 | 8/2012 | Luzzio et al. |
| 8,263,590 B2 | 9/2012 | Garcia-Echeverria et al. |
| 8,268,816 B2 | 9/2012 | Gupta et al. |
| 8,299,087 B2 | 10/2012 | Li et al. |
| 8,304,422 B2 | 11/2012 | Atuegbu et al. |
| 8,304,557 B2 | 11/2012 | Oguro et al. |
| 8,329,901 B2 | 12/2012 | Singh et al. |
| 8,334,296 B2 | 12/2012 | Singh et al. |
| 8,338,439 B2 | 12/2012 | Singh et al. |
| 8,344,135 B2 | 1/2013 | Hirose et al. |
| 8,349,859 B2 | 1/2013 | Su et al. |
| 8,354,407 B2 | 1/2013 | Djung et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055068 A1 | 3/2003 | Bebbington et al. |
| 2003/0064981 A1 | 4/2003 | Knegtel et al. |
| 2003/0069238 A1 | 4/2003 | Barrish et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0105090 A1 | 6/2003 | Bebbington et al. |
| 2003/0125346 A1 | 7/2003 | Buchanan et al. |
| 2003/0139416 A1 | 7/2003 | Buchanan et al. |
| 2003/0149266 A1 | 8/2003 | Pease et al. |
| 2003/0171359 A1 | 9/2003 | Dahmann et al. |
| 2003/0225073 A1 | 12/2003 | Bebbington et al. |
| 2004/0002496 A1 | 1/2004 | Bebbington et al. |
| 2004/0002507 A1 | 1/2004 | Nagarathnam et al. |
| 2004/0024208 A1 | 2/2004 | Das et al. |
| 2004/0029902 A1 | 2/2004 | Singh et al. |
| 2004/0054186 A1 | 3/2004 | Das et al. |
| 2004/0063705 A1 | 4/2004 | Harmange et al. |
| 2004/0072760 A1 | 4/2004 | Carboni et al. |
| 2004/0073026 A1 | 4/2004 | Das et al. |
| 2004/0077648 A1 | 4/2004 | Timmer et al. |
| 2004/0077875 A1 | 4/2004 | Das et al. |
| 2004/0097501 A1 | 5/2004 | Bebbington et al. |
| 2004/0102630 A1 | 5/2004 | Brumby et al. |
| 2004/0106599 A1 | 6/2004 | Delorme et al. |
| 2004/0106605 A1 | 6/2004 | Carboni et al. |
| 2004/0142953 A1 | 7/2004 | Delorme et al. |
| 2004/0186118 A1 | 9/2004 | Bryant et al. |
| 2004/0209930 A1 | 10/2004 | Carboni et al. |
| 2004/0214814 A1 | 10/2004 | Bebbington et al. |
| 2004/0220177 A1 | 11/2004 | Kath et al. |
| 2004/0224950 A1 | 11/2004 | Timmer et al. |
| 2004/0224966 A1 | 11/2004 | Brumby et al. |
| 2005/0004110 A1 | 1/2005 | Bebbington et al. |
| 2005/0004125 A1 | 1/2005 | Freyne et al. |
| 2005/0009853 A1 | 1/2005 | Kath et al. |
| 2005/0038023 A1 | 2/2005 | Bebbington et al. |
| 2005/0038243 A1 | 2/2005 | Singh et al. |
| 2005/0054638 A1 | 3/2005 | Barlaam et al. |
| 2005/0090493 A1 | 4/2005 | Breault et al. |
| 2005/0092224 A1 | 5/2005 | Kochi et al. |
| 2005/0107399 A1 | 5/2005 | Boman et al. |
| 2005/0113341 A1 | 5/2005 | Timmer et al. |
| 2005/0113398 A1 | 5/2005 | Argade et al. |
| 2005/0124619 A1 | 6/2005 | Timmer et al. |
| 2005/0137196 A1 | 6/2005 | Timmer et al. |
| 2005/0192301 A1 | 9/2005 | Li |
| 2005/0209230 A1 | 9/2005 | Singh et al. |
| 2005/0234049 A1 | 10/2005 | Singh et al. |
| 2005/0234083 A1 | 10/2005 | Chamberlain et al. |
| 2005/0245518 A1 | 11/2005 | Delorme et al. |
| 2005/0256111 A1 | 11/2005 | Kath et al. |
| 2005/0256145 A1 | 11/2005 | Kath et al. |
| 2005/0261305 A1 | 11/2005 | Das et al. |
| 2005/0267089 A1 | 12/2005 | Wang et al. |
| 2005/0288282 A1 | 12/2005 | Delorme et al. |
| 2005/0288303 A1 | 12/2005 | Barrish et al. |
| 2006/0025410 A1 | 2/2006 | Singh et al. |
| 2006/0030598 A1 | 2/2006 | Barrish et al. |
| 2006/0035891 A1 | 2/2006 | Li et al. |

(56) References Cited

U.S. PATENT DOCUMENTS

| | | |
|---|---|---|
| 2006/0035916 A1 | 2/2006 | Singh et al. |
| 2006/0051406 A1 | 3/2006 | Parmar |
| 2006/0058292 A1 | 3/2006 | Singh et al. |
| 2006/0058298 A1 | 3/2006 | Delorme et al. |
| 2006/0058525 A1 | 3/2006 | Singh et al. |
| 2006/0063789 A1 | 3/2006 | Freyne et al. |
| 2006/0079563 A1 | 4/2006 | Das et al. |
| 2006/0135543 A1 | 6/2006 | Singh et al. |
| 2006/0148800 A1 | 7/2006 | Stadtmueller et al. |
| 2006/0167249 A1 | 7/2006 | Argade et al. |
| 2006/0172984 A1 | 8/2006 | Timmer et al. |
| 2006/0183747 A1 | 8/2006 | Freyne et al. |
| 2006/0205721 A1 | 9/2006 | Freyne et al. |
| 2006/0205945 A1 | 9/2006 | Kath et al. |
| 2006/0247241 A1 | 11/2006 | Garcia-Echeverria et al. |
| 2006/0258641 A1 | 11/2006 | Timmer et al. |
| 2006/0276459 A1 | 12/2006 | Masuda et al. |
| 2006/0281774 A1 | 12/2006 | Kath et al. |
| 2006/0293311 A1 | 12/2006 | Li et al. |
| 2007/0004729 A1 | 1/2007 | Timmer et al. |
| 2007/0010668 A1 | 1/2007 | Davis-Ward et al. |
| 2007/0021443 A1 | 1/2007 | Ohlmeyer et al. |
| 2007/0031161 A1 | 2/2007 | Iandoli et al. |
| 2007/0031503 A1 | 2/2007 | Hirakura et al. |
| 2007/0043051 A1 | 2/2007 | Timmer et al. |
| 2007/0060603 A1 | 3/2007 | Singh et al. |
| 2007/0099874 A1 | 5/2007 | Timmer et al. |
| 2007/0105839 A1 | 5/2007 | Imbach et al. |
| 2007/0117795 A1 | 5/2007 | Timmer et al. |
| 2007/0122444 A1 | 5/2007 | Timmer et al. |
| 2007/0134334 A1 | 6/2007 | Hahn et al. |
| 2007/0141684 A1 | 6/2007 | Evans et al. |
| 2007/0149528 A1 | 6/2007 | Penney et al. |
| 2007/0167439 A1 | 7/2007 | Singh et al. |
| 2007/0179140 A1 | 8/2007 | Argade et al. |
| 2007/0185075 A1 | 8/2007 | Bell et al. |
| 2007/0191405 A1 | 8/2007 | Noronha et al. |
| 2007/0203161 A1 | 8/2007 | Argade et al. |
| 2007/0203162 A1 | 8/2007 | Li et al. |
| 2007/0225321 A1 | 9/2007 | Singh et al. |
| 2007/0225495 A1 | 9/2007 | Singh et al. |
| 2007/0259904 A1 | 11/2007 | Noronha et al. |
| 2007/0270427 A1 | 11/2007 | Boloor et al. |
| 2007/0270444 A1 | 11/2007 | Bebbington et al. |
| 2007/0293494 A1 | 12/2007 | Djung et al. |
| 2007/0293520 A1 | 12/2007 | Singh et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299060 A1 | 12/2007 | Li et al. |
| 2007/0299095 A1 | 12/2007 | Singh et al. |
| 2008/0004302 A1 | 1/2008 | Theoclitou et al. |
| 2008/0009484 A1 | 1/2008 | Argade et al. |
| 2008/0009494 A1 | 1/2008 | Li et al. |
| 2008/0015192 A1 | 1/2008 | Diebold et al. |
| 2008/0021020 A1 | 1/2008 | Argade et al. |
| 2008/0027045 A1 | 1/2008 | Argade et al. |
| 2008/0039447 A1 | 2/2008 | Brumby et al. |
| 2008/0039622 A1 | 2/2008 | Singh et al. |
| 2008/0051404 A1 | 2/2008 | Claiborne et al. |
| 2008/0051412 A1 | 2/2008 | Argade et al. |
| 2008/0082567 A1 | 4/2008 | Bezanson |
| 2008/0096899 A1 | 4/2008 | Kim et al. |
| 2008/0096901 A1 | 4/2008 | Arnost et al. |
| 2008/0119496 A1 | 5/2008 | Ohlmeyer et al. |
| 2008/0132504 A1 | 6/2008 | Garcia-Echeverria et al. |
| 2008/0167330 A1 | 7/2008 | Luecking et al. |
| 2008/0176853 A1 | 7/2008 | Tao et al. |
| 2008/0176866 A1 | 7/2008 | Jautelat et al. |
| 2008/0176881 A1 | 7/2008 | Michellys et al. |
| 2008/0182840 A1 | 7/2008 | Kath et al. |
| 2008/0194605 A1 | 8/2008 | Heinrich et al. |
| 2008/0214558 A1 | 9/2008 | Vankayalapati et al. |
| 2008/0221089 A1 | 9/2008 | Argade et al. |
| 2008/0234303 A1 | 9/2008 | Bhattacharya et al. |
| 2008/0249079 A1 | 10/2008 | Chen et al. |
| 2008/0255172 A1 | 10/2008 | Su et al. |
| 2008/0260754 A1 | 10/2008 | Li et al. |
| 2008/0269170 A1 | 10/2008 | Bosch et al. |
| 2008/0279867 A1 | 11/2008 | Atuegbu et al. |
| 2008/0287468 A1 | 11/2008 | Ohlmeyer et al. |
| 2008/0298830 A1 | 12/2008 | Kamisuwa et al. |
| 2008/0312438 A1 | 12/2008 | Singh et al. |
| 2009/0012045 A1 | 1/2009 | Hitoshi et al. |
| 2009/0023719 A1 | 1/2009 | Barlaam et al. |
| 2009/0023738 A1 | 1/2009 | Braeuer et al. |
| 2009/0036471 A1 | 2/2009 | Edgard et al. |
| 2009/0041786 A1 | 2/2009 | Li et al. |
| 2009/0042890 A1 | 2/2009 | Mortensen et al. |
| 2009/0054395 A1 | 2/2009 | Luzzio et al. |
| 2009/0118310 A1 | 5/2009 | Nur-E-Kamal et al. |
| 2009/0124645 A1 | 5/2009 | Sorensen et al. |
| 2009/0131463 A1 | 5/2009 | Barlaam et al. |
| 2009/0137588 A1 | 5/2009 | Singh et al. |
| 2009/0137589 A1 | 5/2009 | Argade et al. |
| 2009/0142832 A1 | 6/2009 | Dalton et al. |
| 2009/0148534 A1 | 6/2009 | Yasugi et al. |
| 2009/0149438 A1 | 6/2009 | Stadtmueller et al. |
| 2009/0156622 A1 | 6/2009 | Singh et al. |
| 2009/0156662 A1 | 6/2009 | Nozawa et al. |
| 2009/0163465 A1 | 6/2009 | Stadtmueller et al. |
| 2009/0163488 A1 | 6/2009 | Oguro et al. |
| 2009/0171085 A1 | 7/2009 | Singh et al. |
| 2009/0171086 A1 | 7/2009 | Singh et al. |
| 2009/0176981 A1 | 7/2009 | Argade et al. |
| 2009/0193826 A1 | 8/2009 | Yasugi et al. |
| 2009/0227586 A1 | 9/2009 | Djung et al. |
| 2009/0232838 A1 | 9/2009 | Dong et al. |
| 2009/0275582 A1 | 11/2009 | Noronha et al. |
| 2009/0281073 A1 | 11/2009 | Bhattacharya et al. |
| 2009/0286789 A1 | 11/2009 | Hood et al. |
| 2009/0291129 A1 | 11/2009 | Parmar |
| 2009/0298830 A1 | 12/2009 | Mann et al. |
| 2009/0299093 A1 | 12/2009 | Evans et al. |
| 2009/0306067 A1 | 12/2009 | Engelhardt et al. |
| 2009/0318687 A1 | 12/2009 | Singh et al. |
| 2010/0016296 A1 | 1/2010 | Singh et al. |
| 2010/0029610 A1 | 2/2010 | Singh et al. |
| 2010/0056503 A1 | 3/2010 | Gupta et al. |
| 2010/0093668 A1 | 4/2010 | Babin et al. |
| 2010/0125069 A1 | 5/2010 | Singh et al. |
| 2010/0144732 A1 | 6/2010 | Krueger et al. |
| 2010/0152218 A1 | 6/2010 | Argade et al. |
| 2010/0160310 A1 | 6/2010 | Freyne et al. |
| 2010/0197918 A1 | 8/2010 | Singh et al. |
| 2010/0249092 A1 | 9/2010 | Singh et al. |
| 2010/0298295 A1 | 11/2010 | Marsilje et al. |
| 2010/0298314 A1 | 11/2010 | Reddy et al. |
| 2010/0305099 A1 | 12/2010 | Sapountzis et al. |
| 2011/0027856 A1 | 2/2011 | Li et al. |
| 2011/0046108 A1 | 2/2011 | Kettle et al. |
| 2011/0046121 A1 | 2/2011 | Liang et al. |
| 2011/0046126 A1 | 2/2011 | Masuda et al. |
| 2011/0082146 A1 | 4/2011 | Atuegbu et al. |
| 2011/0086842 A1 | 4/2011 | Stadtmueller et al. |
| 2011/0098280 A1 | 4/2011 | Garcia-Echeverria et al. |
| 2011/0098288 A1 | 4/2011 | Major et al. |
| 2011/0112063 A1 | 5/2011 | Marsilje et al. |
| 2011/0112096 A1 | 5/2011 | Marsilje et al. |
| 2011/0144330 A1 | 6/2011 | Singh et al. |
| 2011/0150763 A1 | 6/2011 | Tao et al. |
| 2011/0152518 A1 | 6/2011 | Li et al. |
| 2011/0166120 A1 | 7/2011 | Luzzio et al. |
| 2011/0166139 A1 | 7/2011 | Barlaam et al. |
| 2011/0190259 A1 | 8/2011 | Michellys et al. |
| 2011/0190271 A1 | 8/2011 | Argade et al. |
| 2011/0201606 A1 | 8/2011 | Garcia-Echeverria et al. |
| 2011/0203768 A1 | 8/2011 | Nishita et al. |
| 2011/0212077 A1 | 9/2011 | Noronha et al. |
| 2011/0224217 A1 | 9/2011 | Mortensen et al. |
| 2011/0224432 A1 | 9/2011 | Singh et al. |
| 2011/0230494 A1 | 9/2011 | Singh et al. |
| 2011/0257155 A1 | 10/2011 | Michellys et al. |

(56) References Cited

U.S. PATENT DOCUMENTS

| | | | |
|---|---|---|---|
| 2011/0312908 A1 | 12/2011 | Gray et al. | |
| 2012/0045454 A1 | 2/2012 | Singh et al. | |
| 2012/0065395 A1 | 3/2012 | Freyne et al. | |
| 2012/0095011 A1 | 4/2012 | Barlaam et al. | |
| 2012/0183567 A1 | 7/2012 | Yasugi et al. | |
| 2012/0245127 A1 | 9/2012 | Masuda et al. | |
| 2012/0249119 A1 | 10/2012 | Wada et al. | |
| 2012/0253039 A1 | 10/2012 | Singh et al. | |
| 2013/0005748 A1 | 1/2013 | Michellys et al. | |
| 2013/0005964 A1 | 1/2013 | Luzzio et al. | |
| 2013/0089518 A1* | 4/2013 | Hogberg et al. | 413/14 |

FOREIGN PATENT DOCUMENTS

| | | | | |
|---|---|---|---|---|
| AU | 2006201262 B2 | 4/2006 | | |
| AU | 2006201263 B2 | 4/2006 | | |
| AU | 2006201264 A1 | 4/2006 | | |
| AU | 2006201265 B2 | 4/2006 | | |
| AU | 2006252047 B2 | 1/2007 | | |
| CN | 101289444 A | 10/2008 | | |
| CN | 101684098 A | 3/2010 | | |
| EP | 1 506 960 A1 | 2/2005 | | |
| EP | 1522540 A1 | 4/2005 | | |
| FR | 2919869 A1 | 2/2009 | | |
| WO | WO 03/026666 A1 | 4/2003 | | |
| WO | WO 03/040141 A1 | 5/2003 | | |
| WO | WO 2004/041164 A2 | 5/2004 | | |
| WO | WO 2004/046118 A2 | 6/2004 | | |
| WO | WO 2005/103996 A2 | 11/2005 | | |
| WO | WO 2006/124874 A2 | 11/2006 | | |
| WO | WO 2007-071455 A1 | 6/2007 | | |
| WO | WO 2007/121662 A1 | 11/2007 | | |
| WO | WO 2008/124085 A2 | 10/2008 | | |
| WO | WO 2009/017838 A2 | 2/2009 | | |
| WO | WO 2009/071535 A1 | 6/2009 | | |
| WO | WO 2011/120025 A1 | 9/2011 | | |
| WO | WO 2011/120026 A1 | 9/2011 | | |
| WO | WO 2014016191 A1 * | 1/2014 | | A61K 31/497 |

OTHER PUBLICATIONS

Breault et al., "Cyclin-Dependent Kinase 4 Inhibitors as a Treatment for Cancer. Part 2: Identification and Optimisation of Substituted 2,4-Bis Anilino Pyrimidines," Bioorganic & Medicinal Chemistry Letters, vol. 13, 2003, pp. 2961-2966.
Brugel et al., "Corrigendum to 'Development of N-2,4-pyrimidine-N-phenyl-N'-phenyl ureas as inhibitors of tumor necrosis factor alpha (TNF-α) synthesis. Part 1,'" Bioorganic & Medicinal Chemistry Letters, vol. 16, No. 17, 2006 (Available online Jun. 27, 2006), p. 4700.
Brugel et al., "Development of N-2,4-pyrimidine-N-phenyl-N'-phenyl ureas as inhibitors of tumor necrosis factor alpha (TNF-α) synthesis. Part 1," Bioorganic & Medicinal Chemistry Letters, vol. 16, No. 13, 2006 (Available online May 2, 2006), pp. 3510-3513.
Chemical Abstracts Service, RN 1028311-39-8, CA Index Name: "1H-Benzimidazole-4,7-diamine, N4-[4-[[(4-iodophenyl)methyl]amino]-2-pyrimidinyl]-1-(1-methylethyl)-," entered STN Jun. 15, 2008.

Dev et al., "Antitumour efficacy of VEGFR2 tyrosine kinase inhibitor correlates with expression of VEGF and its receptor VEGFR2 in tumour models," British Journal of Cancer, vol. 91, 2004 (Published online Aug. 24, 2004), pp. 1391-1398.
Elderfield et al., "Synthesis of Potential Anticancer Agent. IV. Synthesis of Certain Substituted Amino- and Aziridinopyrimidines," Journal of Organic Chemistry, vol. 25, Sep. 1960, pp. 1583-1590.
Feldman et al., "Novel Small Molecule Inhibitors of 3-Phosphoinositide-dependent Kinase-1," The Journal of Biological Chemistry, vol. 280, No. 20, May 20, 2005, pp. 19867-19874.
Ghoneim et al., "Synthesis of Some Mannich Bases of 2-,4-Amino- and 2,4-Diamino-6-Methylpyrimidines as Potential Biodynamic Agents," Egypt. J. Chem., vol. 30, No. 4, 1987, pp. 295-304.
Gossage et al., "Targeting Multiple Kinase Pathways: A Change in Paradigm," Clin. Cancer Res., vol. 16, No. 7, 2010 (Published online first Mar. 9, 2010), pp. 1973-1978.
Gunther et al., "Alternative Inhibition of Androgen Receptor Signaling: Peptidomimetic Pyrimidines As Direct Androgen Receptor/Coactivator Disruptors," ASC Chemical Biology, vol. 4, No. 6, 2009 (Published online May 14, 2009), pp. 435-440.
Harris et al., "Discovery of 5-[[4-[(2,3-Dimethyl-2H-indazol-6-yl)methylamino]-2-pyrimidinyl]amino]-2-methyl-benzenesulfonamide (Pazopanib), a Novel and Potent Vascular Endothelial Growth Factor Receptor Inhibitor," J. Med. Chem., vol. 51, 2008 (Published on Web Jul. 12, 2008), pp. 4632-4640.
International Preliminary Report on Patentability and Written Opinion of the International Searching Authority (Forms PCT/IB/373, PCT/ISA/237) for International Application No. PCT/EP2012/055216, dated Sep. 24, 2013.
International Preliminary Report on Patentability and Written Opinion of the International Searching Authority for International Application No. PCT/EP2011/058271, issued Nov. 27, 2012.
Krasnykh et al., "Radiation Protection Action of Some New Purine and Pyramidon Derivatives," Farmakologiya i Toksikologiya (Moscow), vol. 24, 1961, pp. 572-577, including an English-language abstract.
Lafleur et al., "Structure-Based Optimization of Potent and Selective Inhibitors of the Tyrosine Kinase Erythropoietin Producing Human Hepatocellular Carcinoma Receptor B4 (EphB4)," J. Med. Chem., vol. 52, 2009 (Published on Web Sep. 29, 2009), pp. 6433-6446.
Lombardo et al., "Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor . . . ," J. Med. Chem., vol. 47, 2004 (Published on Web Dec. 7, 2004), pp. 6658-6661.
Otmar et al., "Synthesis and antiproliferative activity of 2,6-diamino-9-benzyl-9-deazapurine and related compounds," Bioorganic & Medicinal Chemistry, vol. 12, 2004 (Available online May 10, 2004), pp. 3187-3195.
Parent et al., "Blocking Estrogen Signaling After the Hormone: Pyrimidine-Core Inhibitors of Estrogen Receptor-Coactivator Binding," J. Med. Chem., vol. 51, 2008 (Published on Web Sep. 12, 2008), pp. 6512-6530.
Ugarkar et al., "Adenosine Kinase Inhibitors. 3. Synthesis, SAR, and Antiinflammatory Activity of a Series of L-Lyxofuranosyl Nucleosides," J. Med. Chem., vol. 46, 2003 (Publlished on Web Sep. 23, 2003), pp. 4750-4760.

* cited by examiner

PYRIMIDINE DERIVATIVES

FIELD OF INVENTION

This invention relates to novel pyrimidine derivatives, to methods of preparing such compounds, to pharmaceutical compositions containing such compounds, and to methods for using such compounds in treatment of diseases including cancer.

BACKGROUND OF INVENTION

Cancer is a major and often fatal disease. Accordingly, the development of new therapies for cancer is an ongoing process of outmost importance. The majority of cancers are present as solid tumours, such as lung cancer, breast cancer, and prostate cancer, while others represent haematological and lymphoid malignancies, such as leukemias and lymphomas.

One important molecular target for the cancer chemotherapy is tubulin. The targeting drugs in this therapy interrupt microtubule spindle-mediated chromosome segregation, arrest the dividing tumor cells in mitosis and subsequently induce apoptosis. Existing drugs are targeting microtubules via two different mechanisms, e.g. molecules of the taxane class (that stabilize the tubulins) and several vinca alkaloids (destabilizers). The potency, efficacy, and widespread clinical use of these agents of natural origin in a variety of cancers, e.g. breast, ovarian, prostate, lung, leukemias, and lymphomas, stand testament to the importance of tubulin and its role in cancer growth. Derivatives and analogs of these plant compounds are constantly being isolated or synthesized to find more efficacious anticancer agents. For examples of novel tubulin polymerization inhibitors, see e.g. WO 2009/070645, US 2010/0279410, Mahindroo, N. et al.; Expert Opin. Ther. Patents 2006, 16, 647-691, Carlson, R.; Expert Opin. Ther. Patents 2007, 17, 707-722 and Chen, S-M. et al.; Expert Opin. Investig. Drugs 2010, 19, 329-343.

In the clinic cancer chemotherapy is used in attempts to cure or palliate the disease. In most cases this therapy is delivered in the form of combination chemotherapy, i.e. when two or more drugs having different modes of action are used together in order to optimise the effect on the cancer cells and to minimise side effects. The results obtained with chemotherapy vary according to tumour type. Some tumours are very sensitive and the treatment has a high probability of leading to beneficial treatment results including cure of the disease. Examples of this type of tumours are acute leukemias, malignant lymphomas, testicular cancer, chorion carcinomas, and Wilms tumour. Other types of cancer chemotherapy can result in effective palliation and prolonged survival. Examples of such tumours are breast cancer, colorectal cancer, ovarian cancer, small-cell lung cancer, bladder cancer, multiple myeloma, and chronic leukemias of both the lymphatic and myeloid type. Primary drug resistant tumours which respond poorly to classical chemotherapy include malignant glioma, melanoma, prostate cancer, sarcomas, and gastrointestinal tumours other than colorectal cancers (e.g. DeVita, Hellman, and Rosenberg; Cancer: Principles & Practice of Oncology, 8th Edition ISBN: 978-0-7817-7207-5).

During the recent decade much interest has been devoted to drugs directed to specific target molecules. Molecules regulating cell proliferation and death, such as Tyrosine Kinase Receptors (RTKs) for growth factors, are among targets for this type of therapeutic approach. Two classes of compounds targeting RTKs are currently used in clinical practice: monoclonal antibodies and tyrosine kinase inhibitors. The first approved targeted therapies were trastuzumab, a monoclonal antibody against HER2, for treatment of metastatic breast cancer, and imatinib, a small tyrosine kinase inhibitor targeting BCR-Abl, in Chronic Myeloid Leukemia. Despite good treatment results many of the treated patients have developed drug resistance, often due to the activation of alternative RTKs pathways. Currently there is a general idea that molecules interfering simultaneously with multiple RTKs might be more effective than single target agents. There are a few recently approved drugs, such as sorafenib and sunitinib, that apparently target multiple pathways and could serve as representatives of this new generation of anti-cancer drugs (see e.g. Gossage, L. et al; Clin. Cancer. Res. 2010, 16, 1973-1978).

Certain pyrimidine compounds and their potential use in the treatment of e.g. cancer are disclosed in for example WO2003/030909, WO2003/059913, WO2003/063794, WO2004/056807, WO2004/056786, WO2006/133426, WO2007/085833, WO2008/128231, WO2009/063240, WO2009/071535, US2009/142832, EP1506960 and WO2007/071455.

What is needed in the art are targeted drugs that work in a specific manner, being selective in eliminating subpopulations of cells involved in tumour survival and progression. The present invention provides novel pyrimidine compounds that have a surprisingly efficient antiproliferative activity. Hence, these novel compounds are useful in the treatment of proliferative diseases, such as cancer.

DESCRIPTION OF THE INVENTION

In a first aspect of the present invention, there is provided a compound of formula I or a pharmaceutically acceptable ester, amide, solvate or salt thereof,

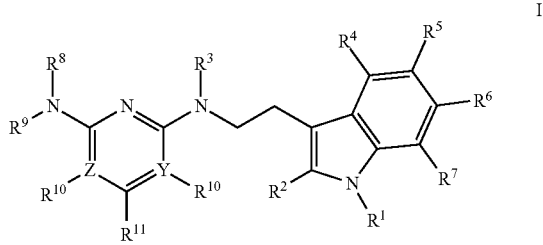

wherein
Z represents carbon or nitrogen;
Y represents carbon or nitrogen, wherein one of Z and Y represents nitrogen;
$R^1$, $R^3$, and $R^8$ are independently selected from hydrogen and $(C_1-C_4)$alkyl;
$R^2$ is selected from hydrogen, $(C_1-C_4)$alkyl, $(C_1-C_4)$alkyl-NH$(C_1-C_4)$alkyl, $(C_1-C_4)$alkyl-N[$(C_1-C_4)$alkyl]$_2$, and (CO)OH;
$R^4$, $R^5$, $R^6$, and $R^7$ are independently selected from hydrogen, halogen, hydroxy, amino, nitro, cyano, $(C_1-C_4)$alkyl, $(C_1-C_4)$alkyl-OH, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl]$_2$, $(C_1-C_4)$alkyl-NH(CO)$(C_1-C_4)$alkyl, (CO)OH, (CO)NH$_2$, (CO)NH$(C_1-C_4)$alkyl, (CO)N[$(C_1-C_4)$alkyl]$_2$, O$(C_1-C_4)$alkyl, O$(C_1-C_4)$alkyl$(C_2-C_5)$heterocyclyl, O$(C_1-C_4)$alkyl$(C_2-C_5)$heterocyclyl$(C_1-C_4)$alkyl, O$(C_1-C_4)$alkyl(CO)OH, O$(C_1-C_4)$alkyl(CO)NH$(C_1-C_4)$alkyl, O$(C_1-C_4)$alkyl(CO)N[$(C_1-C_4)$alkyl]$_2$, OCF$_3$, NH$(C_1-C_4)$alkyl, N[$(C_1-C_4)$alkyl]$_2$, NH(CO)$(C_1-C_4)$alkyl, NHSO$_2$$(C_1-C_4)$alkyl, N[(C$_1$-C$_4$)alkyl]SO$_2$(C$_1$-C$_4$)alkyl, SH, S(C$_1$-C$_4$)alkyl, SO$_2$NH$_2$, SO$_2$NH(C$_1$-C$_4$)alkyl, and SO$_2$N[(C$_1$-C$_4$)alkyl]$_2$;

R$^{10}$ is selected from hydrogen, amino, and (C$_1$-C$_4$)alkyl when Z or Y is carbon;

R$^{11}$ is selected from hydrogen, amino, (C$_1$-C$_4$)alkyl, (C$_1$-C$_4$)alkyl(C$_2$-C$_5$)heterocyclyl, (C$_1$-C$_4$)alkyl(C$_2$-C$_5$)heterocyclyl(C$_1$-C$_4$)alkyl, (CO)OH, (CO)NH$_2$, (CO)NH(C$_1$-C$_4$)alkyl, (CO)N[(C$_1$-C$_4$)alkyl]$_2$, (CO)(C$_1$-C$_4$)alkyl, (C$_2$-C$_5$)heterocyclyl, (C$_2$-C$_5$)heterocyclyl(C$_1$-C$_4$)alkyl, NH(C$_1$-C$_4$)alkyl, N[(C$_1$-C$_4$)alkyl]$_2$, NH(CO)(C$_1$-C$_4$)alkyl, NHSO$_2$(C$_1$-C$_4$)alkyl, N[(C$_1$-C$_4$)alkyl]SO$_2$(C$_1$-C$_4$)alkyl, SO$_2$NH$_2$, SO$_2$NH(C$_1$-C$_4$)alkyl, and SO$_2$N[(C$_1$-C$_4$)alkyl]$_2$;

R$^9$ represents

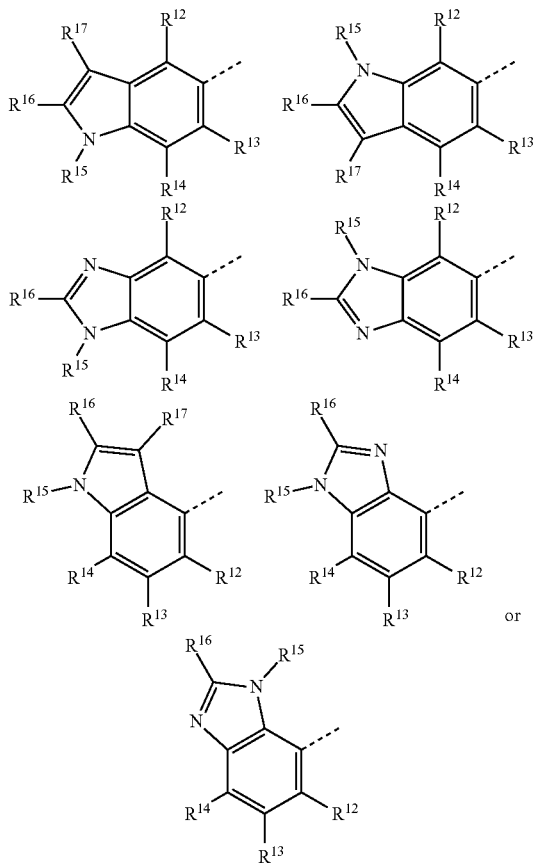

R$^{12}$, R$^{13}$, and R$^{14}$ are independently selected from hydrogen, halogen, hydroxy, (C$_1$-C$_4$)alkyl, O(C$_1$-C$_4$)alkyl, NH(C$_1$-C$_4$)alkyl, and N[(C$_1$-C$_4$)alkyl]$_2$;

R$^{15}$ is selected from hydrogen and (C$_1$-C$_4$)alkyl; and

R$^{16}$ and R$^{17}$ are independently selected from hydrogen, halogen, (C$_1$-C$_4$)alkyl, (C$_1$-C$_4$)alkyl(C$_2$-C$_5$)heterocyclyl, (C$_1$-C$_4$)alkyl(C$_2$-C$_5$)heterocyclyl(C$_1$-C$_4$)alkyl, (C$_1$-C$_4$)alkyl(CO)OH, (C$_1$-C$_4$)alkyl(CO)NH$_2$, (C$_1$-C$_4$)alkyl(CO)NH(C$_1$-C$_4$)alkyl, (C$_1$-C$_4$)alkyl(CO)N[(C$_1$-C$_4$)alkyl]$_2$, (C$_1$-C$_4$)alkyl-OH, (C$_1$-C$_4$)alkyl-O(C$_1$-C$_4$)alkyl, (C$_1$-C$_4$)alkyl-NH(C$_1$-C$_4$)alkyl, (C$_1$-C$_4$)alkyl-N[(C$_1$-C$_4$)alkyl]$_2$, (C$_1$-C$_4$)alkyl-NH(CO)(C$_1$-C$_4$)alkyl, (CO)OH, (CO)NH$_2$, (CO)NH(C$_1$-C$_4$)alkyl, (CO)N[(C$_1$-C$_4$)alkyl]$_2$, (CO)(C$_1$-C$_4$)alkyl, (CO)(C$_2$-C$_5$)heterocyclyl, and (CO)(C$_2$-C$_5$)heterocyclyl(C$_1$-C$_4$)alkyl.

In the present invention, esters are included, such as when R$^{16}$ is (CO)OH, esters thereof are also included, such as (CO)OCH$_3$ and (CO)OC$_2$H$_5$OH. Therefore, in one embodiment of this aspect, R$^{16}$ represents an ester of (CO)OH, selected from (CO)OCH$_3$ and (CO)OC$_2$H$_5$OH.

In another embodiment of this aspect, R$^1$ represents hydrogen.

In another embodiment of this aspect, R$^2$, R$^3$, and R$^8$ are independently selected from hydrogen and methyl.

In another embodiment of this aspect, R$^2$, R$^3$, and R$^8$ represent hydrogen.

In another embodiment of this aspect, Z represents carbon and Y represents nitrogen.

In another embodiment of this aspect, R$^4$, R$^5$, R$^6$, and R$^7$ are independently selected from hydrogen, halogen, hydroxy, (C$_1$-C$_4$)alkyl, O(C$_1$-C$_4$)alkyl, O(C$_1$-C$_4$)alkyl(C$_2$-C$_5$)heterocyclyl, and OCF$_3$.

In another embodiment of this aspect, R$^5$ represents O(C$_1$-C$_4$)alkyl.

In another embodiment of this aspect, R$^5$ is selected from methoxy, ethoxy, and propoxy.

In another embodiment of this aspect, R$^{10}$ is selected from hydrogen, (C$_1$-C$_4$)alkyl and NH$_2$ when Z or Y is carbon.

In another embodiment of this aspect, R$^{10}$ is selected from hydrogen and (C$_1$-C$_4$)alkyl when Z or Y is carbon.

In another embodiment of this aspect, R$^{10}$ is selected from hydrogen and methyl when Z or Y is carbon.

In another embodiment of this aspect, R$^{11}$ is selected from hydrogen, (C$_1$-C$_4$)alkyl, (CO)NH$_2$, and (C$_2$-C$_5$)heterocyclyl (C$_1$-C$_4$)alkyl.

In another embodiment of this aspect, R$^{11}$ is selected from hydrogen and methyl.

In another embodiment of this aspect, R$^9$ is selected from

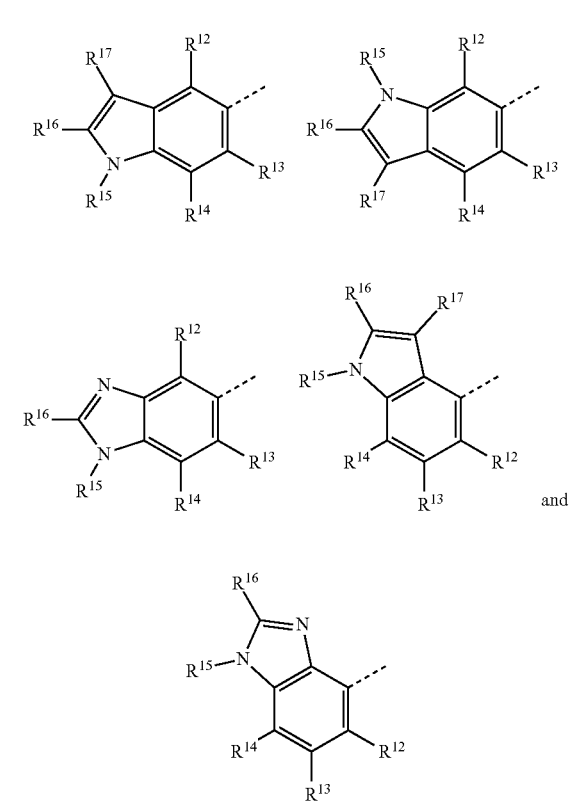

and

In another embodiment of this aspect, $R^9$ is selected from

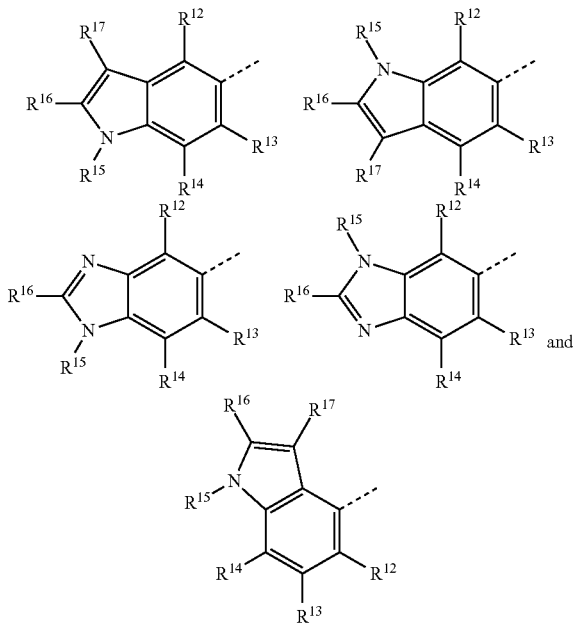

In another embodiment of this aspect, $R^{12}$, $R^{13}$, and $R^{14}$ represent hydrogen.

In another embodiment of this aspect, $R^{15}$ is selected from hydrogen and methyl.

In another embodiment of this aspect, $R^{16}$ and $R^{17}$ are independently selected from hydrogen, $(C_1-C_4)$alkyl, $(C_1-C_4)$alkyl-OH, and (CO)OH.

In another embodiment of this aspect, $R^{16}$ and $R^{17}$ are independently selected from hydrogen, methyl, $(C_1-C_4)$alkyl-OH, and (CO)OH.

In another embodiment of this aspect, $R^{16}$ and $R^{17}$ are independently selected from hydrogen, methyl, and $(C_1-C_4)$alkyl-OH.

In another embodiment of this aspect, $R^{16}$ is selected from hydrogen, methyl, $(C_1-C_4)$alkyl-OH, and (CO)OH.

In another embodiment of this aspect, when $R^{16}$ is (CO)OH, esters thereof are also included, such as (CO)OCH$_3$ and (CO)OC$_2$H$_5$OH.

In another embodiment of this aspect, $R^{16}$ is selected from hydrogen, methyl, and $(C_1-C_4)$alkyl-OH.

In another embodiment of this aspect, $R^{16}$ is selected from hydrogen, methyl and hydroxymethyl.

In another embodiment of this aspect, $R^{17}$ is selected from hydrogen and methyl.

In another embodiment of this aspect, Y represents carbon and Z represents nitrogen.

In another embodiment of this aspect,

Z represents carbon and Y represents nitrogen;

$R^1$, $R^2$, $R^3$, $R^8$, $R^{12}$, $R^{13}$, and $R^{14}$ represent hydrogen;

$R^4$, $R^5$, $R^6$, and $R^7$ are independently selected from hydrogen, halogen, hydroxy, $(C_1-C_4)$alkyl, $O(C_1-C_4)$alkyl, $O(C_1-C_4)$alkyl$(C_2-C_5)$heterocyclyl, and OCF$_3$;

$R^{10}$ is selected from hydrogen and $(C_1-C_4)$alkyl when Z or Y is carbon;

$R^{11}$ is selected from hydrogen, $(C_1-C_4)$alkyl, (CO)NH$_2$, and $(C_2-C_5)$heterocyclyl$(C_1-C_4)$alkyl;

$R^9$ is selected from

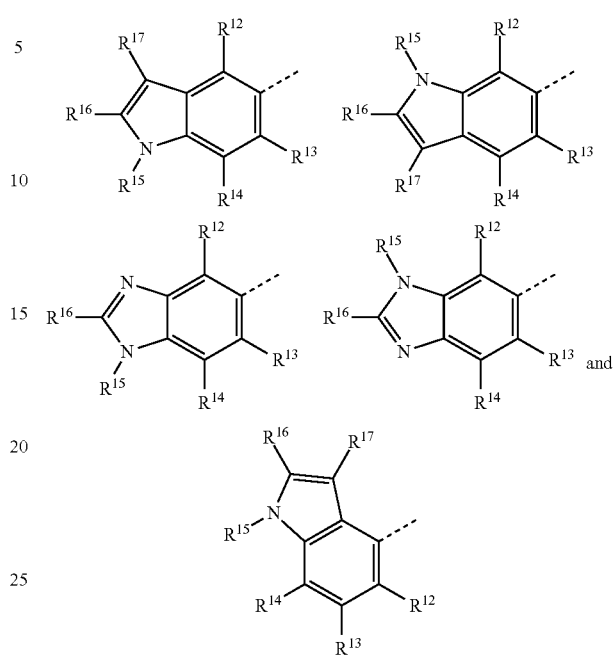

$R^{15}$ is selected from hydrogen and methyl;

and $R^{16}$ and $R^{17}$ are independently selected from hydrogen, $(C_1-C_4)$alkyl, $(C_1-C_4)$alkyl-OH, and (CO)OH. Preferably, $R^{16}$ is methyl and $R^{17}$ is selected from hydrogen and $(C_1-C_4)$alkyl.

In another embodiment of this aspect, $R^4$ represents hydrogen;

$R^5$ is selected from halogen, methyl, $O(C_1-C_2)$alkyl, and OCF$_3$;

$R^6$ and $R^7$ are independently selected from hydrogen, methyl, and methoxy;

$R^{10}$ is selected from hydrogen and methyl when Z or Y is carbon;

$R^{11}$ is selected from hydrogen, methyl, and (CO)NH$_2$;

$R^9$ is selected from

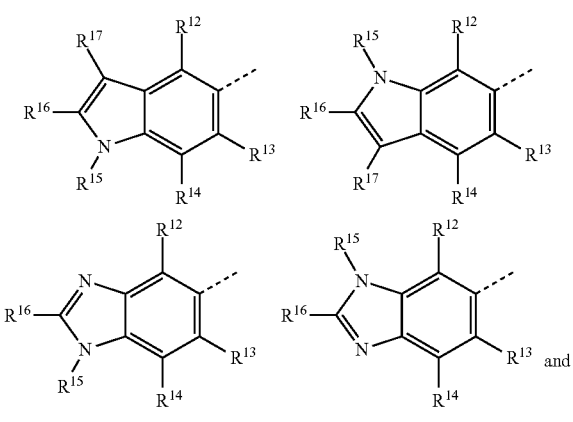

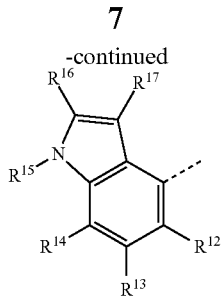

$R^{15}$ is selected from hydrogen and methyl;
and $R^{16}$ and $R^{17}$ are independently selected from hydrogen, methyl, and hydroxymethyl.

In another embodiment of this aspect, $R^{16}$ represents methyl.

In another embodiment of this aspect, $R^5$ is selected from methoxy, methyl, and fluoro.

In another embodiment of this aspect, $R^5$ is selected from methoxy and methyl.

In another embodiment of this aspect, $R^{11}$ is selected from hydrogen, methyl, and $(CO)NH_2$.

In another embodiment of this aspect, $R^9$ is selected from

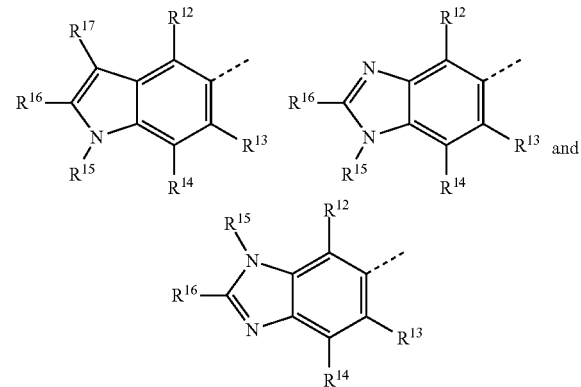

wherein $R^{15}$ and $R^{17}$ are independently selected from hydrogen and methyl; and $R^{16}$ is selected from hydrogen, methyl, hydroxymethyl, and $(CO)OH$.

In another embodiment of this aspect, there is provided a compound of formula I, wherein
Z represents carbon and Y represents nitrogen;
$R^1$, $R^{10}$, $R^{12}$, $R^{13}$, $R^{14}$, and $R^{17}$ represent hydrogen;
$R^2$, $R^3$, $R^7$, $R^8$, and $R^{11}$ are independently selected from hydrogen and methyl;
$R^4$, $R^5$, and $R^6$ are independently selected from hydrogen and $O(C_1-C_4)$alkyl;
$R^9$ is selected from

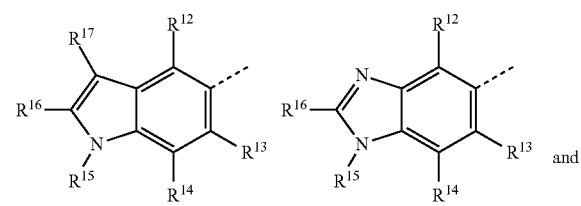

$R^{15}$ is selected from hydrogen and methyl; and
$R^{16}$ represents hydrogen, methyl, and hydroxymethyl.

In another embodiment of this aspect, there is provided a compound of formula I, wherein
Z represents carbon and Y represents nitrogen;
$R^1$, $R^2$, $R^3$, $R^4$, $R^6$, $R^7$, $R^8$, $R^{12}$, $R^{13}$, and $R^{14}$ represent hydrogen;
$R^{10}$, $R^{11}$, $R^{15}$, and $R^{17}$ are independently selected from hydrogen and methyl;
$R^5$ is selected from methoxy and ethoxy;
$R^9$ is selected from

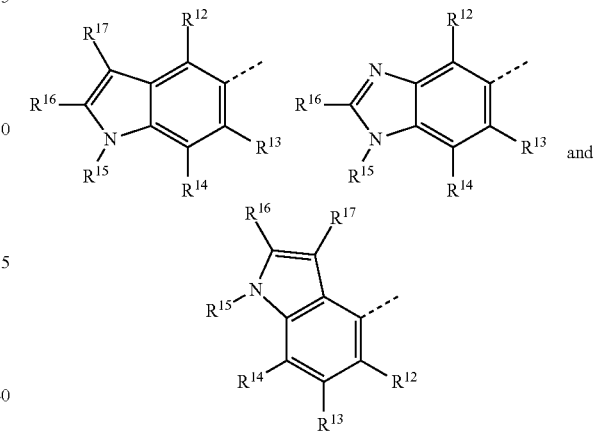

and;
$R^{16}$ is selected from hydrogen, methyl, and hydroxymethyl.

In another embodiment of this aspect, there is provided a compound of formula I, wherein
$R^1$, $R^2$, $R^3$, $R^4$, $R^6$, $R^7$, $R^8$, $R^{12}$, $R^{14}$, and $R^{17}$ represent hydrogen;
$R^{10}$ is selected from hydrogen and amino;
$R^{11}$ is selected from hydrogen, $(CO)NH_2$, and $(C_2-C_5)$heterocyclyl$(C_1-C_4)$alkyl;
$R^5$ is selected from methoxy, ethoxy, and hydroxy;
$R^{15}$ is selected from hydrogen and methyl;
$R^{16}$ is selected from hydrogen, methyl, and hydroxymethyl; and
$R^9$ is selected from

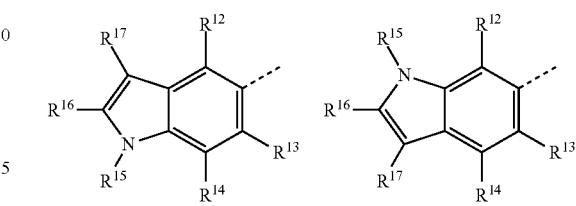

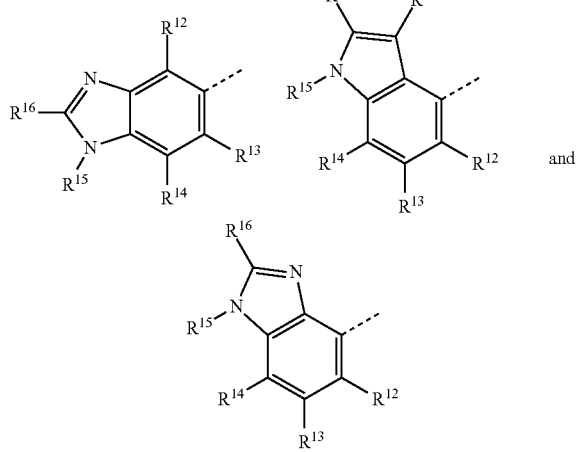

In another embodiment of this aspect, there is provided a compound of formula I, wherein
Z represents carbon or nitrogen;
Y represents carbon or nitrogen, wherein one of Z and Y represents nitrogen;
$R^1$, $R^2$, $R^3$ and $R^8$ are independently selected from hydrogen and ($C_1$-$C_4$)alkyl;
$R^4$, $R^5$, $R^6$ and $R^7$ are independently selected from hydrogen, halogen, hydroxy, ($C_1$-$C_4$)alkyl, $O(C_1$-$C_4)$alkyl, $O(C_1$-$C_4)$alkyl($C_2$-$C_5$)heterocyclyl, and $OCF_3$;
$R^9$ represents

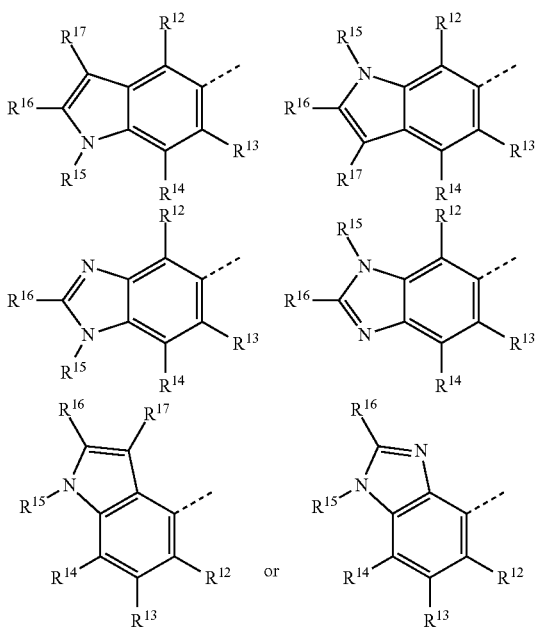

$R^{10}$ is selected from hydrogen, ($C_1$-$C_4$)alkyl and amino when Z or Y is carbon;
$R^{11}$ is selected from hydrogen, ($C_1$-$C_4$)alkyl, ($C_2$-$C_5$)heterocyclyl($C_1$-$C_4$)alkyl and $(CO)NH_2$;
$R^{12}$, $R^{13}$ and $R^{14}$ are hydrogen;
$R^{15}$ and $R^{17}$ are independently selected from hydrogen and ($C_1$-$C_4$)alkyl; and
$R^{16}$ is selected from hydrogen, ($C_1$-$C_4$)alkyl, (CO)OH, and ($C_1$-$C_4$)alkyl-OH.

In another embodiment of this aspect, there is provided a compound of formula I, wherein
Z represents carbon or nitrogen;
Y represents carbon or nitrogen, wherein one of Z and Y represents nitrogen;
$R^1$, $R^2$, $R^3$ and $R^8$ are independently selected from hydrogen and methyl;
$R^4$, $R^5$, $R^6$ and $R^7$ are independently selected from hydrogen, halogen, hydroxy, methyl, methoxy, ethoxy, propoxy, $O(C_1$-$C_4)$alkyl($C_2$-$C_5$)heterocyclyl, and $OCF_3$;
$R^9$ represents

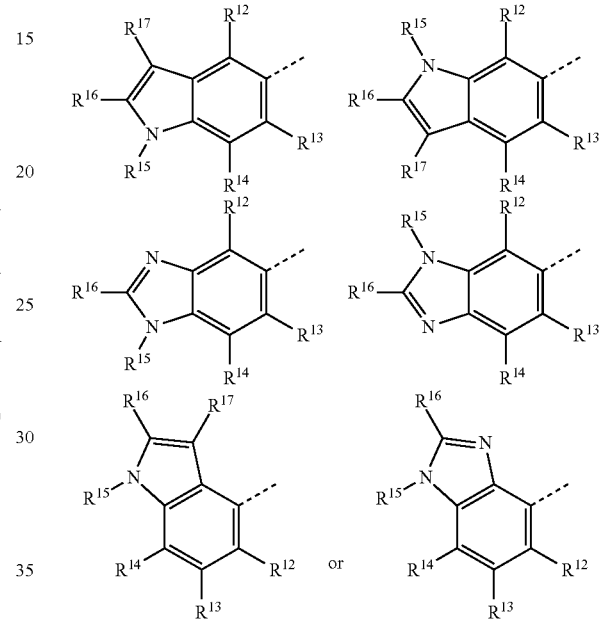

$R^{10}$ is selected from hydrogen, methyl and amino when Z or Y is carbon;
$R^{11}$ is selected from hydrogen, methyl, ($C_2$-$C_5$)heterocyclyl($C_1$-$C_4$)alkyl and $(CO)NH_2$;
$R^{12}$, $R^{13}$ and $R^{14}$ are hydrogen;
$R^{15}$ and $R^{17}$ are independently selected from hydrogen and methyl; and
$R^{16}$ is selected from hydrogen, methyl, (CO)OH, and ($C_1$-$C_4$)alkyl-OH.

In another aspect of the invention, there is provided a compound of formula I, said compound being selected from:
$N^2$-[2-(1H-indol-3-yl)ethyl]-$N^4$-(1H-indol-5-yl)pyrimidine-2,4-diamine;
$N^4$-(1H-indol-5-yl)-$N^2$-[2-(5-methoxy-1H-indol-3-yl)ethyl]pyrimidine-2,4-diamine;
$N^2$-[2-(1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(2-methyl-1H-indol-5-yl)pyrimidine-2,4-diamine;
$N^2$-[2-(5-ethoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-{2-[5-(2-morpholinoethoxy)-1H-indol-3-yl]ethyl}pyrimidine-2,4-diamine;
$N^4$-(2-methyl-1H-indol-5-yl)-$N^2$-{2-[5-(trifluoromethoxy)-1H-indol-3-yl]ethyl}pyrimidine-2,4-diamine;
3-{2-[4-(2-methyl-1H-indol-5-ylamino)pyrimidin-2-ylamino]ethyl}-1H-indol-5-ol;
$N^2$-[2-(5-methyl-1H-indol-3-yl)ethyl]-$N^4$-(2-methyl-1H-indol-5-yl)pyrimidine-2,4-diamine;

$N^2$-[2-(5-fluoro-1H-indol-3-yl)ethyl]-$N^4$-(2-methyl-1H-indol-5-yl)pyrimidine-2,4-diamine;
$N^2$-[2-(6-methoxy-1H-indol-3-yl)ethyl]-$N^4$-(2-methyl-1H-indol-5-yl)pyrimidine-2,4-diamine;
$N^2$-[2-(7-methoxy-1H-indol-3-yl)ethyl]-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]pyrimidine-2,4-diamine;
$N^4$-(2,3-dimethyl-1H-indol-5-yl)-$N^2$-[2-(5-methoxy-1H-indol-3-yl)ethyl]pyrimidine-2,4-diamine;
(5-{2-[2-(5-methoxy-1H-indol-3-yl)ethylamino]pyrimidin-4-ylamino}-1H-indol-2-yl)methanol;
methyl 5-{2-[2-(5-methoxy-1H-indol-3-yl)ethylamino]pyrimidin-4-ylamino}-1H-indole-2-carboxylate;
2-hydroxyethyl 5-{2-[2-(5-methoxy-1H-indol-3-yl)ethylamino]pyrimidin-4-ylamino}-1H-indole-2-carboxylate;
$N^4$-(1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzo[d]imidazol-5-yl)pyrimidine-2,4-diamine;
$N^4$-(1H-indol-6-yl)-$N^2$-[2-(5-methoxy-1H-indol-3-yl)ethyl]pyrimidine-2,4-diamine;
$N^4$-(1H-indol-4-yl)-$N^2$-[2-(5-methoxy-1H-indol-3-yl)ethyl]pyrimidine-2,4-diamine;
$N^4$-[2-(1H-indol-3-yl)ethyl]-$N^2$-(2-methyl-1H-indol-5-yl)pyrimidine-2,4-diamine;
$N^4$-[2-(5-methoxy-1H-indol-3-yl)ethyl]-$N^2$-(2-methyl-1H-indol-5-yl)pyrimidine-2,4-diamine;
$N^4$-[2-(1H-indol-3-yl)ethyl]-$N^2$-(1H-indol-6-yl)pyrimidine-2,4-diamine;
$N^4$-[2-(1H-indol-3-yl)ethyl]-$N^2$-(1H-indol-4-yl)pyrimidine-2,4-diamine;
$N^2$-[2-(1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-indol-5-yl)pyrimidine-2,4-diamine;
2-[2-(5-methoxy-1H-indol-3-yl)ethylamino]-6-(2-methyl-1H-indol-5-ylamino)pyrimidine-4-carboxamide;
$N^2$-[2-(5-methoxy-1H-indol-3-yl)ethyl]-5-methyl-$N^4$-(2-methyl-1H-indol-5-yl)pyrimidine-2,4-diamine; and
$N^2$-[2-(5-methoxy-1H-indol-3-yl)ethyl]-$N^4$-(2-methyl-1H-indol-5-yl)-6-(4-methylpiperazin-1-yl)pyrimidine-2,4-diamine;
and a pharmaceutically acceptable ester, amide, solvate or salt thereof.

In another aspect of the invention, there is provided a compound of formula I, said compound being selected from:
$N^2$-[2-(4-methoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-[2-(5-propoxy-1H-indol-3-yl)ethyl]pyrimidine-2,4-diamine;
$N^2$-[2-(5-isopropoxy-1H-indol-3-yl)ethyl]-$N^4$-(2-methyl-1H-indol-5-yl)pyrimidine-2,4-diamine;
$N^2$-[2-(5,6-dimethoxy-1H-indol-3-yl)ethyl]-$N^4$-(2-methyl-1H-indol-5-yl)pyrimidine-2,4-diamine;
$N^2$-[2-(5-methoxy-7-methyl-1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(1-methyl-1H-benzo[d]imidazol-5-yl)pyrimidine-2,4-diamine;
$N^4$-(1,2-dimethyl-1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(1-methyl-1H-indol-4-yl)pyrimidine-2,4-diamine;
$N^2$-[2-(5-ethoxy-1H-indol-3-yl)ethyl]-6-methyl-$N^4$-(2-methyl-1H-indol-5-yl)pyrimidine-2,4-diamine;
$N^2$-[2-(5-methoxy-2-methyl-1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-benzo[d]imidazol-5-yl)pyrimidine-2,4-diamine;
$N^2$-[2-(5-ethoxy-1H-indol-3-yl)ethyl]-6-methyl-$N^4$-(2-methyl-1H-benzo[d]imidazol-5-yl)pyrimidine-2,4-diamine;
[5-(2-{[2-(5-methoxy-1H-indol-3-yl)ethyl][methyl]amino}pyrimidin-4-ylamino)-1H-indol-2-yl]methanol;
(5-{2-[2-(5-methoxy-1H-indol-3-yl)ethylamino]pyrimidin-4-ylamino}-1-methyl-1H-benzo[d]imidazol-2-yl)methanol;
$N^2$-[2-(5-methoxy-1H-indol-3-yl)ethyl]-$N^4$-methyl-$N^4$-(2-methyl-1H-indol-5-yl)pyrimidine-2,4-diamine; and
$N^4$-(1,2-dimethyl-1H-indol-5-yl)-$N^2$-[2-(5-methoxy-1H-indol-3-yl)ethyl]-$N^4$-methylpyrimidine-2,4-diamine;
and a pharmaceutically acceptable ester, amide, solvate or salt thereof.

In another aspect of the invention, there is provided a compound of formula I, said compound being selected from:
[5-({2-[2-(5-ethoxy-1H-indol-3-yl)ethylamino]pyrimidin-4-yl}amino)-1H-indol-2-yl]methanol;
$N^2$-[2-(5-methoxy-1H-indol-3-yl)ethyl]-$N^4$-(2-methyl-1H-indol-6-yl)pyrimidine-2,4-diamine;
$N^2$-[2-(5-ethoxy-1H-indol-3-yl)ethyl]-$N^4$-(2-methyl-1H-indol-6-yl)pyrimidine-2,4-diamine;
$N^2$-[2-(5-methoxy-1H-indol-3-yl)ethyl]-$N^4$-(1-methylindol-6-yl)pyrimidine-2,4-diamine;
$N^2$-[2-(5-ethoxy-1H-indol-3-yl)ethyl]-$N^4$-(1-methylindol-6-yl)pyrimidine-2,4-diamine;
$N^2$-[2-(5-methoxy-1H-indol-3-yl)ethyl]-$N^4$-(2-methyl-1H-indol-4-yl)pyrimidine-2,4-diamine;
$N^2$-[2-(5-ethoxy-1H-indol-3-yl)ethyl]-$N^4$-(2-methyl-1H-indol-4-yl)pyrimidine-2,4-diamine;
3-[2-({4-[(1-methylindol-4-yl)amino]pyrimidin-2-yl}amino)ethyl]-1H-indol-5-ol;
$N^2$-[2-(5-ethoxy-1H-indol-3-yl)ethyl]-$N^4$-(1-methylindol-4-yl)pyrimidine-2,4-diamine;
$N^4$-(1,2-dimethylindol-4-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzimidazol-4-yl)pyrimidine-2,4-diamine;
$N^2$-[2-(5-ethoxy-1H-indol-3-yl)ethyl]-$N^4$-(2-methyl-1H-benzimidazol-4-yl)pyrimidine-2,4-diamine;
$N^4$-[2-(5-methoxy-1H-indol-3-yl)ethyl]-$N^2$-(1-methylindol-4-yl)pyrimidine-2,4-diamine;
2-[2-(5-ethoxy-1H-indol-3-yl)ethylamino]-6-[(2-methyl-1H-indol-5-yl)amino]pyrimidine-4-carboxamide;
6-[(1,2-dimethylbenzimidazol-5-yl)amino]-2-[2-(5-methoxy-1H-indol-3-yl)ethylamino]pyrimidine-4-carboxamide;
2-[2-(5-methoxy-1H-indol-3-yl)ethylamino]-6-[(1-methylindol-4-yl)amino]pyrimidine-4-carboxamide;
2-[2-(5-ethoxy-1H-indol-3-yl)ethylamino]-6-[(1-methylindol-4-yl)amino]pyrimidine-4-carboxamide;
$N^2$-[2-(5-methoxy-1H-indol-3-yl)ethyl]-$N^4$-(1-methylindol-4-yl)-6-(4-methylpiperazin-1-yl)pyrimidine-2,4-diamine; and
$N^2$-[2-(5-ethoxy-1H-indol-3-yl)ethyl]-$N^4$-(2-methyl-1H-indol-5-yl)pyrimidine-2,4,5-triamine;
and a pharmaceutically acceptable ester, amide, solvate or salt thereof.

In another aspect of the invention, there is provided a compound of formula I, for use in therapy.

In another aspect of the invention, there is provided a compound of formula I, for use in treatment of cancer.

In another aspect of the invention, there is provided a compound of formula I, for use in treatment of a cancer selected from leukemia, lymphoma, myeloma, breast cancer, ovarian cancer, prostate cancer, lung cancer, pancreatic cancer, and glioma.

The compounds of the invention appear to inhibit tubulin polymerization and/or to induce apoptosis. Consequently, in another aspect of the invention, there is provided a compound of formula I, for use in treatment of a disease, wherein inhibition of tubulin polymerization is beneficial. Further, in another aspect of the invention, there is provided a compound of formula I, for use in treatment of a disease, wherein induction of apoptosis is beneficial.

In another aspect of the invention, there is provided use of a compound of formula I, in the manufacture of a medicament and pharmaceutical compositions for treatment of cancer.

In another aspect of the invention, there is provided use of a compound of formula I, in the manufacture of a medicament and pharmaceutical compositions for treatment a cancer selected from leukemia, lymphoma, myeloma, breast cancer, ovarian cancer, prostate cancer, lung cancer, pancreatic cancer, and glioma.

In another aspect of the invention, there is provided a pharmaceutical composition comprising a compound of formula I, together with pharmaceutically acceptable diluents and carriers.

In another aspect of the invention, there is provided a method for treatment of cancer, which comprises administering to a subject in need thereof, a therapeutically effective amount of a compound of formula I.

In another aspect of the invention, there is provided a method for treatment of cancer selected from leukemia, lymphoma, myeloma, breast cancer, ovarian cancer, prostate cancer, lung cancer, pancreatic cancer, and glioma, which comprises administering to a subject in need thereof, a therapeutically effective amount of a compound of formula I.

In another aspect of the invention, there is provided a method for treatment of cancer, which comprises administering to a subject in need thereof, a therapeutically effective amount of a compound of formula I, in combination with another compound of formula I, in combination with radiation therapy, or in combination with another anticancer agent selected from alkylating agents, antimetabolites, anticancer camptothecin derivatives, plant-derived anticancer agents, antibiotics, enzymes, platinum coordination complexes, tubulin inhibitors, tyrosine kinase inhibitors, hormones, hormone antagonists, monoclonal antibodies, interferons, and biological response modifiers.

Compound names in the present application were generated in accordance with IUPAC by ChemBioDraw Ultra version 11.0.

Depending upon the substituents present in compounds of the formula I, the compounds may form esters, amides, and/or salts which are within the scope of the present invention. Salts and solvates of compounds of formula I which are suitable for use in medicine are those wherein a counterion or an associated solvent is pharmaceutically acceptable. However, salts and solvates having non-pharmaceutically acceptable counterions or associated solvents are within the scope of the present invention, for example, for use as intermediates in the preparation of the compounds of formula I and their pharmaceutically acceptable salts, solvates, and physiologically functional derivatives. By the term "physiologically functional derivative" is meant a chemical derivative of a compound of formula I having the same physiological function as the free compound of formula I, for example, by being convertible in the body thereto. Esters and amides are examples of physiologically functional derivatives.

A compound which, upon administration to the recipient, is capable of being converted into a compound of formula I as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as $(C_1$-$C_4)$alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine, and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, iso-butyl, and sec-butyl groups. Among unbranched alkyl groups, there are preferred methyl, ethyl, n-propyl, and n-butyl groups. Among branched alkyl groups, there may be mentioned iso-propyl, t-butyl, iso-butyl, and sec-butyl groups.

As used herein, the term "alkoxy" means the group O-alkyl, where "alkyl" is used as described above. Examples of alkoxy groups include, but are not limited to, methoxy and ethoxy groups. Other examples include propoxy and butoxy, such as iso-propoxy, n-propoxy, tert-butoxy, iso-butoxy and sec-butoxy.

As used herein, the term "halogen" means fluorine, chlorine, bromine or iodine. Fluorine, chlorine, and bromine are particularly preferred.

As used herein, the term "heterocyclyl" means a cyclic group of carbon atoms wherein from one to three of the carbon atoms is/are replaced by one or more heteroatoms independently selected from nitrogen, oxygen, and sulfur. Examples of heterocyclyl groups include, but are not limited to, tetrahydrofuranyl, pyrrolidinyl, piperidinyl, piperazinyl, morpholinyl, and dioxanyl.

The compounds of the invention may be used in the prophylaxis and treatment as such, or preferably in a form of a pharmaceutical composition. While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below. Thus, the present invention relates to a pharmaceutical composition containing at least one compound of formula I together with conventional excipients.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose, and/or lactose and/or other excipients, binders, extenders, disintegrants, diluents, and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include without limitation starch, methylcellulose, agar, bentonite, xanthan gum, and the like. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose, and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents, and stabilizers may also be added for ease of fabrication and use. Lubricants used in these dosage forms include sodium oleate, sodium stearate, magnesium stearate, sodium benzoate, sodium acetate, sodium chloride, and the like. For oral administration in liquid form, the oral drug components can be combined with any oral, non-toxic, pharmaceutically acceptable inert carrier such as ethanol, glycerol, water, and the like.

The pharmaceutical formulations according to the invention include those suitable for oral, parenteral [including subcutaneous, intradermal, intramuscular, intravenous (bolus or infusion), and intraarticular], inhalation (including fine particle dusts or mists which may be generated by means of various types of metered dose pressurized aerosols), nebulizers or insufflators, rectal, intraperitoneal, and topical (including dermal, buccal, sublingual, and intraocular) administration, although the most suitable route may depend upon, for example, the condition and disorder of the recipient.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally. Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

The compounds of the present invention can also be administered in the form of liposome delivery systems, such as small unilamellar vesicles, large unilamellar vesicles, and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Formulations for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules, and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid and Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The invention also provides the use of a compound of formula I, for the manufacture of a medicament for the treatment or prophylaxis of cancer.

The compounds and the pharmaceutical compositions of the invention may be used in the prophylaxis and treatment of diseases such as cancer, diseases caused by parasites, allergic diseases, Crohns disease, rheumatic diseases, tuberculosis, diabetes, Alzheimer's disease, inflammatory diseases, multiple sclerosis (MS), amyotrophic lateral sclerosis (ALS), Parkinson's disease and diseases caused by bacteria, viruses, and fungus.

The compounds and the pharmaceutical compositions of the invention find particular application in the treatment or prophylaxis of various proliferative disorders and cancer types, including but not limited to, cancer of the bone, breast, respiratory tract, brain, reproductive organs, digestive tract, urinary tract, eye, liver, skin, head, neck, thyroid, parathyroid, and metastatic forms thereof. Proliferative disorders of the breast include, but are not limited to, invasive ductal carcinoma, invasive lobular carcinoma, ductal carcinoma, lobular carcinoma in situ, and metastatic breast cancer. Proliferative disorders of the skin include, but are not limited to, basal cell carcinoma, squamous cell carcinoma, malignant melanoma, and Kaposi's sarcoma. Proliferative disorders of the respiratory tract include, but are not limited to, small cell and non-small cell lung carcinoma, bronchial adenoma, pleuropulmonary blastoma, and malignant mesothelioma. Proliferative disorders of the brain include, but are not limited to, brain stem and hypothalamic glioma, cerebellar and cerebral astrocytoma, medulloblastoma, ependymal tumors, oligodendroglial tumors, meningiomas and neuroectodermal, and pineal tumors. Proliferative disorders of the male reproductive organs include, but are not limited to, prostate, testicular, and penis cancer. Proliferative disorders of the female reproductive organs include, but are not limited to, uterine, cervical, ovarian, vaginal, vulval cancer, uterine sarcoma, and ovarian germ cell tumor. Proliferative disorders of the digestive tract include, but are not limited to, anal, colon, colorectal, esophageal, gall bladder, stomach, pancreatic, rectal, small intestine, and salivary gland cancer. Proliferative disorders of the liver include, but are not limited to, hepatocellular carcinoma, cholangiocarcinoma, and primary liver cancer. Proliferative disorders of the eye include, but are not limited to, intraocular melanoma, retinoblastoma, and rhabdomyosarcoma. Proliferative disorders of the head include, but are not limited to, laryngeal, hypopharyngeal, nasopharyngeal, oropharyngeal, lip, oral, and metastatic paranasal sinus cancer. Proliferative disorders of the lymphomas include, but are not limited to, T cell and B cell lymphomas, non-Hodgkin's lymphoma, cutaneous T cell lymphoma, Hodgkin's disease, and lymphoma of the central nervous system. Leukemia includes, but is not limited to, acute myeloid leukemia, chronic myelogenous leukemia, and hairy cell leukemia. Proliferative disorders of the thyroid include, but are not limited to, thyroid cancer, thymoma, and malignant thymoma. Proliferative disorders of the urinary tract include, but are not limited to, kidney cancer and bladder cancer. Sarcomas include, but are not limited to, sarcoma of the soft tissue, osteosarcoma, malignant fibrous histiocytoma, lymphosarcoma, and rhabdomyosarcoma.

Preferably, the compounds and the pharmaceutical compositions of the invention find particular application in the treatment or prophylaxis of the following: breast cancer, leukemia, lung cancer, myeloma, lymphoma, ovarian cancer, pancreatic cancer, prostate cancer, and glioma.

Whilst a compound of the invention may be used alone, it is also possible for the compounds to be used in combination with each other, in combination with radiation therapy, or in combination with other anticancer agents. Various classes of anticancer and antineoplastic compounds include, but are not limited to, alkylating agents, antimetabolites, anticancer camptothecin derivatives, plant-derived anticancer agents, antibiotics, enzymes, platinum coordination complexes, tubulin inhibitors, tyrosine kinase inhibitors, hormones and hormone antagonists, monoclonal antibodies, interferons, biological response modifiers and other anticancer agents. Examples of alkylating agents include, but are not limited to, mechlorethamine, cyclophosphamide, ifosfamide, melphalan, chlorambucil, busulfan, mitobronitol, ranimustin, nimustin, temozolomide, and carmustine; examples of antimetabolites include, but are not limited to, methotrexate, fluorouracil, cytarabine, gemcitabine, fludarabine, mercaptopurine, thioguanine, and azathioprine; examples of camptothecin derivatives include, but are not limited to, irinotecan, topotecan, and camptothecin; examples of plant-derived agents include, but are not limited to, vinblastine, vincristine, docetaxel, paclitaxel, and colchicines; examples of antibiotics include, but are not limited to, actinomycin D, daunorubicin, and bleomycin. One example of enzyme effective as antineoplastic agent includes L-asparaginase. Examples of coordination compounds include, but are not limited to, cisplatin and carboplatin; examples of tubulin inhibitors include, but are not limited to, the above mentioned plant-derived agents; examples of tyrosine kinase inhibitors include, but are not limited to, gefitinib, imatinib, sunitinib, nilotinib, dasatinib, erlotinib, and pazopanib; examples of hormones and hormone related compounds include, but are not limited to, prednisone, dexamethasone, formestane, aminoglutethimide, anastrozole, hydroxyprogesterone caproate, medroxyprogesterone, and tamoxifen; examples of interferons include, but are not limited to, interferon α, interferon α-2a, interferon α-2b, interferon β, interferon γ-1a, and interferon γ-n1; examples of biological response modifiers include, but are not limited to, krestin, lentinan, sizofiran, picibanil, and ubenimex. Examples of other anticancer agents include, but are not limited to, mitoxantrone, procarbazine, dacarbazine, hydroxycarbamide, pentostatin, tretinoin, leuprorelin, flutamide, and aldesleukin.

Several synthetic routes to the compounds of the present invention can be devised by any person skilled in the art and the possible synthetic routes described below do not limit the invention.

Procedures for Synthesizing Compounds of General Formula I

Method A

The appropriate amine (II or V) was dissolved in isopropanol (0.2 g/mL). 1.1 Eq of pyrimidine (III) and 1.2 eq of N,N-diisopropylethylamine (DIPEA) were added and the mixture was stirred at temperatures between 25° C. and 80° C. for 1 h. The reaction mixture was dissolved in EtOAc/MeOH 9:1 and washed with saturated aqueous NaHCO₃, water, and brine. The solvent was removed in vacuo and the residue was purified by column chromatography on silica gel with heptane/EtOAc, EtOAc and/or EtOAc/MeOH as eluent to give the intermediate (IV' or IV").

The intermediate (IV' or IV") was dissolved in ethylene glycol (0.2 g/mL, in some instances NMP was used alone or as a cosolvent in order to fully dissolve the reactants) and 1.3 eq of amine (II or V) and 1.3 eq of N,N-diisopropylethylamine (DIPEA) were added. The mixture was then stirred at temperatures between 100 and 150° C. for 1-3 h. The reaction mixture was dissolved in EtOAc/MeOH 9:1 and washed with saturated aqueous NaHCO₃, water, and brine. The solvent was removed in vacuo and the residue was purified by column chromatography on silica gel with heptane/EtOAc, EtOAc, EtOAc/MeOH/TEA and/or CH₂Cl₂/MeOH as eluent to give the compound of formula I. This procedure is exemplified in Scheme 1.

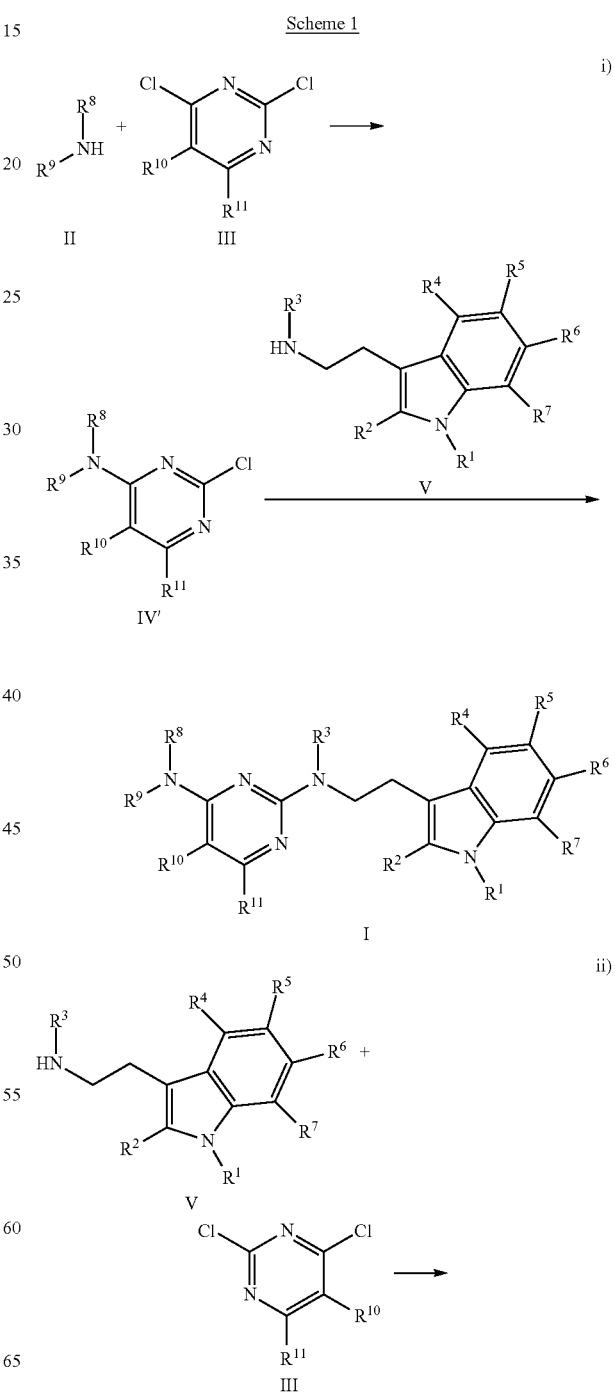

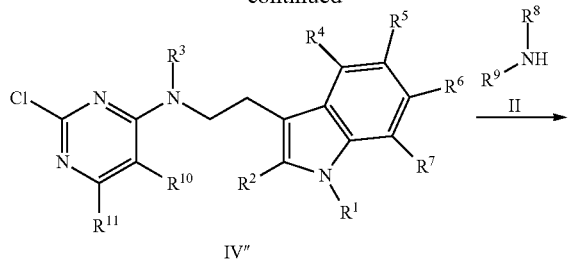

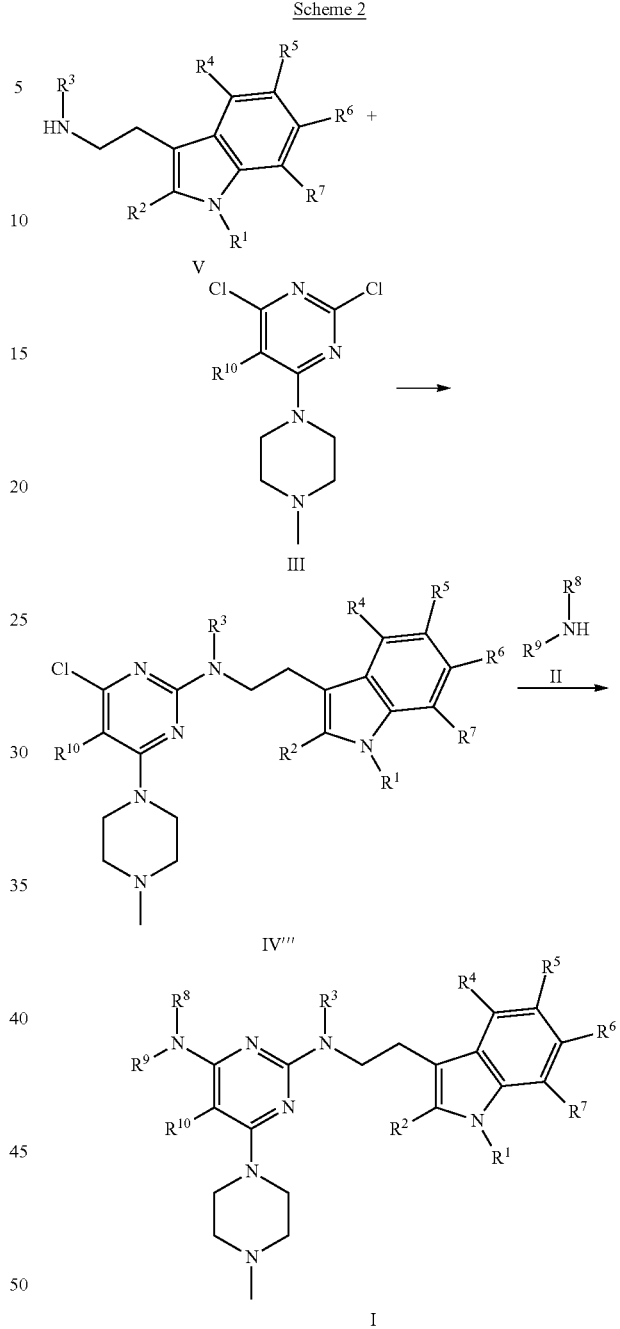

Compounds of Examples 1-14, 16-21, 26-29, 47-58, 73-78, 79-83, and 85-88 were synthesized by Method A pathway (i), and compounds of Examples 22-25 and 85 were synthesized by Method A pathway (ii) (as set out in Scheme 1). Compounds of Examples 15, 59, 60, and 72 were synthesized by Method A pathway (i), but additionally protected via silylation (t-butyldimethylsilyl chloride, imidazole, DMF) after the first step and deprotected (tetrabutylammonium fluoride, THF) after the second step. Compounds of Examples 61 and 62 were synthesized by method A pathway (i), but additionally alkylated (according to scheme 3) after the first step. Compound of Example 90 was synthesized by Method A pathway (i), but an additional reduction step of intermediate 99 had to be carried out (hydrogenation on 10% Pd/C in methanol). $R^1$-$R^{11}$ are as defined in formula I.

Method B

The appropriate amine (V) was dissolved in isopropanol/N-methyl-2-pyrrolidone (0.2 g/mL). 1.0 eq of pyrimidine (III), 1.0 eq of N,N-diisopropylethylamine (DIPEA), and 1.2 eq of NaI were added and the mixture was stirred at 150° C. for 12 h. The reaction mixture was dissolved in EtOAc/MeOH 9:1 and washed with saturated aqueous $NaHCO_3$, water, and brine. The solvent was removed in vacuo and the residue was purified by column chromatography on silica gel with EtOAc/MeOH/TEA as eluent to give the intermediate (IV''').

Intermediate (IV''') was added to a solution of 0.10 eq $Pd(OAc)_2$, 0.15 eq 2,2'-bis(diphenylphosphino)-1,1'-binaphthyl (BINAP), and 1.5 eq $CsCO_3$ in N-methyl-2-pyrrolidone (NMP) (0.2 g/mL) under an atmosphere of argon. The mixture was then stirred at 150° C. for 1 h. The reaction mixture was dissolved in EtOAc/MeOH 9:1 and washed with saturated aqueous $NaHCO_3$, water, and brine. The solvent was removed in vacuo and the residue was purified by column chromatography on silica gel with EtOAc/MeOH/TEA as eluent to give the compound of formula I. This procedure is exemplified in Scheme 2.

Examples 30 and 89 were synthesized by Method B (as set out in Scheme 2). $R^1$-$R^{10}$ are as defined in formula I.

Procedure for Synthesizing the Intermediates of General Formula VI''

In order to access certain methylated analogues the appropriate monosubstituted pyrimidine (VI') was dissolved in dimethylformamide (0.1 g/mL). 2 Eq of $Cs_2CO_3$ and 2 eq of iodomethane were added and the mixture was stirred at room temperature for 24 hours. The reaction mixture was dissolved in EtOAc and washed with water. The solvent was removed in vacuo and the residue was purified by column chromatography on silica gel with heptane/EtOAc as eluent to give the compound (VI''). The procedure is exemplified in Scheme 3.

Scheme 3

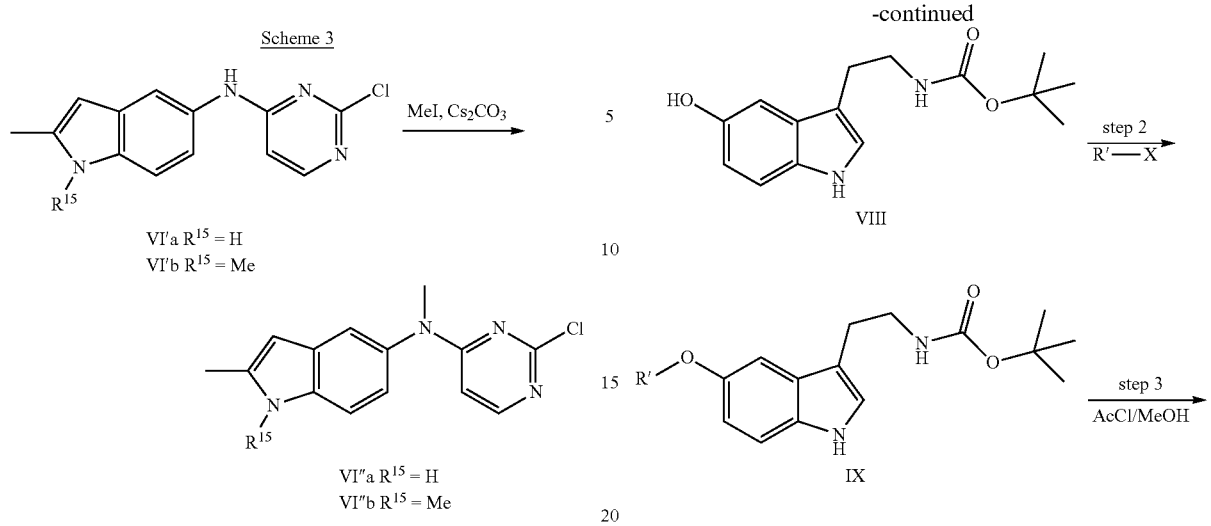

VI'a R[15] = H
VI'b R[15] = Me

VI"a R[15] = H
VI"b R[15] = Me

Intermediate compounds 70 and 71 were synthesized by this reaction procedure (as set out in scheme 3).

Procedure for Synthesizing Tryptamine Derivatives of Formula X

Step 1: Serotonin hydrochloride (VII) was dissolved in water (20 mg/mL). 3 Eq of potassium carbonate and 1 eq of di-tert-butyl dicarbonate were added and the mixture was stirred at room temperature for 24 h. The aqueous reaction mixture was extracted with EtOAc and the organic phase was washed with water, 1 M HCl (aq) and brine. The solvent was removed in vacuo and the residue was purified by column chromatography on silica gel with $CH_2Cl_2$/MeOH as eluent to give tert-butyl 2-(5-hydroxy-1H-indol-3-yl)ethylcarbamate (VIII).

Step 2: Tert-butyl 2-(5-hydroxy-1H-indol-3-yl)ethylcarbamate (VIII), 3-9 eq potassium carbonate, and 0-1 eq NaI were premixed in 2-butanone or acetone (25 mg/mL). After 5 min, 3-5 eq alkyl halide (R'—X=bromoethane or 4-(2-chloroethyl)morpholine×HCl or 1-iodopropane or 2-iodopropane respectively) was added and the mixture was stirred at 60-90° C. for 1-5 days. The reaction mixture was dissolved in EtOAc and washed with saturated aqueous $NaHCO_3$. The solvent was removed in vacuo and the residue was purified by column chromatography on silica gel with $CH_2Cl_2$/acetone or heptane/EtOAc as eluent to give the alkylated derivative (IX).

Step 3: The alkylated derivative (IX) was dissolved in methanol (10 mg/mL), added dropwise to a solution of 10 eq acetyl chloride in methanol at 0° C. and left at room temperature over night. The reaction mixture was concentrated, a small portion of acetone was added and the precipitate was filtered off to give the desired amine as a hydrochloride salt (X).

This procedure is exemplified in Scheme 4.

Scheme 4

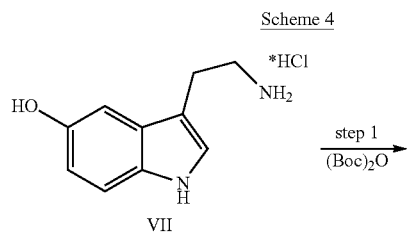

Tryptamine derivatives of formula X were produced by this procedure (as set out in Scheme 4) and used in the syntheses of examples 5, 6, 48, 49, 55, 58, 72, 74, 76, 78, 80, 83, 85, 88, and 90.

EXAMPLE 1

$N^2$-[2-(1H-indol-3-yl)ethyl]-$N^4$-(1H-indol-5-yl)pyrimidine-2,4-diamine

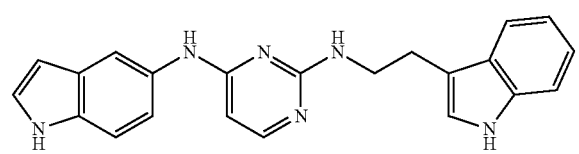 [SMILES: c1ccc2c(CCNc3nccc(Nc4ccc5[nH]ccc5c4)n3)c[nH]c2c1]

$^1$H NMR (500 MHz, DMSO-$d_6$, 75° C.) δ 10.77 (s, 1H), 10.61 (s, 1H), 8.58 (s, 1H), 7.81 (s, 1H), 7.79 (d, 1H), 7.57 (d, 1H), 7.34 (d, 1H), 7.30 (d, 1H), 7.25 (m, 1H), 7.20 (d, 1H), 7.14 (s, 1H), 7.06 (t, 1H), 6.96 (t, 1H), 6.30 (s, 1H), 6.24 (m, 1H), 5.93 (d, 1H), 3.60 (q, 2H), 3.00 (t, 2H).

MS (ESI$^+$) m/z 369.3 [M+H]$^+$.

EXAMPLE 2

N$^4$-(1H-indol-5-yl)-N$^2$-[2-(5-methoxy-1H-indol-3-yl)ethyl]pyrimidine-2,4-diamine

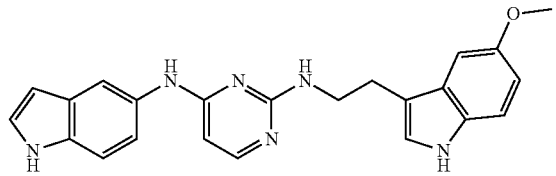 [SMILES: COc1ccc2[nH]cc(CCNc3nccc(Nc4ccc5[nH]ccc5c4)n3)c2c1]

$^1$H NMR (500 MHz, DMSO-d$_6$, 75° C.) δ 10.77 (s, 1H), 10.45 (s, 1H), 8.57 (s, 1H), 7.82 (s, 1H), 7.79 (d, 1H), 7.29 (d, 1H), 7.25-7.18 (m, 3H), 7.10 (s, 1H), 7.08 (s, 1H), 6.72 (dd, 1H), 6.30 (s, 1H), 6.22 (m, 1H), 5.94 (d, 1H), 3.75 (s, 3H), 3.58 (q, 2H), 2.95 (t, 2H).

MS (ESI$^+$) m/z 399.3 [M+H]$^+$.

EXAMPLE 3

N$^2$-[2-(1H-indol-3-yl)ethyl]-N$^4$-(2-methyl-1H-indol-5-yl)pyrimidine-2,4-diamine

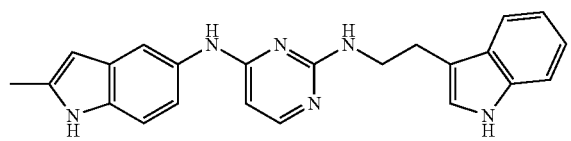

$^1$H NMR (500 MHz, DMSO-d$_6$) δ 10.37 (s, 1H), 10.34 (s, 1H), 8.18 (br s, 1H), 7.76 (d, 1H), 7.58 (d, 1H), 7.56 (br s, 1H), 7.36 (d, 1H), 7.20 (d, 1H), 7.09-7.06 (m, 3H), 7.00 (t, 1H), 6.02 (s, 1H), 5.94 (d, 1H), 5.54 (br s, 1H); 3.67 (q, 2H), 3.04 (t, 2H), 2.41 (s, 3H).

MS (ESI$^+$) m/z 383.2 [M+H]$^+$.

EXAMPLE 4

N$^2$-[2-(5-methoxy-1H-indol-3-yl)ethyl]-N$^4$-(2-methyl-1H-indol-5-yl)pyrimidine-2,4-diamine

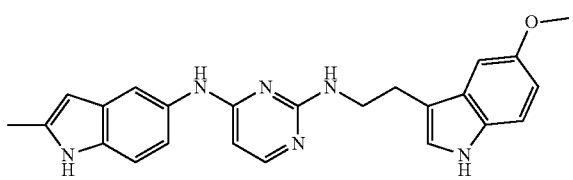

$^1$H NMR (500 MHz, DMSO-d$_6$, 75° C.) δ 10.45 (s, 1H), 8.50 (s, 1H), 7.77 (d, 1H), 7.65 (s, 1H), 7.23 (d, 1H), 7.17 (d, 1H), 7.11-7.07 (m, 3H), 6.72 (dd, 1H), 6.20 (m, 1H), 5.97 (s, 1H), 5.91 (d, 1H), 3.75 (s, 3H), 3.58 (q, 2H), 2.95 (t, 2H), 2.36 (s, 3H).

MS (ESI$^+$) m/z 413.4 [M+H]$^+$.

EXAMPLE 5

N$^2$-[2-(5-ethoxy-1H-indol-3-yl)ethyl]-N$^4$-(2-methyl-1H-indol-5-yl)pyrimidine-2,4-diamine

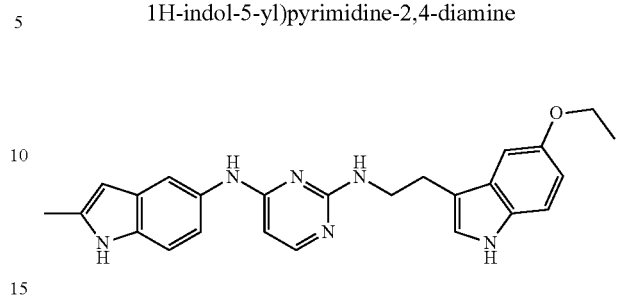

$^1$H NMR (500 MHz, DMSO-d$_6$, 75° C.) δ 10.56 (s, 1H), 10.43 (s, 1H), 8.50 (s, 1H), 7.77 (d, 1H), 7.65 (s, 1H), 7.22 (d, 1H), 7.15 (d, 1H), 7.09-7.06 (m, 3H), 6.71 (dd, 1H), 6.19 (m, 1H), 5.97 (s, 1H), 5.91 (d, 1H), 4.01 (q, 2H), 3.57 (q, 2H), 2.93 (t, 2H), 2.36 (s, 3H), 1.31 (t, 3H).

MS (ESI$^+$) m/z 427.3 [M+H]$^+$.

EXAMPLE 6

N$^4$-(2-methyl-1H-indol-5-yl)-N$^2$-{2-[5-(2-morpholinoethoxy)-1H-indol-3-yl]ethyl}pyrimidine-2,4-diamine

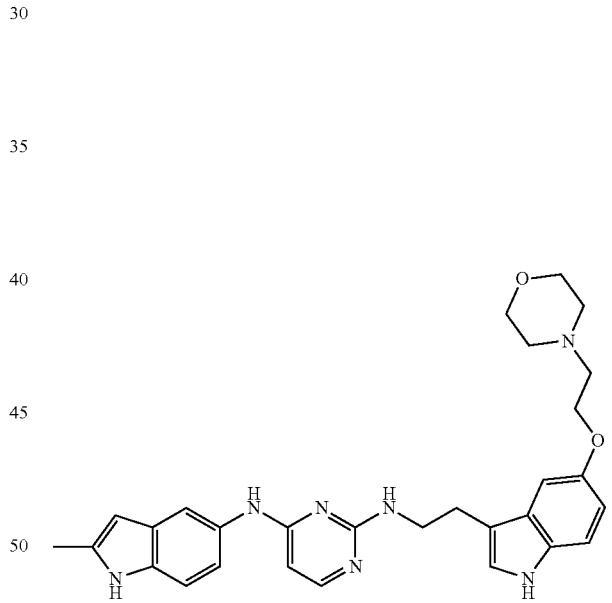

$^1$H NMR (500 MHz, DMSO-d$_6$, 75° C.) δ 10.56 (s, 1H), 10.45 (s, 1H), 8.50 (s, 1H), 7.77 (d, 1H), 7.66 (s, 1H), 7.22 (d, 1H), 7.15 (d, 1H), 7.10-7.07 (m, 3H), 6.72 (dd, 1H), 6.19 (m, 1H), 5.96 (s, 1H), 5.91 (d, 1H), 4.07 (t, 2H), 3.57 (m, 6H), 2.94 (t, 2H), 2.68 (t, 2H), 2.47 (m, 4H), 2.35 (s, 3H).

MS (ESI$^+$) m/z 512.4 [M+H]$^+$.

EXAMPLE 7

N$^4$-(2-methyl-1H-indol-5-yl)-N$^2$-{2-[5-(trifluoromethoxy)-1H-indol-3-yl]ethyl}pyrimidine-2,4-diamine

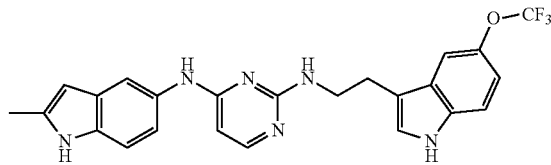 [SMILES: Cc1cc2cc(Nc3ccnc(NCCc4c[nH]c5ccc(OC(F)(F)F)cc45)n3)ccc2[nH]1]

$^1$H NMR (500 MHz, DMSO-d$_6$, 75° C.) δ 10.93 (s, 1H), 10.56 (s, 1H), 8.50 (s, 1H), 7.77 (d, 1H), 7.64 (s, 1H), 7.53 (s, 1H), 7.42 (d, 1H), 7.28 (s, 1H), 7.16 (d, 1H), 7.08 (dd, 1H), 7.02 (d, 1H), 6.26 (br s, 1H), 5.97 (s, 1H), 5.92 (d, 1H), 3.57 (q, 2H), 2.97 (t, 2H), 2.36 (s, 3H).
MS (ESI$^+$) m/z 467.2 [M+H]$^+$.

EXAMPLE 8

3-{2-[4-(2-methyl-1H-indol-5-ylamino)pyrimidin-2-ylamino]ethyl}-1H-indol-5-ol

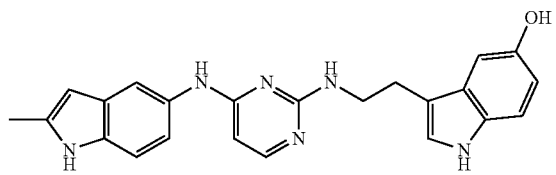 [SMILES: Cc1cc2cc(Nc3ccnc(NCCc4c[nH]c5ccc(O)cc45)n3)ccc2[nH]1]

$^1$H NMR (500 MHz, CD$_3$OD) δ 7.66 (d, 1H), 7.52 (br s, 1H), 7.20-7.14 (m, 2H), 7.03 (br s, 1H), 7.01 (s, 1H), 6.97 (s, 1H), 6.66 (dd, 1H), 6.01 (s, 1H), 5.90 (d, 1H), 3.63 (t, 2H), 2.96 (t, 2H), 2.38 (s, 3H).
MS (ESI$^+$) m/z 399.3 [M+H]$^+$.

EXAMPLE 9

N$^2$-[2-(5-methyl-1H-indol-3-yl)ethyl]-N$^4$-(2-methyl-1H-indol-5-yl)pyrimidine-2,4-diamine

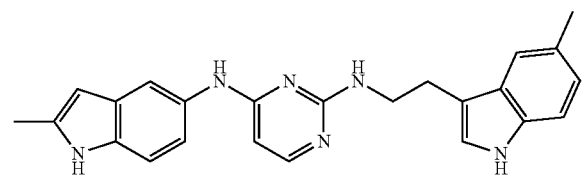 [SMILES: Cc1ccc2[nH]cc(CCNc3nccc(Nc4ccc5[nH]c(C)cc5c4)n3)c2c1]

$^1$H NMR (500 MHz, DMSO-d$_6$, 75° C.) δ 10.56 (s, 1H), 10.46 (s, 1H), 8.50 (s, 1H), 7.77 (d, 1H), 7.65 (s, 1H), 7.34 (s, 1H), 7.23 (d, 1H), 7.15 (d, 1H), 7.11-7.08 (m, 2H), 6.89 (d, 1H), 6.18 (m, 1H), 5.97 (s, 1H), 5.91 (d, 1H), 3.58 (q, 2H), 2.95 (t, 2H), 2.37 (s, 3H), 2.36 (s, 3H).
MS (ESI$^+$) m/z 397.3 [M+H]$^+$.

EXAMPLE 10

N$^2$-[2-(5-fluoro-1H-indol-3-yl)ethyl]-N$^4$-(2-methyl-1H-indol-5-yl)pyrimidine-2,4-diamine

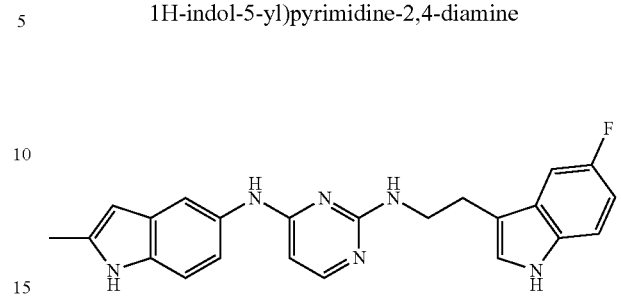

$^1$H NMR (500 MHz, DMSO-d$_6$,) δ 10.90 (s, 1H), 10.73 (s, 1H), 8.75 (br s, 1H), 7.74 (m, 2H), 7.32 (m, 2H), 7.24 (s, 1H), 7.13 (d, 1H), 7.08 (d, 1H), 6.90 (t, 1H), 6.53 (br s, 1H), 5.90 (d, 2H), 3.53 (m, 2H), 2.92 (m, 1H), 2.33 (s, 3H).
MS (ESI$^+$) m/z 401.3 [M+H]$^+$.

EXAMPLE 11

N$^2$-[2-(6-methoxy-1H-indol-3-yl)ethyl]-N$^4$-(2-methyl-1H-indol-5-yl)pyrimidine-2,4-diamine

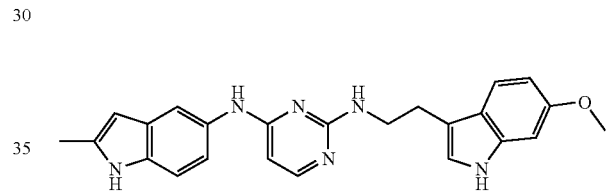

$^1$H NMR (500 MHz, DMSO-d$_6$, 75° C.) δ 10.56 (s, 1H), 10.40 (s, 1H), 8.50 (s, 1H), 7.77 (d, 1H), 7.64 (s, 1H), 7.42 (d, 1H), 7.16 (d, 1H), 7.09 (d, 1H), 6.99 (s, 1H), 6.86 (s, 1H), 6.63 (d, 1H), 6.17 (t, 1H), 5.98 (s, 1H), 5.90 (d, 1H), 3.77 (s, 3H), 3.57 (q, 2H), 2.92 (t, 2H), 2.36 (s, 3H).
MS (ESI$^+$) m/z 413.3 [M+H]$^+$.

EXAMPLE 12

N$^2$-[2-(7-methoxy-1H-indol-3-yl)ethyl]-N$^4$-(2-methyl-1H-indol-5-yl)pyrimidine-2,4-diamine

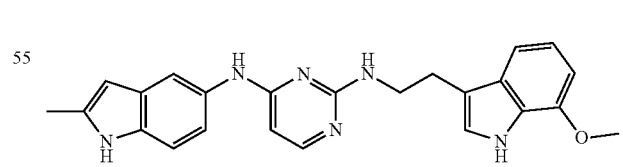

$^1$H NMR (500 MHz, DMSO-d$_6$, 75° C.) δ 10.65 (s, 1H), 10.57 (s, 1H), 8.50 (s, 1H), 7.76 (d, 1H), 7.64 (s, 1H), 7.18-7.15 (m, 2H), 7.10 (m, 1H), 7.06 (m, 1H), 6.89 (t, 1H), 6.64 (d, 1H), 6.19 (m, 1H), 5.97 (s, 1H), 5.90 (d, 1H), 3.91 (s, 3H), 3.57 (q, 2H), 2.95 (t, 2H), 2.36 (s, 3H).
MS (ESI$^+$) m/z 413.3 [M+H]$^+$.

EXAMPLE 13

N⁴-(1,2-dimethyl-1H-indol-5-yl)-N²-[2-(5-methoxy-1H-indol-3-yl)ethyl]pyrimidine-2,4-diamine

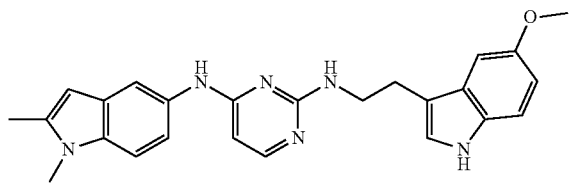

¹H NMR (500 MHz, DMSO-d$_6$, 75° C.) δ 10.45 (s, 1H), 8.56 (s, 1H), 7.78 (d, 1H), 7.70 (s, 1H), 7.25-7.20 (m, 3H), 7.10 (d, 1H), 7.07 (d, 1H), 6.73 (dd, 1H), 6.23 (br s, 1H), 6.05 (s, 1H), 5.92 (d, 1H), 3.74 (s, 3H), 3.62 (s, 3H), 3.58 (q, 2H), 2.95 (t, 2H), 2.37 (s, 3H).
MS (ESI⁺) m/z 427.3 [M+H]⁺.

EXAMPLE 14

N⁴-(2,3-dimethyl-1H-indol-5-yl)-N²-[2-(5-methoxy-1H-indol-3-yl)ethyl]pyrimidine-2,4-diamine

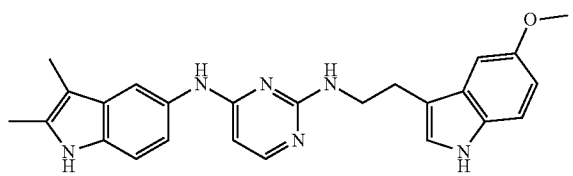

¹H NMR (500 MHz, DMSO-d$_6$, 75° C.) δ 10.44 (s, 1H), 10.31 (s, 1H), 8.52 (s, 1H), 7.77 (d, 1H), 7.63 (s, 1H), 7.23 (d, 1H), 7.13-7.05 (m, 4H), 6.72 (dd, 1H), 6.15 (m, 1H), 5.91 (d, 1H), 3.74 (s, 3H), 3.60 (q, 2H), 2.95 (t, 2H), 2.29 (s, 3H), 2.07 (s, 3H).
MS (ESI⁺) m/z 427.3 [M+H]⁺.

EXAMPLE 15

(5-{2-[2-(5-methoxy-1H-indol-3-yl)ethylamino]pyrimidin-4-ylamino}-1H-indol-2-yl)methanol

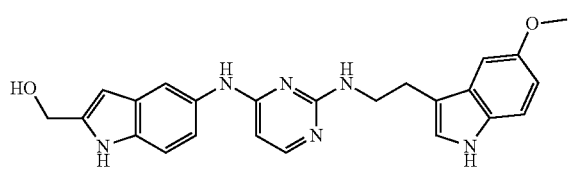 [SMILES: COc1ccc2[nH]cc(CCNc3nccc(Nc4ccc5[nH]c(CO)cc5c4)n3)c2c1]

¹H NMR (500 MHz, DMSO-d$_6$, 75° C.) δ 10.65 (s, 1H), 10.44 (s, 1H), 8.53 (s, 1H), 7.78 (d, 1H), 7.72 (s, 1H), 7.23 (d, 2H), 7.15 (dd, 1H), 7.10 (d, 1H), 7.08 (d, 1H), 6.72 (dd, 1H), 6.20 (t, 1H), 6.15 (s, 1H), 5.92 (d, 1H), 4.95 (t, 1H), 4.59 (d, 2H), 3.75 (s, 3H), 3.58 (q, 2H), 2.95 (t, 2H).
MS (ESI⁺) m/z 429.4 [M+H]⁺.

EXAMPLE 16 methyl 5-{2-[2-(5-methoxy-1H-indol-3-yl)ethylamino]pyrimidin-4-ylamino}-1H-indole-2-carboxylate

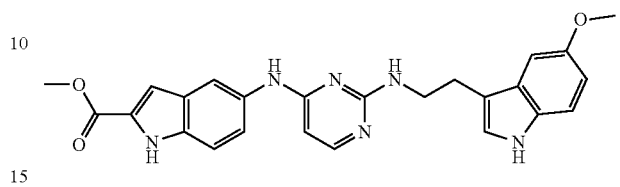

¹H NMR (500 MHz, DMSO-d$_6$, 75° C.) δ 11.56 (s, 1H), 10.44 (s, 1H), 8.74 (s, 1H), 8.03 (s, 1H), 7.82 (d, 1H), 7.41-7.35 (m, 2H), 7.23 (d, 1H), 7.10 (d, 1H), 7.07 (d, 1H), 6.96 (s, 1H), 6.72 (dd, 1H), 6.30 (t, 1H), 5.97 (d, 1H), 3.87 (s, 3H), 3.73 (s, 3H), 3.60 (q, 2H), 2.96 (t, 2H).
MS (ESI⁺) m/z 457.3 [M+H]⁺.

EXAMPLE 17

2-hydroxyethyl 5-{2-[2-(5-methoxy-1H-indol-3-yl)ethylamino]pyrimidin-4-ylamino}-1H-indole-2-carboxylate

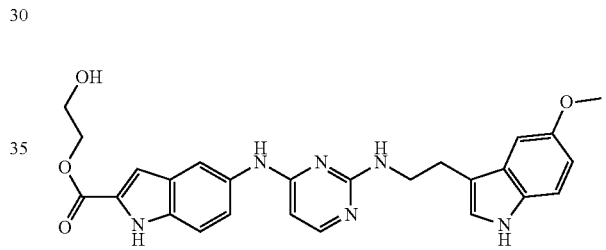

¹H NMR (500 MHz, DMSO-d$_6$, 75° C.) δ 11.51 (s, 1H), 10.44 (s, 1H), 8.75 (s, 1H), 8.04 (s, 1H), 7.82 (d, 1H), 7.42-7.36 (m, 2H), 7.23 (d, 1H), 7.10 (d, 1H), 7.07 (d, 1H), 7.01 (s, 1H), 6.72 (dd, 1H), 6.31 (m, 1H), 5.97 (d, 1H), 4.71 (m, 1H), 4.32 (t, 2H), 3.75 (m, 2H), 3.74 (s, 3H), 3.60 (q, 2H), 2.96 (t, 2H).
MS (ESI⁺) m/z 487.2 [M+H]⁺.

EXAMPLE 18

N⁴-(1H-benzo[d]imidazol-5-yl)-N²-[2-(5-methoxy-1H-indol-3-yl)ethyl]pyrimidine-2,4-diamine

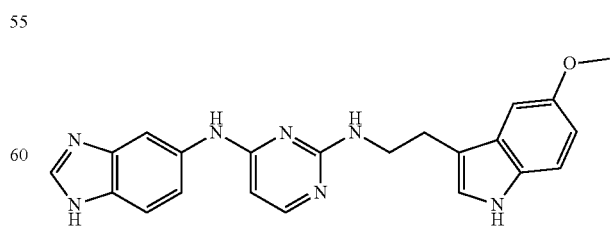

¹H NMR (500 MHz, DMSO-d$_6$, 75° C.) δ 12.07 (br s, 1H), 10.45 (s, 1H), 8.84 (br s, 1H), 8.05 (s, 1H), 8.00-7.88 (m, 1H), 7.83 (d, 1H), 7.47 (m, 1H), 7.38 (d, 1H), 7.22 (d, 1H), 7.12 (br s, 1H), 7.07 (s, 1H), 6.71 (d, 1H), 6.29 (br s, 1H), 6.00 (d, 1H), 3.74 (s, 3H), 3.59 (q, 2H), 2.95 (t, 3H).
MS (ESI⁺) m/z 400.3 [M+H]⁺.

EXAMPLE 19

N²-[2-(5-methoxy-1H-indol-3-yl)ethyl]-N⁴-(2-methyl-1H-benzo[d]imidazol-5-yl)pyrimidine-2,4-diamine

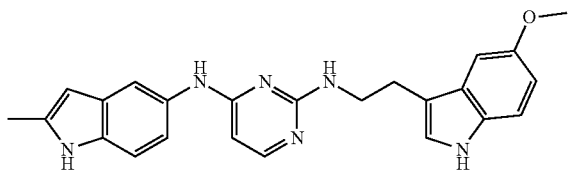

¹H NMR (500 MHz, DMSO-d₆, 75° C.) δ 11.76 (br s, 1H), 10.45 (s, 1H), 8.75 (br s, 1H), 7.82 (d, 1H), 7.78 (br s, 1H), 7.34-7.28 (m, 2H), 7.23 (d, 1H), 7.13 (br s, 1H), 7.07 (d, 1H), 6.72 (dd, 1H), 6.26 (br s, 1H), 5.97 (d, 1H), 3.74 (s, 3H), 3.59 (q, 2H), 2.95 (t, 2H), 2.46 (s, 3H).
MS (ESI⁺) m/z 414.3 [M+H]⁺.

EXAMPLE 20

N⁴-(1H-indol-6-yl)-N²-[2-(5-methoxy-1H-indol-3-yl)ethyl]pyrimidine-2,4-diamine

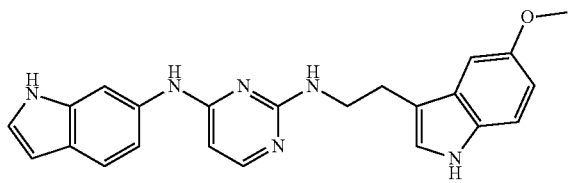 [SMILES: COc1ccc2[nH]cc(CCNc3nccc(Nc4ccc5cc[nH]c5c4)n3)c2c1]

¹H NMR (500 MHz, DMSO-d₆, 75° C.) δ 10.66 (s, 1H), 10.45 (s, 1H), 8.71 (s, 1H), 7.82 (d, 1H), 7.71 (s, 1H), 7.41 (d, 1H), 7.23 (d, 1H), 7.21-7.19 (m, 2H), 7.10 (d, 1H), 7.08 (d, 1H), 6.72 (dd, 1H), 6.35 (s, 1H), 6.18 (m, 1H), 6.00 (d, 1H), 3.75 (s, 3H), 3.61 (q, 2H), 2.96 (t, 2H).
MS (ESI⁺) m/z 399.2 [M+H]⁺.

EXAMPLE 21

N⁴-(1H-indol-4-yl)-N²-[2-(5-methoxy-1H-indol-3-yl)ethyl]pyrimidine-2,4-diamine

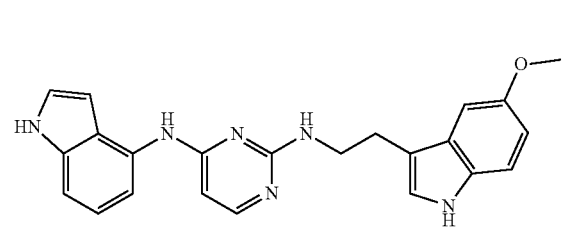 [SMILES: COc1ccc2[nH]cc(CCNc3nccc(Nc4cccc5[nH]ccc45)n3)c2c1]

¹H NMR (500 MHz, DMSO-d₆, 75° C.) δ 10.89 (s, 1H), 10.45 (s, 1H), 8.51 (s, 1H), 7.85 (d, 1H), 7.66 (d, 1H), 7.24-7.22 (m, 2H), 7.11-7.07 (m, 3H), 6.98 (t, 1H), 6.72 (dd, 1H), 6.64 (m, 1H), 6.30 (m, 1H), 6.13 (d, 1H), 3.75 (s, 3H), 3.58 (q, 2H), 2.94 (t, 2H).
MS (ESI⁺) m/z 399.3 [M+H]⁺.

EXAMPLE 22

N⁴-[2-(1H-indol-3-yl)ethyl]-N²-(2-methyl-1H-indol-5-yl)pyrimidine-2,4-diamine

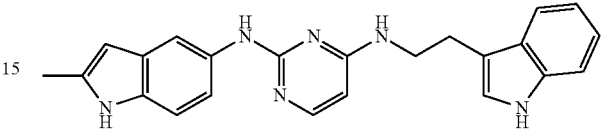

¹H NMR (300 MHz, DMSO-d₆) δ 10.81 (br s, 1H), 10.57 (br s, 1H), 8.47 (s, 1H), 7.85 (s, 1H), 7.73 (br s, 1H), 7.52 (d, 1H), 7.33 (d, 1H), 7.22 (d, 1H), 7.16 (s, 1H), 7.11 (br s, 1H), 7.06 (t, 2H), 6.95 (t, 1H), 5.84 (d, 2H), 3.61 (br s, 2H), 2.96 (t, 1H), 2.30 (s, 3H).
MS (ESI⁺) m/z 383.3 [M+H]⁺.

EXAMPLE 23

N⁴-[2-(5-methoxy-1H-indol-3-yl)ethyl]-N²-(2-methyl-1H-indol-5-yl)pyrimidine-2,4-diamine

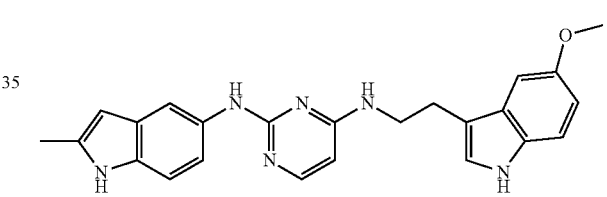

¹H NMR (500 MHz, DMSO-d₆, 75° C.) δ 10.48 (s, 1H), 10.40 (s, 1H), 8.18 (s, 1H), 7.83 (d, 1H), 7.76 (d, 1H), 7.24 (d, 2H), 7.12 (d, 1H), 7.07 (d, 1H), 7.02 (d, 1H), 6.80 (br s, 1H), 6.73 (dd, 1H), 5.90 (s, 1H), 5.87 (d, 1H), 3.74 (s, 3H), 3.61 (q, 2H), 2.97 (t, 2H), 2.34 (s, 3H).
MS (ESI⁺) m/z 413.3 [M+H]⁺.

EXAMPLE 24

N⁴-[2-(1H-indol-3-yl)ethyl]-N²-(1H-indol-6-yl)pyrimidine-2,4-diamine

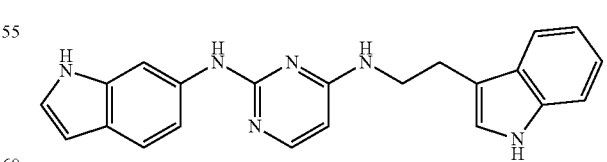

¹H NMR (500 MHz, DMSO-d₆) δ 10.82 (s, 1H), 10.78 (s, 1H), 8.72 (s, 1H), 8.06 (s, 1H), 7.78 (br s, 1H), 7.54 (d, 1H) 7.35-7.30 (m, 2H), 7.26 (d, 1H), 7.20-7.10 (m, 3H), 7.06 (t, 1H), 6.95 (t, 1H), 6.29 (s, 1H), 5.90 (d, 1H), 3.65 (br s, 2H), 2.99 (t, 1H).
MS (ESI⁺) m/z 369.2 [M+H]⁺.

EXAMPLE 25

N[4]-[2-(1H-indol-3-yl)ethyl]-N[2]-(1H-indol-4-yl)pyrimidine-2,4-diamine

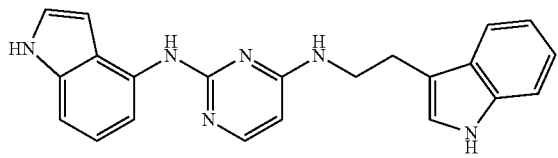 [SMILES: c1ccc2c(CCNc3ccnc(Nc4cccc5[nH]ccc45)n3)c[nH]c2c1]

$^1$H NMR (500 MHz, CDCl$_3$) δ 8.21 (s, 1H), 8.06 (s, 1H), 8.02 (d, 1H), 7.95 (d, 1H), 7.63 (d, 1H), 7.38 (d, 1H), 7.24-7.07 (m, 6H), 7.03 (s, 1H), 6.58 (s, 1H), 5.82 (d, 1H), 4.85 (br s, 1H), 3.72 (br s, 2H), 3.10 (t, 2H).

MS (ESI$^+$) m/z 369.2 [M+H]$^+$.

EXAMPLE 26

N[2]-[2-(1H-indol-3-yl)ethyl]-6-methyl-N[4]-(2-methyl-1H-indol-5-yl)pyrimidine-2,4-diamine

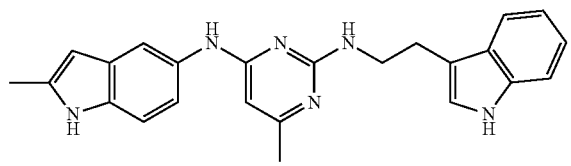 [SMILES: Cc1cc(Nc2ccc3[nH]c(C)cc3c2)nc(NCCc2c[nH]c3ccccc23)n1]

$^1$H NMR (500 MHz, DMSO-d$_6$, 75° C.) δ 10.61 (s, 1H), 10.55 (s, 1H), 8.35 (s, 1H), 7.59 (m, 2H), 7.35 (d, 1H), 7.18-7.13 (m, 2H), 7.09-7.06 (m, 2H), 6.96 (t, 1H), 6.12 (m, 1H), 5.97 (s, 1H), 5.78 (s, 1H), 3.59 (q, 2H), 2.97 (t, 2H), 2.36 (s, 3H), 2.08 (s, 3H). MS (ESI$^+$) m/z 397.4 [M+H]$^+$.

EXAMPLE 27

N[2]-[2-(5-methoxy-1H-indol-3-yl)ethyl]-6-methyl-N[4]-(2-methyl-1H-indol-5-yl)pyrimidine-2,4-diamine

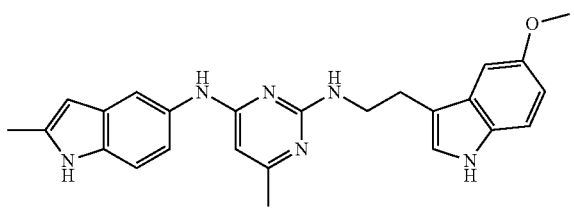

$^1$H NMR (500 MHz, DMSO-d$_6$, 75° C.) δ 10.55 (s, 1H), 10.45 (s, 1H), 8.35 (s, 1H), 7.61 (s, 1H), 7.23 (d, 1H), 7.15 (d, 1H), 7.11 (d, 1H), 7.08-7.06 (m, 2H), 6.72 (dd, 1H), 6.10 (m, 1H), 5.97 (s, 1H), 5.78 (s, 1H), 3.75 (s, 3H), 3.58 (q, 2H), 2.94 (t, 2H), 2.35 (s, 3H), 2.08 (s, 3H).

MS (ESI$^+$) m/z 427.3 [M+H]$^+$.

EXAMPLE 28

2-[2-(5-methoxy-1H-indol-3-yl)ethylamino]-6-(2-methyl-1H-indol-5-ylamino)pyrimidine-4-carboxamide

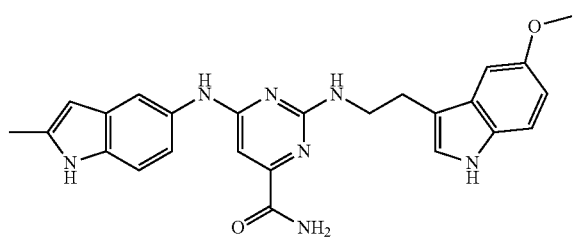

$^1$H NMR (500 MHz, DMSO-d$_6$, 75° C.) δ 10.60 (s, 1H), 10.46 (s, 1H), 8.88 (s, 1H), 7.68 (s, 1H), 7.56 (br s, 1H), 7.24 (m, 1H), 7.23 (d, 1H), 7.18 (d, 1H), 7.11 (m, 2H), 7.03 (s, 1H), 6.73 (d, 1H), 6.56 (s, 1H), 6.42 (m, 1H), 5.99 (br s, 1H), 3.74 (s, 3H), 3.34 (q, 2H), 2.97 (t, 2H), 2.36 (s, 3H).

MS (ESI$^+$) m/z 456.3 [M+H]$^+$.

EXAMPLE 29

N[2]-[2-(5-methoxy-1H-indol-3-yl)ethyl]-5-methyl-N[4]-(2-methyl-1H-indol-5-yl)pyrimidine-2,4-diamine

$^1$H NMR (500 MHz, DMSO-d$_6$, 75° C.) δ 10.51 (s, 1H), 10.41 (s, 1H), 7.75 (s, 1H), 7.66 (s, 1H), 7.63 (s, 1H), 7.25 (d, 1H), 7.22 (d, 1H), 7.13 (d, 1H), 7.04 (s, 2H), 6.71 (dd, 1H), 5.95 (m, 2H), 3.73 (s, 3H), 3.51 (q, 2H), 2.89 (t, 2H), 2.36 (s, 3H), 2.04 (s, 3H).

MS (ESI$^+$) m/z 427.3 [M+H]$^+$.

EXAMPLE 30

N²-[2-(5-methoxy-1H-indol-3-yl)ethyl]-N⁴-(2-methyl-1H-indol-5-yl)-6-(4-methylpiperazin-1-yl)pyrimidine-2,4-diamine

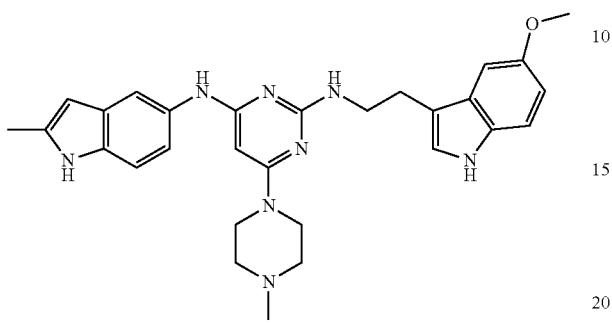

¹H NMR (500 MHz, DMSO-d$_6$, 75° C.) δ 10.51 (s, 1H), 10.44 (s, 1H), 7.94 (s, 1H), 7.53 (s, 1H), 7.23 (d, 1H), 7.13 (d, 1H), 7.10 (d, 1H), 7.05-7.02 (m, 2H), 6.72 (dd, 1H), 5.97 (s, 1H), 5.79 (t, 1H), 5.26 (s, 1H), 3.75 (s, 3H), 3.55 (q, 2H), 3.39 (t, 4H), 2.94 (t, 2H), 2.35 (s, 3H), 2.32 (t, 4H), 2.20 (s, 3H).
MS (ESI⁺) m/z 511.5 [M+H]⁺.

INTERMEDIATE 31

N-(1H-indol-5-yl)-2-chloropyrimidin-4-amine

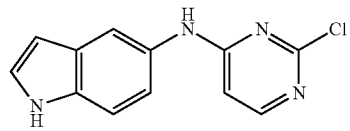 [SMILES: Clc1nccc(Nc2ccc3[nH]ccc3c2)n1]

¹H NMR (500 MHz, DMSO-d$_6$) δ 11.12 (s, 1H), 9.81 (s, 1H), 8.04 (d, 1H), 7.67 (br s, 1H), 7.40 (d, 1H), 7.36 (t, 1H), 7.11 (br s, 1H), 6.61 (br s, 1H), 6.42 (s, 1H).
MS (ESI⁺) m/z 245.3 [M+H]⁺.

INTERMEDIATE 32

N-(2-methyl-1H-indol-5-yl)-2-chloropyrimidin-4-amine

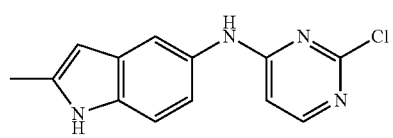

¹H-NMR (500 MHz, DMSO-d$_6$, 75° C.) δ 10.76 (s, 1H), 9.54 (s, 1H), 8.01 (d, 1H), 7.47 (s, 1H), 7.26 (d, 1H), 7.01 (d, 1H), 6.56 (d, 1H), 6.11 (s, 1H), 2.39 (s, 3H).
MS (ESI⁺) m/z 259.1 [M+H]⁺.

INTERMEDIATE 33

N-(2-chloropyrimidin-4-yl)-1,2-dimethyl-1H-indol-5-amine

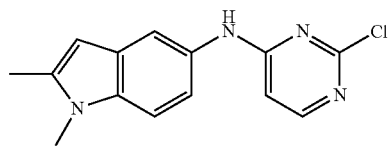 [SMILES: Cc1cc2cc(Nc3ccnc(Cl)n3)ccc2n1C]

¹H-NMR (500 MHz, DMSO-d$_6$, 75° C.) δ 9.57 (s, 1H), 8.02 (d, 1H), 7.51 (s, 1H), 7.35 (d, 1H), 7.10 (d, 1H), 6.58 (d, 1H), 6.20 (s, 1H), 3.66 (s, 3H), 2.41 (s, 3H).
MS (ESI⁺) m/z 273.1 [M+H]⁺.

INTERMEDIATE 34

N-(2-chloropyrimidin-4-yl)-2,3-dimethyl-1H-indol-5-amine

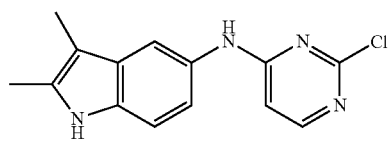 [SMILES: Cc1[nH]c2ccc(Nc3ccnc(Cl)n3)cc2c1C]

¹H-NMR (500 MHz, DMSO-d$_6$, 75° C.) δ 10.52 (s, 1H), 9.55 (s, 1H), 8.01 (d, 1H), 7.42 (s, 1H), 7.23 (d, 1H), 7.02 (d, 1H), 6.56 (d, 1H), 2.32 (s, 3H), 2.14 (s, 3H).
MS (ESI⁺) m/z 273.2 [M+H]⁺.

INTERMEDIATE 35

[5-(2-chloropyrimidin-4-ylamino)-1H-indol-2-yl]methanol

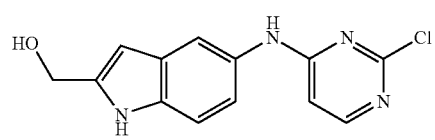 [SMILES: OCc1cc2cc(Nc3ccnc(Cl)n3)ccc2[nH]1]

¹H-NMR (500 MHz, DMSO-d₆, 75° C.) δ 10.84 (s, 1H), 9.56 (s, 1H), 8.02 (d, 1H), 7.55 (s, 1H), 7.34 (d, 1H), 7.07 (dd, 1H), 6.58 (d, 1H), 6.27 (s, 1H), 5.01 (m, 1H), 4.62 (d, 2H).

INTERMEDIATE 36 methyl 5-(2-chloropyrimidin-4-ylamino)-1H-indole-2-carboxylate

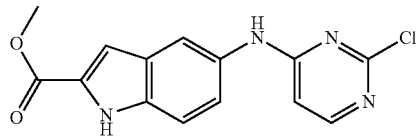 [SMILES: COC(=O)c1cc2cc(Nc3ccnc(Cl)n3)ccc2[nH]1]

¹H-NMR (500 MHz, DMSO-d₆, 75° C.) δ 11.76 (s, 1H), 9.70 (s, 1H), 8.07 (d, 1H), 7.80 (s, 1H), 7.47 (d, 1H), 7.32 (dd, 1H), 7.14 (s, 1H), 6.65 (d, 1H), 3.89 (s, 3H).

MS (ESI⁺) m/z 303.1 [M+H]⁺.

INTERMEDIATE 37

N-(2-chloropyrimidin-4-yl)-1H-benzo[d]imidazol-5-amine

¹H NMR (500 MHz, DMSO-d₆) δ 12.38 (br s, 1H), 10.00 (br s, 1H), 8.19 (s, 1H), 8.10 (d, 1H), 7.94 (br s, 1H), 7.58 (d, 1H), 7.22 (d, 1H), 6.71 (d, 1H).

MS (ESI⁺) m/z 246.1 [M+H]⁺.

INTERMEDIATE 38

N-(2-chloropyrimidin-4-yl)-2-methyl-1H-benzo[d]imidazol-5-amine

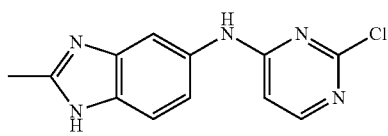 [SMILES: Cc1nc2cc(Nc3ccnc(Cl)n3)ccc2[nH]1]

¹H-NMR (500 MHz, DMSO-d₆, 75° C.) δ 12.01 (s, 1H), 9.72 (m, 1H), 8.07 (s, 1H), 7.72 (m, 1H), 7.46-7.36 (m, 1H), 7.18-7.11 (m, 1H), 6.66 (m, 1H), 2.48 (s, 3H).

MS (ESI⁺) m/z 260.1 [M+H]⁺.

INTERMEDIATE 39

N-(2-chloropyrimidin-4-yl)-1H-indol-6-amine

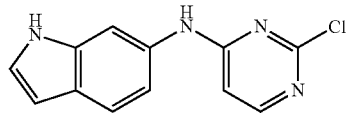 [SMILES: Clc1nccc(Nc2ccc3cc[nH]c3c2)n1]

¹H-NMR (500 MHz, DMSO-d₆) δ 11.13 (s, 1H), 9.95 (s, 1H), 8.08 (d, 1H), 7.77 (br s, 1H), 7.50 (d, 1H), 7.31 (s, 1H), 7.03 (d, 1H), 6.71 (d, 1H), 6.39 (d, 1H).

MS (ESI⁺) m/z 245.1 [M+H]⁺.

INTERMEDIATE 40

N-(2-chloropyrimidin-4-yl)-1H-indol-4-amine

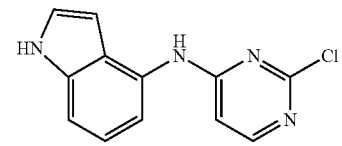 [SMILES: Clc1nccc(Nc2cccc3[nH]ccc23)n1]

¹H-NMR (500 MHz, DMSO-d₆, 75° C.) δ 11.06 (br s, 1H), 9.64 (s, 1H), 8.08 (d, 1H), 7.31 (t, 1H), 7.29-7.25 (m, 2H), 7.10 (t, 1H), 6.67 (d, 1H), 6.48 (s, 1H).

MS (ESI⁺) m/z 245.1 [M+H]⁺.

INTERMEDIATE 41

N-[2-(1H-indol-3-yl)ethyl]-2-chloropyrimidin-4-amine

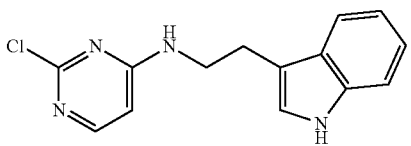 [SMILES: Clc1nccc(NCCc2c[nH]c3ccccc23)n1]

¹H-NMR (500 MHz, DMSO-d₆, 75° C.) δ 10.66 (s, 1H), 7.90 (d, 1H), 7.79 (br s, 1H), 7.59 (d, 1H), 7.35 (d, 1H), 7.15 (s, 1H), 7.07 (t, 1H), 6.99 (t, 1H), 6.44 (d, 1H), 3.56 (m, 2H), 2.96 (t, 2H).

MS (ESI⁺) m/z 273.2 [M+H]⁺.

INTERMEDIATE 42

2-chloro-N-[2-(5-methoxy-1H-indol-3-yl)ethyl]pyrimidin-4-amine

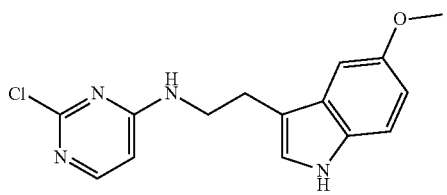 [SMILES: COc1ccc2[nH]cc(CCNc3ccnc(Cl)n3)c2c1]

¹H-NMR (500 MHz, DMSO-d₆, 75° C.) δ 10.50 (s, 1H), 7.90 (d, 1H), 7.79 (br s, 1H), 7.24 (d, 1H), 7.11 (s, 1H), 7.04 (s, 1H), 6.73 (dd, 1H), 6.45 (d, 1H) 3.78 (s, 3H), 3.56 (br s, 2H), 2.93 (t, 2H).
MS (ESI⁺) m/z 303.1 [M+H]⁺.

INTERMEDIATE 43

N-(2-methyl-1H-indol-5-yl)-2-chloro-6-methylpyrimidin-4-amine

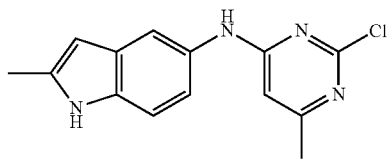 [SMILES: Cc1cc(Nc2ccc3[nH]c(C)cc3c2)nc(Cl)n1]

¹H NMR (500 MHz, CD₃OD) δ 7.43 (br s, 1H), 7.26 (d, 1H), 6.98 (br s, 1H), 6.34 (s, 1H), 6.02 (s, 1H), 2.41 (s, 3H), 2.22 (s, 3H).
MS (ESI⁺) m/z 273.2 [M+H]⁺.

INTERMEDIATE 44

2-chloro-6-(2-methyl-1H-indol-5-ylamino)pyrimidine-4-carboxamide

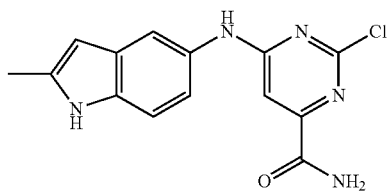 [SMILES: Cc1cc2cc(Nc3cc(C(N)=O)nc(Cl)n3)ccc2[nH]1]

¹H-NMR (500 MHz, DMSO-d₆, 105° C.) δ 10.68 (s, 1H), 9.76 (s, 1H), 7.50 (m, 3H), 7.29 (d, 1H), 7.15 (s, 1H), 7.05 (d, 1H), 6.13 (s, 1H), 2.36 (s, 3H).
MS (ESI⁺) m/z 302.1 [M+H]⁺.

INTERMEDIATE 45

N-(2-chloro-5-methylpyrimidin-4-yl)-2-methyl-1H-indol-5-amine

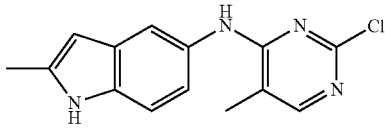 [SMILES: Cc1cc2cc(Nc3nc(Cl)ncc3C)ccc2[nH]1]

¹H-NMR (500 MHz, DMSO-d₆, 75° C.) δ 10.71 (s, 1H), 8.56 (s, 1H), 7.92 (s, 1H), 7.52 (d, 1H), 7.24 (d, 1H), 7.12 (dd, 1H), 6.11 (s, 1H), 2.39 (s, 3H), 2.15 (s, 3H).
MS (ESI⁺) m/z 273.1 [M+H]⁺.

INTERMEDIATE 46

4-chloro-N-[2-(5-methoxy-1H-indol-3-yl)ethyl]-6-(4-methylpiperazin-1-yl)pyrimidin-2-amine

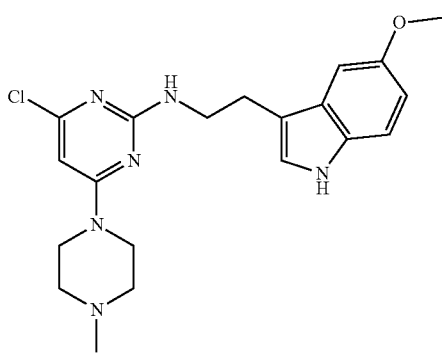 [SMILES: COc1ccc2[nH]cc(CCNc3nc(Cl)cc(N4CCN(C)CC4)n3)c2c1]

¹H-NMR (500 MHz, DMSO-d₆) δ 10.62 (s, 1H), 7.22 (d, 1H), 7.13-6.96 (m, 3H), 6.71 (dd, 1H), 6.06 (br s, 1H), 3.75 (s, 3H), 3.55 (br s, 4H), 3.46 (q, 2H), 2.87 (t, 2H), 2.31 (t, 4H), 2.19 (m, 3H).
MS (ESI⁺) m/z 401.2 [M+H]⁺.

EXAMPLE 47

N²-[2-(4-methoxy-1H-indol-3-yl)ethyl]-N⁴-(2-methyl-1H-indol-5-yl)pyrimidine-2,4-diamine

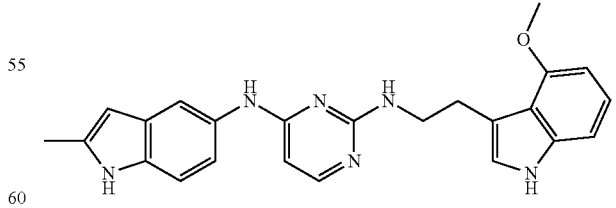

¹H NMR (500 MHz, DMSO-d₆, 105° C.) δ 10.51 (br s, 1H), 10.48 (br s, 1H), 8.37 (s, 1H), 7.75 (d, 1H), 7.63 (d, 1H), 7.16 (d, 1H), 7.06 (dd, 1H), 6.98-6.94 (m, 3H), 6.45 (dd, 1H), 5.98 (br s, 2H), 5.89 (d, 1H), 3.86 (s, 3H), 3.59 (q, 2H), 3.11 (t, 2H), 2.36 (s, 3H).
MS (ESI⁺) m/z 413.4 [M+H]⁺.

EXAMPLE 48

N$^4$-(2-methyl-1H-indol-5-yl)-N$^2$-[2-(5-propoxy-1H-indol-3-yl)ethyl]pyrimidine-2,4-diamine

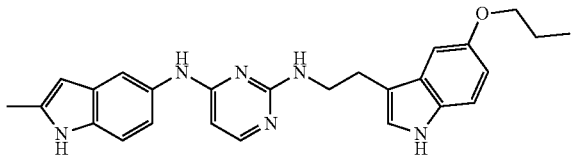 [SMILES: CCCOc1ccc2[nH]cc(CCNc3nccc(Nc4ccc5[nH]c(C)cc5c4)n3)c2c1]

$^1$H NMR (500 MHz, DMSO-d$_6$, 75° C.) δ 10.56 (s, 1H), 10.43 (s, 1H), 8.50 (s, 1H), 7.78 (d, 1H), 7.65 (s, 1H), 7.22 (d, 1H), 7.12 (d, 1H), 7.07 (m, 3H), 6.71 (dd, 1H), 6.18 (m, 1H), 5.97 (s, 1H), 5.91 (d, 1H), 3.91 (t, 2H), 3.56 (q, 2H), 2.94 (t, 2H), 2.36 (s, 3H), 1.71 (dt, 2H), 0.98 (t, 3H).
MS (ESI$^+$) m/z 441.2 [M+H]$^+$.

EXAMPLE 49

N$^2$-[2-(5-isopropoxy-1H-indol-3-yl)ethyl]-N$^4$-(2-methyl-1H-indol-5-yl)pyrimidine-2,4-diamine

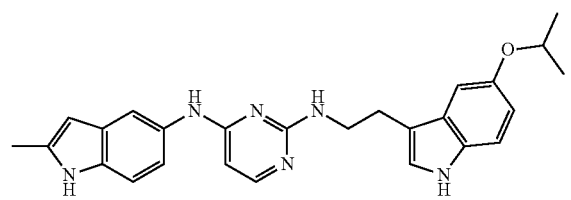 [SMILES: Cc1cc2cc(Nc3ccnc(NCCc4c[nH]c5ccc(OC(C)C)cc45)n3)ccc2[nH]1]

$^1$H NMR (500 MHz, DMSO-d$_6$, 75° C.) δ 10.56 (s, 1H), 10.43 (s, 1H), 8.49 (s, 1H), 7.77 (d, 1H), 7.65 (s, 1H), 7.21 (d, 1H), 7.12 (d, 1H), 7.08 (m, 3H), 6.70 (dd, 1H), 6.19 (m, 1H), 5.98 (s, 1H), 5.91 d, 1H), 4.46 (dq, 1H), 3.56 (q, 2H), 2.93 (t, 2H), 2.49 (s, 3H), 1.25 (d, 6H).
MS (ESI$^+$) m/z 441.2 [M+H]$^+$.

EXAMPLE 50

N$^2$-[2-(5,6-dimethoxy-1H-indol-3-yl)ethyl]-N$^4$-(2-methyl-1H-indol-5-yl)pyrimidine-2,4-diamine

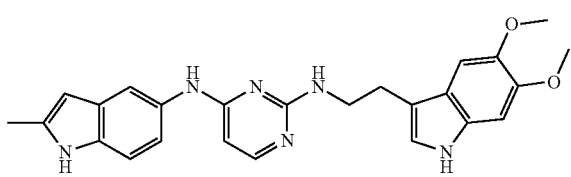

$^1$H NMR (500 MHz, DMSO-d$_6$, 75° C.) δ 10.56 (s, 1H), 10.29 (s, 1H), 8.53 (s, 1H), 7.77 (d, 1H), 7.65 (s, 1H), 7.16 (d, 1H), 7.09 (d, 1H), 7.08 (s, 1H), 6.97 (d, 1H), 6.91 (s, 1H), 6.20 (br s, 1H), 5.97 (s, 1H), 5.92 (d, 1H), 3.77 (s, 3H), 3.74 (s, 3H), 3.57 (q, 2H), 2.92 (t, 2H), 2.36 (s, 3H).
MS (ESI$^+$) m/z 443.2 [M+H]$^+$.

EXAMPLE 51

N$^2$-[2-(5-methoxy-7-methyl-1H-indol-3-yl)ethyl]-N$^4$-(2-methyl-1H-indol-5-yl)pyrimidine-2,4-diamine

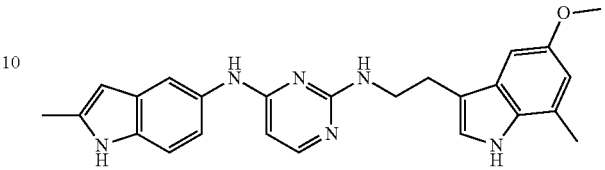

$^1$H NMR (500 MHz, DMSO-d$_6$, 75° C.) δ 10.56 (s, 1H), 10.41 (s, 1H), 8.50 (s, 1H), 7.77 (d, 1H), 7.65 (s, 1H), 7.15 (d, 1H), 7.09-7.07 (m, 2H), 6.90 (s, 1H), 6.55 (s, 1H), 6.17 (m, 1H), 5.96 (s, 1H), 5.91 (d, 1H), 3.73 (s, 3H), 3.57 (q, 2H), 2.93 (t, 2H), 2.41 (s, 3H), 2.36 (s, 3H).
MS (ESI$^+$) m/z 427.5 [M+H]$^+$.

EXAMPLE 52

N$^2$-[2-(5-methoxy-1H-indol-3-yl)ethyl]-N$^4$-(1-methyl-1H-benzo[d]imidazol-5-yl)pyrimidine-2,4-diamine

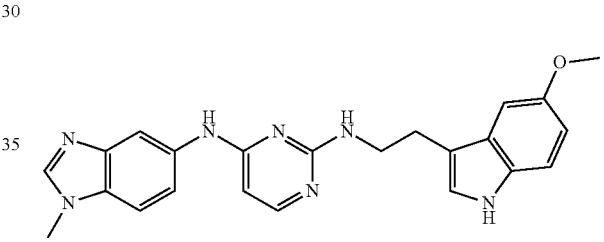

$^1$H NMR (500 MHz, DMSO-d$_6$, 75° C.) δ 10.44 (s, 1H), 8.81 (s, 1H), 8.05 (s, 1H), 8.02 (d, 1H), 7.83 (d, 1H), 7.46 (dd, 1H), 7.39 (d, 1H), 7.22 (d, 1H), 7.15 (d, 1H), 7.07 (d, 1H), 6.72 (dd, 1H), 6.34 (br s, 1H), 5.99 (d, 1H), 3.81 (s, 3H), 3.74 (s, 3H), 3.58 (q, 2H), 2.95 (t, 2H).
MS (ESI$^+$) m/z 414.4 [M+H]$^+$.

EXAMPLE 53

N$^4$-(1,2-dimethyl-1H-benzo[d]imidazol-5-yl)-N$^2$-[2-(5-methoxy-1H-indol-3-yl)ethyl]pyrimidine-2,4-diamine

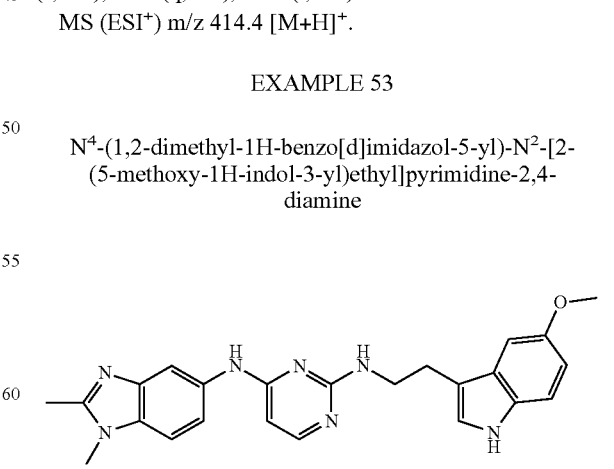

$^1$H NMR (500 MHz, DMSO-d$_6$, 75° C.) δ 10.44 (s, 1H), 8.74 (s, 1H), 7.88 (d, 1H), 7.80 (d, 1H), 7.37 (dd, 1H), 7.28 (d, 1H), 7.23 (d, 1H), 7.17 (d, 1H), 7.07 (d, 1H), 6.72 (dd, 1H), 6.30 (br s, 1H), 5.96 (d, 1H), 3.75 (s, 3H), 3.69 (s, 3H), 3.57 (q, 2H), 2.95 (t, 2H), 2.51 (s, 3H).
MS (ESI+) m/z 428.2 [M+H]+.

EXAMPLE 54

N²-[2-(5-methoxy-1H-indol-3-yl)ethyl]-N⁴-(1-methyl-1H-indol-4-yl)pyrimidine-2,4-diamine

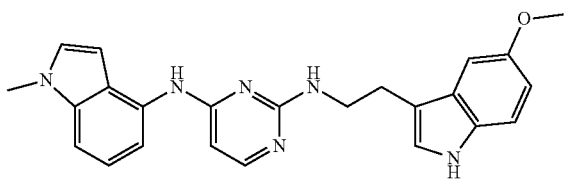

¹H NMR (500 MHz, DMSO-d₆, 75° C.) δ 10.45 (s, 1H), 8.55 (s, 1H), 7.86 (d, 1H), 7.72 (d, 1H), 7.25-7.20 (m, 2H), 7.12-7.02 (m, 4H), 6.72 (dd, 1H), 6.64 (d, 1H), 6.31 (br s, 1H), 6.14 (d, 1H), 3.77 (s, 3H), 3.75 (s, 3H), 3.58 (q, 2H), 2.94 (t, 2H).
MS (ESI+) m/z 413.4 [M+H]+.

EXAMPLE 55

N²-[2-(5-ethoxy-1H-indol-3-yl)ethyl]-6-methyl-N⁴-(2-methyl-1H-indol-5-yl)pyrimidine-2,4-diamine

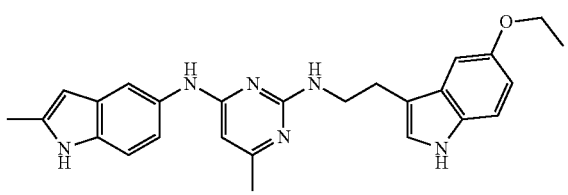 [SMILES: CCOc1ccc2[nH]cc(CCNc3nc(C)cc(Nc4ccc5[nH]c(C)cc5c4)n3)c2c1]

¹H NMR (500 MHz, DMSO-d₆, 75° C.) δ 10.56 (s, 1H), 10.44 (s, 1H), 8.44 (s, 1H), 7.61 (s, 1H), 7.22 (d, 1H), 7.16 (d, 1H), 7.11-7.05 (m, 3H), 6.72 (dd, 1H), 6.16 (br s, 1H), 5.97 (s, 1H), 5.80 (s, 1H), 4.00 (q, 2H), 3.57 (q, 2H), 2.94 (t, 2H), 2.36 (s, 3H), 2.09 (s, 3H), 1.31 (t, 3H).
MS (ESI+) m/z 441.4 [M+H]+.

EXAMPLE 56

N²-[2-(5-methoxy-2-methyl-1H-indol-3-yl)ethyl]-6-methyl-N⁴-(2-methyl-1H-indol-5-yl)pyrimidine-2,4-diamine

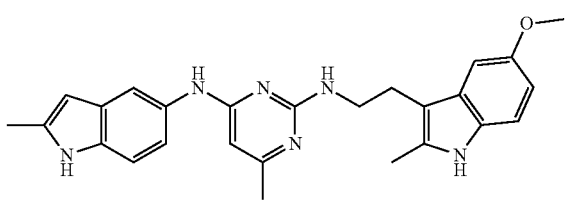

¹H NMR (500 MHz, DMSO-d₆, 75° C.) δ 10.59 (s, 1H), 10.32 (s, 1H), 8.54 (br s, 1H), 7.59 (s, 1H), 7.17 (d, 1H), 7.11 (d, 1H), 7.08 (dd, 1H), 6.98 (d, 1H), 6.62 (dd, 1H), 6.16 (br s, 1H), 6.00 (s, 1H), 5.81 (s, 1H), 3.73 (s, 3H), 3.46 (q, 2H), 2.88 (t, 2H), 2.36 (s, 3H), 2.29 (s, 3H), 2.10 (s, 3H).
MS (ESI+) m/z 441.3 [M+H]+.

EXAMPLE 57

N²-[2-(5-methoxy-1H-indol-3-yl)ethyl]-6-methyl-N⁴-(2-methyl-1H-benzo[d]imidazol-5-yl)pyrimidine-2,4-diamine

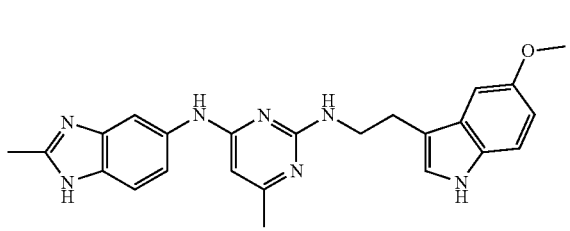

¹H NMR (500 MHz, CD₃OD) δ 7.94 (br s, 1H), 7.35 (m, 1H), 7.25 (br s, 1H), 7.21 (d, 1H), 7.04 (s, 1H), 6.99 (d, 1H), 6.72 (dd, 1H), 5.87 (s, 1H), 3.73-3.69 (m, 5H), 3.03 (t, 2H), 2.51 (s, 3H), 2.13 (s, 3H).
MS (ESI+) m/z 428.2 [M+H]+.

EXAMPLE 58

N²-[2-(5-ethoxy-1H-indol-3-yl)ethyl]-6-methyl-N⁴-(2-methyl-1H-benzo[d]imidazol-5-yl)pyrimidine-2,4-diamine

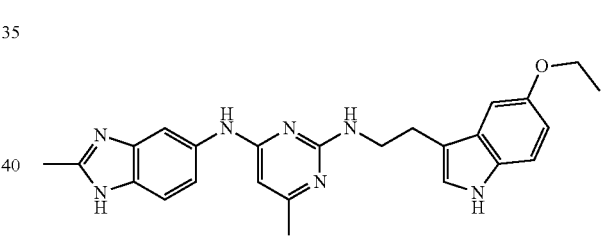

¹H NMR (500 MHz, CD₃OD) δ 7.96 (br s, 1H), 7.35 (m, 1H), 7.25 (br s, 1H), 7.20 (d, 1H), 7.03 (s, 1H), 6.98 (d, 1H), 6.72 (dd, 1H), 5.87 (s, 1H), 3.89 (m, 2H), 3.71 (t, 2H), 3.03 (t, 2H), 2.51 (s, 3H), 2.13 (s, 3H), 1.30 (t, 3H).
MS (ESI+) m/z 442.2 [M+H]+.

EXAMPLE 59

[5-(2-{[2-(5-methoxy-1H-indol-3-yl)ethyl][methyl]amino}pyrimidin-4-ylamino)-1H-indol-2-yl]methanol

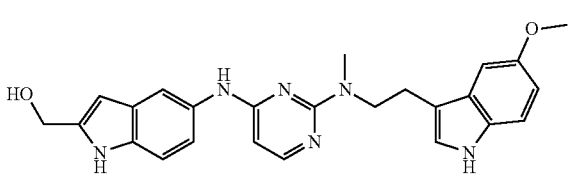 [SMILES: COc1ccc2[nH]cc(CCN(C)c3nccc(Nc4ccc5[nH]c(CO)cc5c4)n3)c2c1]

¹H NMR (500 MHz, DMSO-d₆, 75° C.) δ 10.63 (s, 1H), 10.43 (s, 1H), 8.60 (s, 1H), 7.87 (d, 1H), 7.75 (d, 1H), 7.25-

7.20 (m, 2H), 7.17 (dd, 1H), 7.09 (d, 1H), 7.06 (d, 1H), 6.72 (dd, 1H), 6.11 (s, 1H), 5.94 (d, 1H), 4.94 (t, 1H), 4.58 (d, 2H), 3.86 (m, 2H), 3.75 (s, 3H), 3.08 (s, 3H), 2.97 (t, 2H).
MS (ESI⁺) m/z 443.4 [M+H]⁺.

EXAMPLE 60

(5-{2-[2-(5-methoxy-1H-indol-3-yl)ethylamino]pyrimidin-4-ylamino}-1-methyl-1H-benzo[d]imidazol-2-yl)methanol

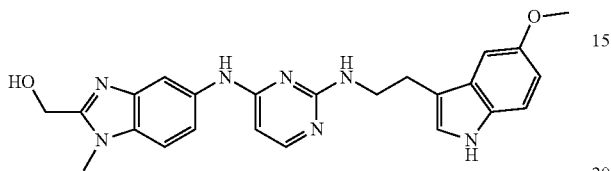

¹H NMR (500 MHz, DMSO-d₆, 75° C.) δ 10.44 (s, 1H), 8.80 (s, 1H), 7.97 (d, 1H), 7.82 (d, 1H), 7.43 (dd, 1H), 7.34 (d, 1H), 7.23 (d, 1H), 7.17 (d, 1H), 7.07 (d, 1H), 6.72 (dd, 1H), 6.32 (br s, 1H), 5.97 (d, 1H), 5.32 (t, 1H), 4.72 (d, 2H), 3.80 (s, 3H), 3.75 (s, 3H), 3.58 (q, 2H), 2.97 (t, 2H).
MS (ESI⁺) m/z 444.2 [M+H]⁺.

EXAMPLE 61

N²-[2-(5-methoxy-1H-indol-3-yl)ethyl]-N⁴-methyl-N⁴-(2-methyl-1H-indol-5-yl)pyrimidine-2,4-diamine

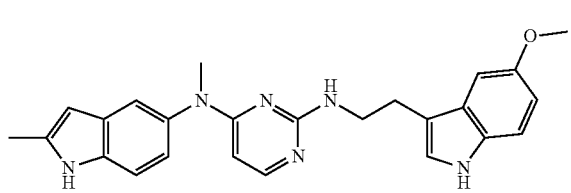

¹H NMR (500 MHz, DMSO-d₆, 75° C.) δ 10.85 (s, 1H), 10.45 (s, 1H), 7.60 (d, 1H), 7.32 (d, 1H), 7.26 (s, 1H), 7.23 (d, 1H), 7.12-7.07 (m, 2H), 6.85 (dd, 1H), 6.72 (dd, 1H), 6.26 (br s, 1H), 6.14 (s, 1H), 5.41 (d, 1H), 3.77 (s, 3H), 3.58 (q, 2H), 3.39 (s, 3H), 2.95 (t, 2H), 2.40 (s, 3H).
MS (ESI⁺) m/z 427.4 [M+H]⁺.

EXAMPLE 62

N⁴-(1,2-dimethyl-1H-indol-5-yl)-N²-[2-(5-methoxy-1H-indol-3-yl)ethyl]-N⁴-methylpyrimidine-2,4-diamine

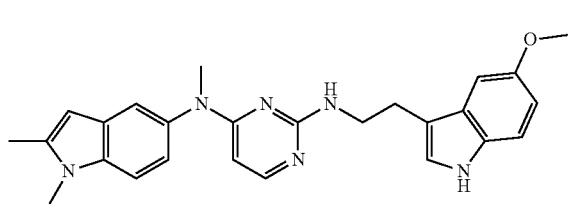

¹H NMR (500 MHz, DMSO-d₆, 75° C.) δ 10.51 (s, 1H), 7.59 (d, 1H), 7.45 (d, 1H), 7.34 (d, 1H), 7.25 (d, 1H), 7.12 (d, 1H), 7.11 (br s, 1H), 7.07 (d, 1H), 6.96 (dd, 1H), 6.74 (dd, 1H), 6.26 (s, 1H), 5.52 (d, 1H), 3.77 (s, 3H), 3.70 (s, 3H), 3.64 (q, 2H), 3.45 (s, 3H), 2.98 (t, 2H), 2.43 (s, 3H).
MS (ESI⁺) m/z 441.4 [M+H]⁺.

INTERMEDIATE 63

N-(2-chloropyrimidin-4-yl)-1-methyl-1H-benzo[d]imidazol-5-amine

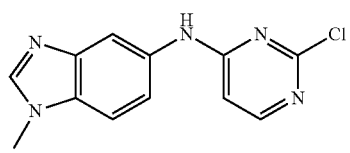 [SMILES: Cn1cnc2cc(Nc3ccnc(Cl)n3)ccc21]

¹H NMR (500 MHz, DMSO-d₆, 75° C.) δ 9.77 (br s, 1H), 8.13 (s, 1H), 8.09 (d, 1H), 7.87 (s, 1H), 7.54 (d, 1H), 7.34 (d, 1H), 6.68 (d, 1H), 3.84 (s, 3H).

INTERMEDIATE 64

N-(2-chloropyrimidin-4-yl)-1,2-dimethyl-1H-benzo[d]imidazol-5-amine

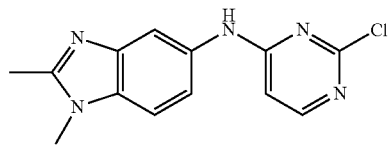 [SMILES: Cc1nc2cc(Nc3ccnc(Cl)n3)ccc2n1C]

¹H NMR (500 MHz, DMSO-d₆, 75° C.) δ 9.71 (s, 1H), 8.07 (d, 1H), 7.72 (s, 1H), 7.43 (d, 1H), 7.25 (dd, 1H), 6.65 (d, 1H), 3.73 (s, 3H), 2.52 (s, 3H).
MS (ESI⁺) m/z 274.2 [M+H]⁺.

INTERMEDIATE 65

N-(2-chloropyrimidin-4-yl)-1-methyl-1H-indol-4-amine

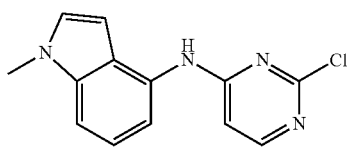 [SMILES: Cn1ccc2c(Nc3ccnc(Cl)n3)cccc21]

¹H NMR (500 MHz, DMSO-d₆, 75° C.) δ 9.66 (s, 1H), 8.09 (d, 1H), 7.34-7.28 (m, 3H), 7.17 (dd, 1H), 6.68 (d, 1H), 6.48 (d, 1H), 3.81 (s, 3H).
MS (ESI⁺) m/z 259.2 [M+H]⁺.

INTERMEDIATE 66

N-(2-chloro-6-methylpyrimidin-4-yl)-2-methyl-1H-benzo[d]imidazol-5-amine

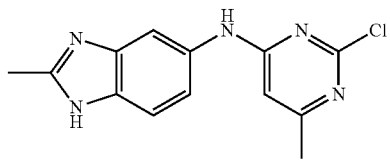 [SMILES: Cc1cc(Nc2ccc3[nH]c(C)nc3c2)nc(Cl)n1]

$^1$H NMR (500 MHz, DMSO-d$_6$, 75° C.) δ 12.00 (s, 1H), 9.60-9.52 (m, 1H), 7.70-7.65 (m, 1H), 7.46-7.36 (m, 1H), 7.16-7.10 (m, 1H), 6.52-6.47 (m, 1H), 2.47 (s, 3H), 2.25 (s, 3H).

MS (ESI$^+$) m/z 274.2 [M+H]$^+$.

INTERMEDIATE 67

2-[(tert-butyldimethylsilyloxy)methyl]-N-(2-chloro-pyrimidin-4-yl)-1H-indol-5-amine

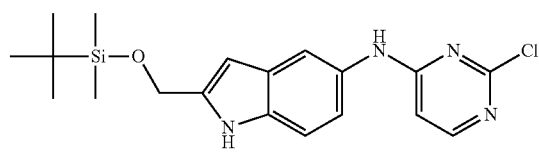 [SMILES: CC(C)(C)[Si](C)(C)OCc1cc2cc(Nc3ccnc(Cl)n3)ccc2[nH]1]

$^1$H-NMR (500 MHz, DMSO-d$_6$, 75° C.) δ 10.86 (s, 1H), 9.57 (s, 1H), 8.02 (d, 1H), 7.57 (s, 1H), 7.36 (d, 1H), 7.09 (dd, 1H), 6.59 (d, 1H), 6.31 (s, 1H), 4.80 (s, 2H), 0.92 (s, 9H), 0.10 (s, 6H).

MS (ESI$^+$) m/z 389.2 [M+H]$^+$.

INTERMEDIATE 68

[5-(2-chloropyrimidin-4-ylamino)-1-methyl-1H-benzo[d]imidazol-2-yl]methanol

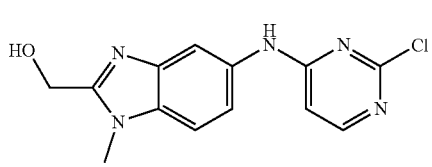 [SMILES: Cn1c(CO)nc2cc(Nc3ccnc(Cl)n3)ccc21]

$^1$H-NMR (500 MHz, DMSO-d$_6$, 75° C.) δ 9.75 (s, 1H), 8.08 (d, 1H), 7.81 (s, 1H), 7.50 (d, 1H), 7.32 (dd, 1H), 6.66 (d, 1H), 5.35 (m, 1H), 4.73 (d, 2H), 3.83 (s, 3H).

MS (ESI$^+$) m/z 290.2 [M+H]$^+$.

INTERMEDIATE 69

2-[(tert-butyldimethylsilyloxy)methyl]-N-(2-chloro-pyrimidin-4-yl)-1-methyl-1H-benzo[d]imidazol-5-amine

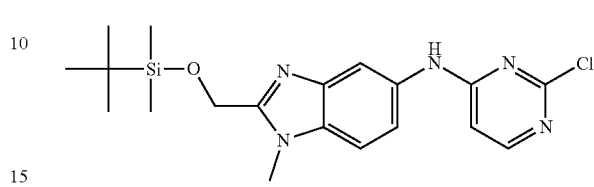

$^1$H-NMR (500 MHz, DMSO-d$_6$, 75° C.) δ 8.08 (d, 1H), 7.96 (s, 1H), 7.84 (s, 1H), 7.52 (d, 1H), 7.33 (dd, 1H), 6.67 (d, 1H), 4.93 (s, 2H), 3.83 (s, 3H), 0.90 (s, 9H), 0.10 (s, 6H).

INTERMEDIATE 70

N-(2-chloropyrimidin-4-yl)-N,2-dimethyl-1H-indol-5-amine

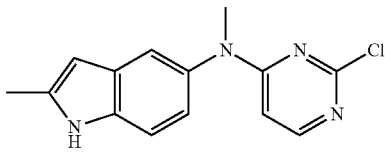 [SMILES: Cc1cc2cc(N(C)c3ccnc(Cl)n3)ccc2[nH]1]

$^1$H-NMR (500 MHz, DMSO-d$_6$) δ 11.14 (s, 1H), 7.86 (d, 1H), 7.37 (d, 1H), 7.34 (s, 1H), 6.89 (dd, 1H), 6.16 (s, 1H), 6.07 (br s, 1H), 3.39 (s, 3H).

MS (ESI$^+$) m/z 273.2 [M+H]$^+$.

INTERMEDIATE 71

N-(2-chloropyrimidin-4-yl)-N,1,2-trimethyl-1H-indol-5-amine

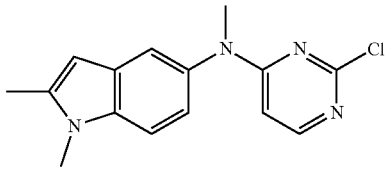 [SMILES: Cc1cc2cc(N(C)c3ccnc(Cl)n3)ccc2n1C]

$^1$H-NMR (500 MHz, DMSO-d$_6$, 25° C.) δ 7.86 (d, 1H), 7.50 (d, 1H), 7.38 (s, 1H), 6.98 (dd, 1H), 6.26 (s, 1H), 6.06 (br s, 1H), 3.69 (s, 3H), 3.40 (s, 3H).

MS (ESI$^+$) m/z 287.2 [M+H]$^+$.

EXAMPLE 72

[5-({2-[2-(5-ethoxy-1H-indol-3-yl)ethylamino]pyrimidin-4-yl}amino)-1H-indol-2-yl]methanol

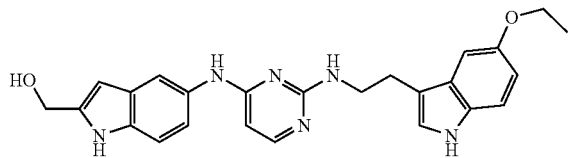 [SMILES: CCOc1ccc2[nH]cc(CCNc3nccc(Nc4ccc5[nH]c(CO)cc5c4)n3)c2c1]

¹H NMR (400 MHz, DMSO-d₆, 75° C.) δ 10.62 (s, 1H), 10.40 (s, 1H), 8.49 (s, 1H), 7.78 (d, 1H), 7.71 (s, 1H), 7.25-7.22 (m, 2H), 7.15 (m, 1H), 7.08 (m, 2H), 6.72 (dd, 1H), 6.16-6.24 (m, 2H), 5.93 (d, 1H), 4.91 (m, 1H), 4.60 (d, 2H), 4.02 (q, 2H), 3.58 (q, 2H), 2.95 (t, 2H), 1.32 (t, 3H).

MS (ESI⁺) m/z 443.2 [M+H]⁺.

EXAMPLE 73

$N^2$-[2-(5-methoxy-1H-indol-3-yl)ethyl]-$N^4$-(2-methyl-1H-indol-6-yl)pyrimidine-2,4-diamine

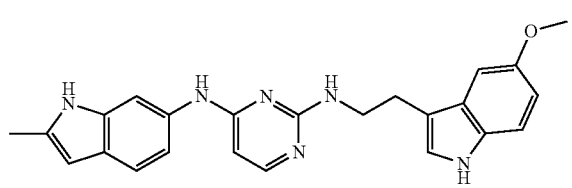

¹H NMR (400 MHz, DMSO-d₆, 75° C.) δ 10.40 (d, 2H), 8.59 (s, 1H), 7.80 (d, 1H), 7.55 (s, 1H), 7.25 (t, 2H), 7.10 (td, 3H), 6.73 (dd, 1H), 6.10 (t, 1H), 6.03 (s, 1H), 5.97 (d, 1H), 3.75 (s, 3H), 3.61 (q, 2H), 2.96 (t, 2H), 2.36 (s, 3H).

MS (ESI⁺) m/z 413.2 [M+H]⁺.

EXAMPLE 74

$N^2$-[2-(5-ethoxy-1H-indol-3-yl)ethyl]-$N^4$-(2-methyl-1H-indol-6-yl)pyrimidine-2,4-diamine

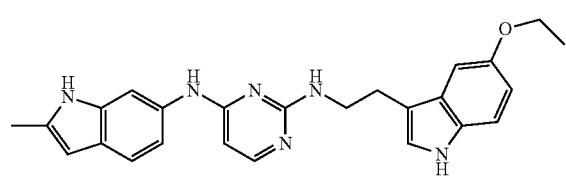 [SMILES: CCOc1ccc2[nH]cc(CCNc3nccc(Nc4ccc5cc(C)[nH]c5c4)n3)c2c1]

¹H NMR (400 MHz, DMSO-d₆, 75° C.) δ 10.40 (d, 2H), 8.59 (s, 1H), 7.80 (d, 1H), 7.56 (s, 1H), 7.26 (d, 1H), 7.27 (d, 1H), 7.13-7.06 (m, 3H), 6.72 (dd, 1H), 6.10 (t, 1H), 6.03 (s, 1H), 5.97 (d, 1H), 4.01 (q, 2H), 3.60 (q, 2H), 2.95 (t, 2H), 2.36 (s, 3H), 1.32 (t, 3H).

MS (ESI⁺) m/z 427.2 [M+H]⁺.

EXAMPLE 75

$N^2$-[2-(5-methoxy-1H-indol-3-yl)ethyl]-$N^4$-(1-methylindol-6-yl)pyrimidine-2,4-diamine

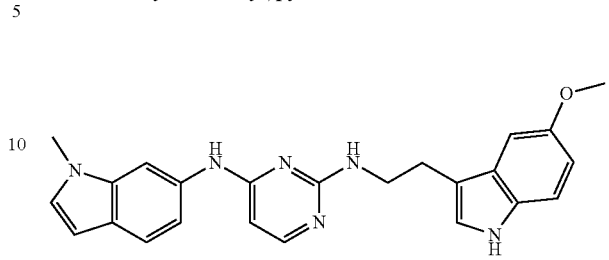

¹H NMR (400 MHz, DMSO-d₆, 75° C.) δ 10.42 (s, 1H), 8.80 (s, 1H), 7.99 (s, 1H), 7.83 (d, 1H), 7.40 (d, 1H), 7.24 (d, 1H), 7.13-7.05 (m, 4H), 6.72 (dd, 1H), 6.33 (d, 1H), 6.29 (t, 1H), 6.03 (d, 1H), 3.73 (s, 3H), 3.66 (q, 2H), 3.58 (s, 3H), 2.98 (t, 2H).

MS (ESI⁺) m/z 413.2 [M+H]⁺.

EXAMPLE 76

$N^2$-[2-(5-ethoxy-1H-indol-3-yl)ethyl]-$N^4$-(1-methylindol-6-yl)pyrimidine-2,4-diamine

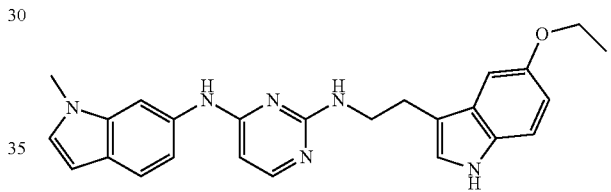

¹H NMR (400 MHz, DMSO-d₆, 75° C.) δ 10.41 (s, 1H), 8.80 (s, 1H), 8.00 (s, 1H), 7.83 (d, 1H), 7.41 (d, 1H), 7.23 (d, 1H), 7.13-7.05 (m, 4H), 6.71 (dd, 1H), 6.32 (d, 1H), 6.28 (t, 1H), 6.03 (d, 1H), 3.98 (q, 2H), 3.64 (q, 2H), 3.57 (s, 3H), 2.97 (t, 2H), 1.30 (t, 3H).

MS (ESI⁺) m/z 427.2 [M+H]⁺.

EXAMPLE 77

$N^2$-[2-(5-methoxy-1H-indol-3-yl)ethyl]-$N^4$-(2-methyl-1H-indol-4-yl)pyrimidine-2,4-diamine

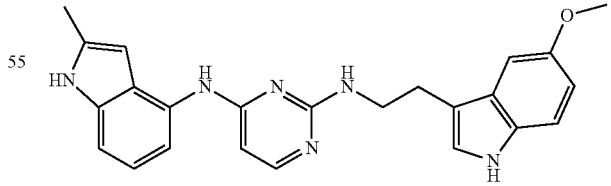

¹H NMR (400 MHz, DMSO-d₆, 75° C.) δ 10.68 (s, 1H), 10.42 (s, 1H), 8.34 (s, 1H), 7.83 (d, 1H), 7.51 (d, 1H), 7.24 (d, 1H), 7.09 (dd, 2H), 7.01 (d, 1H), 6.90 (dd, 1H), 6.73 (dd, 1H), 6.29 (s, 1H), 6.20 (m, 1H), 6.07 (d, 1H), 3.76 (s, 3H), 3.59 (q, 2H), 2.94 (t, 2H), 2.38 (s, 3H).

MS (ESI⁺) m/z 413.2 [M+H]⁺.

EXAMPLE 78

N²-[2-(5-ethoxy-1H-indol-3-yl)ethyl]-N⁴-(2-methyl-1H-indol-4-yl)pyrimidine-2,4-diamine

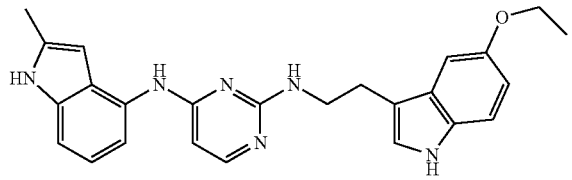 [SMILES: CCOc1ccc2[nH]cc(CCNc3nccc(Nc4cccc5[nH]c(C)cc45)n3)c2c1]

¹H NMR (400 MHz, DMSO-d₆, 75° C.) δ 10.68 (s, 1H), 10.40 (s, 1H), 8.34 (s, 1H), 7.83 (d, 1H), 7.51 (d, 1H), 7.23 (d, 1H), 7.10-7.07 (m, 2H), 7.01 (d, 1H), 6.91 (t, 1H), 6.72 (dd, 1H), 6.29 (s, 1H), 6.19 (t, 1H), 6.07 (d, 1H), 4.02 (q, 2H), 3.58 (q, 2H), 2.94 (t, 2H), 2.38 (s, 3H), 1.32 (t, 3H).
MS (ESI⁺) m/z 427.2 [M+H]⁺.

EXAMPLE 79

3-[2-({4-[(1-methylindol-4-yl)amino]pyrimidin-2-yl}amino)ethyl]-1H-indol-5-ol

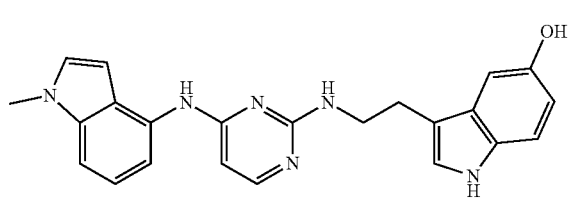 [SMILES: Cn1ccc2c(Nc3ccnc(NCCc4c[nH]c5ccc(O)cc45)n3)cccc21]

¹H NMR (400 MHz, DMSO-d₆, 75° C.) δ 10.26 (s, 1H), 8.51 (s, 1H), 8.28 (br s, 1H), 7.86 (d, 1H), 7.69 (d, 1H), 7.21 (d, 1H), 7.15-7.03 (m, 4H), 6.91 (d, 1H), 6.64-6.61 (m, 2H), 6.24 (t, 1H), 6.13 (d, 1H), 3.78 (s, 3H), 3.57 (q, 2H), 2.90 (t, 2H).
MS (ESI⁺) m/z 399.2 [M+H]⁺.

EXAMPLE 80

N²-[2-(5-ethoxy-1H-indol-3-yl)ethyl]-N⁴-(1-methylindol-4-yl)pyrimidine-2,4-diamine

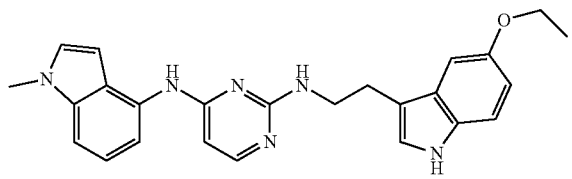 [SMILES: CCOc1ccc2[nH]cc(CCNc3nccc(Nc4cccc5c4ccn5C)n3)c2c1]

¹H NMR (400 MHz, DMSO-d₆, 75° C.) δ 10.41 (s, 1H), 8.51 (s, 1H), 7.86 (d, 1H), 7.71 (d, 1H), 7.24-7.21 (m, 2H), 7.13-7.04 (m, 4H), 6.72 (dd, 1H), 6.65 (d, 1H), 6.26 (t, 1H), 6.14 (d, 1H), 4.02 (q, 2H), 3.78 (s, 3H), 3.58 (q, 2H), 2.94 (t, 2H), 1.32 (t, 3H).
MS (ESI⁺) m/z 427.2 [M+H]⁺.

EXAMPLE 81

N⁴-(1,2-dimethylindol-4-yl)-N²-[2-(5-methoxy-1H-indol-3-yl)ethyl]pyrimidine-2,4-diamine

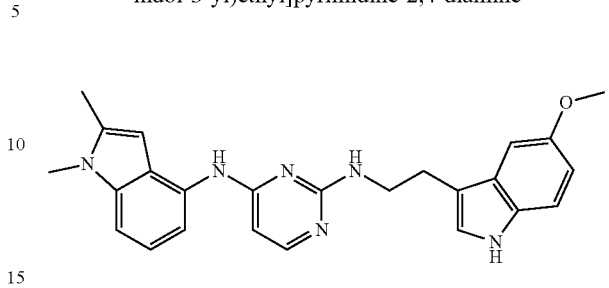

¹H NMR (400 MHz, DMSO-d₆, 75° C.) δ 10.42 (s, 1H), 8.39 (s, 1H), 7.83 (d, 1H), 7.58 (d, 1H), 7.24 (d, 1H), 7.11-7.04 (m, 3H), 6.98 (dd, 1H), 6.73 (dd, 1H), 6.38 (s, 1H), 6.22 (m, 1H), 6.08 (d, 1H), 3.76 (s, 3H), 3.65 (s, 3H), 3.58 (q, 2H), 2.94 (t, 2H), 2.40 (s, 3H).
MS (ESI⁺) m/z 427.2 [M+H]⁺.

EXAMPLE 82

N²-[2-(5-methoxy-1H-indol-3-yl)ethyl]-N⁴-(2-methyl-1H-benzimidazol-4-yl)pyrimidine-2,4-diamine

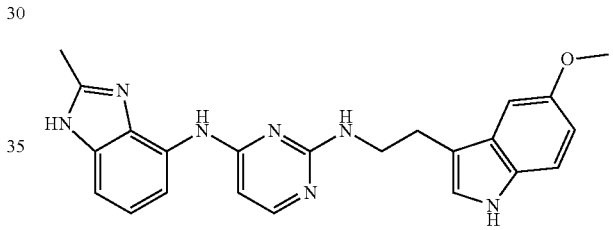

¹H NMR (400 MHz, CD₃OD, 45° C.) δ 7.83 (d, 1H), 7.23 (d, 2H), 7.12 (dd, 1H), 7.05 (d, 1H), 7.02 (br s, 1H), 6.76 (dd, 1H), 6.09 (br d, 1H), 3.78 (s, 3H), 3.66 (br t, 2H), 3.01 (br t, 2H), 2.53 (s, 3H).
MS (ESI⁺) m/z 414.2 [M+H]⁺.

EXAMPLE 83

N²-[2-(5-ethoxy-1H-indol-3-yl)ethyl]-N⁴-(2-methyl-1H-benzimidazol-4-yl)pyrimidine-2,4-diamine

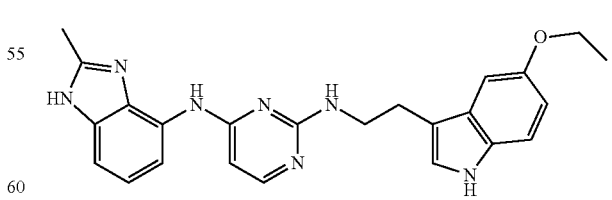

¹H NMR (400 MHz, CD₃OD, 45° C.) δ 7.83 (d, 1H), 7.23 (d, 2H), 7.12 (dd, 1H), 7.05 (d, 1H), 7.02 (br s, 1H), 6.76 (dd, 1H), 6.09 (br d, 1H), 4.01 (q, 2H), 3.64 (br t, 2H), 3.00 (br t, 2H), 2.53 (s, 3H), 1.43 (t, 3H).
MS (ESI⁺) m/z 428.2 [M+H]⁺.

EXAMPLE 84

N⁴-[2-(5-methoxy-1H-indol-3-yl)ethyl]-N²-(1-methylindol-4-yl)pyrimidine-2,4-diamine

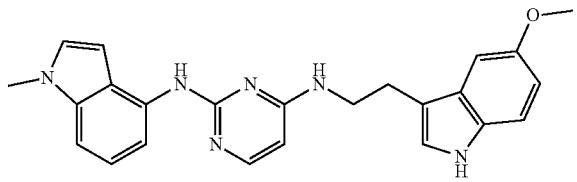

$^1$H NMR (400 MHz, DMSO-d$_6$, 75° C.) δ 10.46 (s, 1H), 7.98 (s, 1H), 7.92 (dd, 1H), 7.83 (d, 1H), 7.25 (d, 1H), 7.15 (d, 1H), 7.11 (s, 1H), 7.04-6.99 (m, 3H), 6.92 (m, 1H), 6.75-6.71 (m, 2H), 5.98 (d, 1H), 4.06 (q, 2H), 3.75 (ds, 6H), 3.62 (q, 2H).
MS (ESI$^+$) m/z 413.2 [M+H]$^+$.

EXAMPLE 85

2-[2-(5-ethoxy-1H-indol-3-yl)ethylamino]-6-[(2-methyl-1H-indol-5-yl)amino]pyrimidine-4-carboxamide

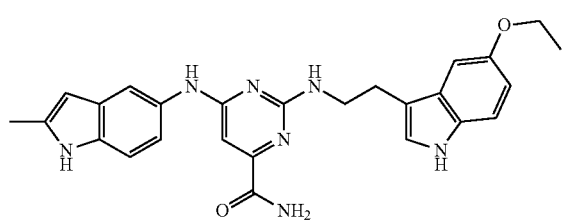 [SMILES: CCOc1ccc2[nH]cc(CCNc3nc(Nc4ccc5[nH]c(C)cc5c4)cc(C(N)=O)n3)c2c1]

$^1$H NMR (400 MHz, DMSO-d$_6$, 75° C.) δ 10.58 (s, 1H), 10.43 (s, 1H), 8.85 (s, 1H), 7.68 (s, 1H), 7.55 (br s, 1H), 7.24-7.18 (m, 3H), 7.12 (m, 2H), 7.03 (d, 1H), 6.72 (dd, 1H), 6.57 (s, 1H), 6.37 (t, 1H), 6.01 (s, 1H), 4.01 (q, 2H), 3.65 (q, 2H), 2.98 (t, 2H), 2.37 (s, 3H), 1.31 (t, 3H).
MS (ESI$^+$) m/z 470.2 [M+H]$^+$.

EXAMPLE 86

6-[(1,2-dimethylbenzimidazol-5-yl)amino]-2-[2-(5-methoxy-1H-indol-3-yl)ethylamino]pyrimidine-4-carboxamide

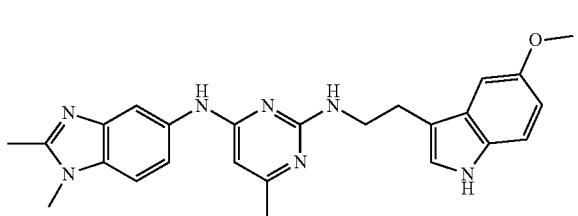

$^1$H NMR (400 MHz, DMSO-d$_6$, 75° C.) δ 10.43 (s, 1H), 9.07 (s, 1H), 7.90 (s, 1H), 7.56 (br s, 1H), 7.38 (dd, 1H), 7.32 (d, 1H), 7.24 (d, 1H), 7.23 (br s, 1H), 7.19 (d, 1H), 7.03 (d, 1H), 6.73 (dd, 1H), 6.62 (s, 1H), 6.49 (m, 1H), 3.75 (s, 3H), 3.71 (s, 3H), 3.66 (q, 2H), 2.99 (t, 2H), 2.52 (s, 3H).
MS (ESI$^+$) m/z 471.2 [M+H]$^+$.

EXAMPLE 87

2-[2-(5-methoxy-1H-indol-3-yl)ethylamino]-6-[(1-methylindol-4-yl)amino]pyrimidine-4-carboxamide

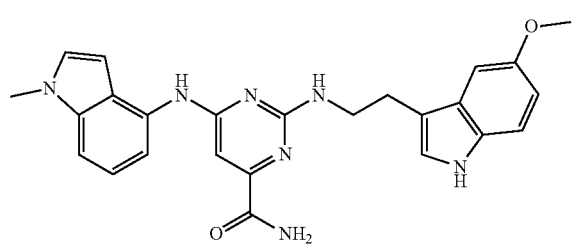

$^1$H NMR (400 MHz, DMSO-d$_6$, 75° C.) δ 10.44 (s, 1H), 8.88 (s, 1H), 7.74 (d, 1H), 7.58 (br s, 1H), 7.25-7.22 (m, 3H), 7.16-7.04 (m, 4H), 6.81 (s, 1H), 6.73 (dd, 1H), 6.67 (d, 1H), 6.49 (t, 1H), 3.79 (s, 3H), 3.75 (s, 3H), 3.66 (q, 2H), 2.98 (t, 2H).
MS (ESI$^+$) m/z 456.2 [M+H]$^+$.

EXAMPLE 88

2-[2-(5-ethoxy-1H-indol-3-yl)ethylamino]-6-[(1-methylindol-4-yl)amino]pyrimidine-4-carboxamide

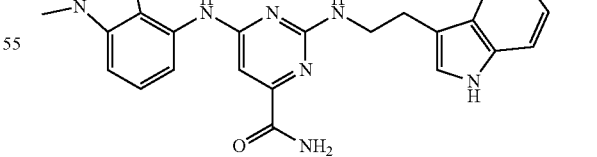

$^1$H NMR (400 MHz, DMSO-d$_6$, 75° C.) δ 10.43 (s, 1H), 8.88 (s, 1H), 7.75 (d, 1H), 7.57 (br s, 1H), 7.25-7.21 (m, 3H), 7.16-7.06 (m, 3H), 7.03 (d, 1H), 6.81 (s, 1H), 6.72 (dd, 1H), 6.68 (d, 1H), 6.48 (t, 1H), 4.01 (q, 2H), 3.79 (s, 3H), 3.65 (q, 2H), 2.97 (t, 2H), 1.31 (t, 3H).
MS (ESI$^+$) m/z 470.2 [M+H]$^+$.

EXAMPLE 89

N²-[2-(5-methoxy-1H-indol-3-yl)ethyl]-N⁴-(1-methylindol-4-yl)-6-(4-methylpiperazin-1-yl)pyrimidine-2,4-diamine

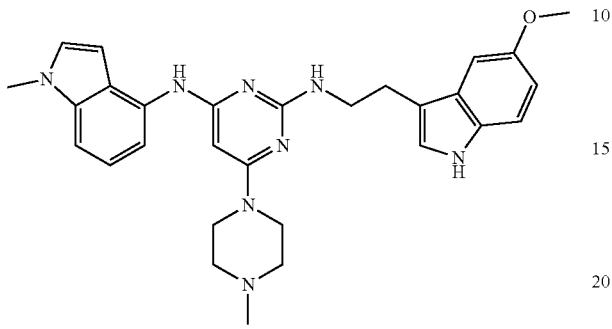

$^1$H NMR (400 MHz, CD$_3$OD) δ 7.24-7.12 (m, 5H), 7.06 (m, 2H), 6.76 (dd, 1H), 6.46 (d, 1H), 3.81 (s, 3H), 3.80 (s, 3H), 3.66 (t, 2H), 3.49 (m, 4H), 1.95 (t, 2H), 3.95 (m, 4H), 2.32 (s, 3H).
MS (ESI$^+$) m/z 511.3 [M+H]$^+$.

EXAMPLE 90

N²-[2-(5-ethoxy-1H-indol-3-yl)ethyl]-N⁴-(2-methyl-1H-indol-5-yl)pyrimidine-2,4,5-triamine

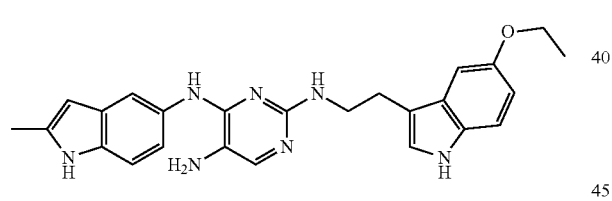

$^1$H NMR (400 MHz, DMSO-d$_6$) δ 10.70 (s, 1H), 10.60 (s, 1H), 7.93 (s, 1H), 7.78 (s, 1H), 7.47 (s, 1H), 7.25-7.03 (m, 5H), 6.69 (dd, 1H), 5.91 (s, 1H), 5.82 (t, 1H), 3.96 (q, 2H), 3.46 (q, 2H), 2.88 (t, 2H), 2.34 (s, 3H), 1.31 (t, 3H).
MS (ESI$^+$) m/z 442.2 [M+H]$^+$.

INTERMEDIATE 91

N-(2-chloropyrimidin-4-yl)-2-methyl-1H-indol-6-amine

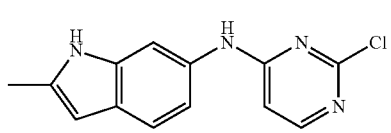 [SMILES: Cc1cc2ccc(Nc3ccnc(Cl)n3)cc2[nH]1]

$^1$H NMR (400 MHz, DMSO-d$_6$, 75° C.) δ 10.73 (s, 1H), 9.61 (s, 1H), 8.05 (d, 1H), 7.55 (s, 1H), 7.36 (d, 1H), 6.97 (dd, 1H), 6.65 (d, 1H), 6.10 (s, 1H), 2.38 (s, 3H).

INTERMEDIATE 92

N-(2-chloropyrimidin-4-yl)-1-methyl-indol-6-amine

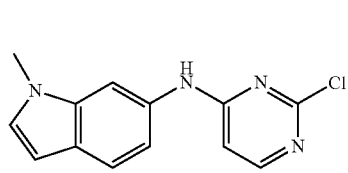 [SMILES: Cn1ccc2ccc(Nc3ccnc(Cl)n3)cc21]

$^1$H NMR (400 MHz, DMSO-d$_6$, 75° C.) δ 9.73 (s, 1H), 8.08 (d, 1H), 7.65 (s, 1H), 7.53 (d, 1H), 7.27 (d, 1H), 7.09 (dd, 1H), 6.70 (d, 1H), 6.41 (d, 1H), 3.77 (s, 3H).

INTERMEDIATE 93

N-(2-chloropyrimidin-4-yl)-2-methyl-1H-indol-4-amine

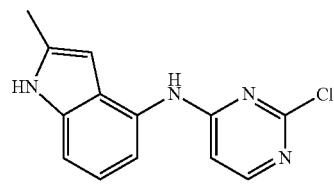 [SMILES: Cc1cc2c(Nc3ccnc(Cl)n3)cccc2[nH]1]

$^1$H-NMR (400 MHz, DMSO-d$_6$, 75° C.) δ 10.87 (s, 1H), 9.52 (s, 1H), 8.06 (d, 1H), 7.17 (d, 1H), 7.16 (d, 1H), 7.01 (dd, 1H), 6.59 (d, 1H), 6.13 (s, 1H), 2.39 (s, 3H).

INTERMEDIATE 94

N-(2-chloropyrimidin-4-yl)-1,2-dimethyl-indol-4-amine

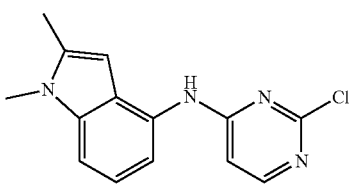 [SMILES: Cc1cc2c(Nc3ccnc(Cl)n3)cccc2n1C]

¹H-NMR (400 MHz, DMSO-d$_6$, 75° C.) δ 9.54 (s, 1H), 8.06 (d, 1H), 7.25 (d, 1H), 7.22 (d, 1H), 7.09 (dd, 1H), 6.60 (d, 1H), 6.23 (s, 1H), 3.69 (s, 3H), 2.42 (s, 3H).

INTERMEDIATE 95

N-(2-chloropyrimidin-4-yl)-2-methyl-1H-benzimidazol-4-amine

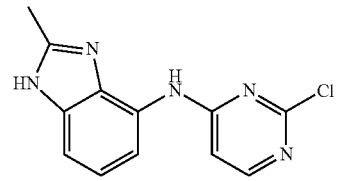

¹H-NMR (400 MHz, DMSO-d$_6$, 115° C.) δ 8.10 (d, 1H), 7.48 (br s, 1H), 7.27 (br d, 1H), 7.13 (dd, 1H), 6.81 (br m, 1H), 2.52 (s, 3H).

INTERMEDIATE 96

2-chloro-6-[(1,2-dimethylbenzimidazol-5-yl)amino]pyrimidine-4-carboxamide

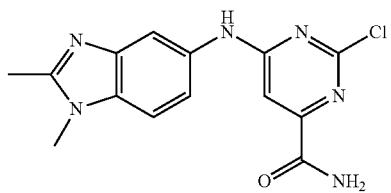 [SMILES: Cc1nc2cc(Nc3cc(C(N)=O)nc(Cl)n3)ccc2n1C]

¹H NMR (400 MHz, DMSO-d$_6$, 115° C.) δ 9.84 (s, 1H), 7.73 (d, 1H), 7.46 (br s, 2H), 7.44 (d, 1H), 7.29 (dd, 1H), 7.23 (s, 1H), 3.74 (s, 3H), 2.54 (s, 3H).

INTERMEDIATE 97

2-chloro-6[(1-methylindol-4-yl)amino]pyrimidine-4-carboxamide

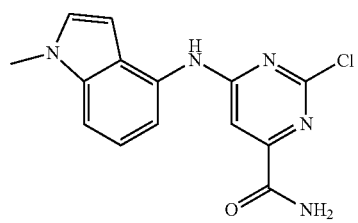 [SMILES: Cn1ccc2c(Nc3cc(C(N)=O)nc(Cl)n3)cccc21]

¹H NMR (400 MHz, DMSO-d$_6$, 75° C.) δ 9.96 (s, 1H), 7.72 (br s, 1H), 7.57 (br s, 1H), 7.39-7.28 (m, 4H), 7.20 (t, 1H), 6.51 (d, 1H), 3.83 (s, 3H).

INTERMEDIATE 98

N-(2-chloro-5-nitro-pyrimidin-4-yl)-2-methyl-1H-indol-5-amine

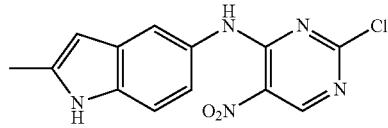 [SMILES: Cc1cc2cc(Nc3nc(Cl)ncc3[N+](=O)[O-])ccc2[nH]1]

¹H NMR (400 MHz, DMSO-d$_6$, 75° C.) δ 10.84 (s, 1H), 10.26 (s, 1H), 9.08 (s, 1H), 7.54 (s, 1H), 7.31 (d, 1H), 7.11 (dd, 1H), 6.17 (s, 1H), 2.41 (s, 3H).

INTERMEDIATE 99

N²-[2-(5-ethoxy-1H-indol-3-yl)ethyl]-N⁴-(2-methyl-1H-indol-5-yl)-5-nitro-pyrimidine-2,4-diamine

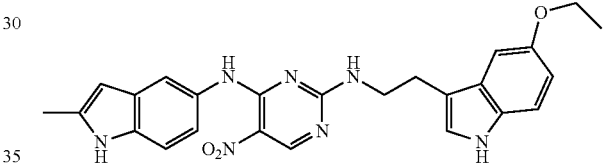

¹H NMR (400 MHz, DMSO-d$_6$, 125° C.) δ 10.49 (br s, 1H), 10.19 (br s, 2H), 8.96 (s, 1H), 7.76 (br s, 2H), 7.25-7.20 (m, 3H), 7.00 (s, 1H), 6.73 (dd, 1H), 6.02 (s, 1H), 4.01 (q, 2H), 3.65 (q, 2H), 2.97 (t, 2H), 2.39 (s, 3H), 1.32 (t, 3H).

Biological Assays

The Fluorometric Microculture Cytotoxicity Assay, FMCA (Larsson, R., et al.; Anticancer Res, 1989, 9, 1111-1119), is a three day non-clonogenic microplate-based cell viability assay used for measurement of the cytotoxic and/or cytostatic effect of compounds in vitro (Lindhagen, E. et al.; Nat. Protoc., 2008, 3, 1364-1369). FMCA represents a valuable method to measure cytotoxicity in a number of cell types, both cell lines and primary cells from patients (Larsson, R., et al.; Int. J. Cancer, 1992, 50, 177-185; Fridborg, H., et al.; Eur. J. Cancer, 1999. 35, 424-432; Dhar, S., et al.; Br. J. Cancer, 1996, 74, 888-896).

FMCA is based on the principle that fluorescein diacetate (FDA) is converted to the fluorescent probe fluorescein by esterases in the plasma membranes of living cells. For experiments, 96 or 384-well microplates are prepared with compounds and stored at −70° C. until use. Cells are then seeded into the drug-prepared plates and placed in an incubator for 72 h. On the last day of incubation, the plates are washed and a buffer containing FDA is added and incubated with the cells for 45 minutes. Finally the fluorescence per well is measured in a fluorometer and a Survival Index % (SI) for each compound-treated well is calculated with the equation: Compound-treated cells minus blank divided by control cells minus blank. A high SI-value indicates a large percentage of living cells and vice versa.

For experiments with compounds of the invention, 96-well plates were prepared as follows:

Compounds were dissolved in DMSO to 10 mM and stored at −20° C. 96-well plates were prepared with 297 µl of sterile PBS added to each well. The test compounds were thawed, protected from light, mixed, and 3 µl stock solution was added to the 96-well plate to give the concentration 100 µM. Then, an assay plate was prepared by transferring 20 µl of compound solution to a V-bottomed 96-well plate. Compounds at 100 µM were diluted with PBS to 10 µM, and an assay plate containing 20 µl was prepared. The plates were stored at −70° C. until use.

On the day of cell seeding, 180 µl of cell suspension was added to each well in the two assay plates. The final concentration of compounds tested was thus 10 µM and 1 µM.

In subsequent experiments, compounds were tested, along with a number of approved cancer drugs (dasatinib, pazopanib, sorafenib, and sunitinib) as described above. Initially, the acute lymphoblastic leukemia cell line CCRF-CEM was used throughout. In the assay plates, medium was added to six empty wells (blank wells) and wells were filled with PBS and cell suspension and served as control wells. SI-values were then calculated for each compound-treated well as described above. All experiments were conducted twice and a new batch of plates was prepared for each experiment. The data obtained showed the activity of the example compounds compared to the comparative compounds.

For dose-response experiments, 384-well plates were prepared as follows:

Compounds of the invention as well comparative kinase inhibitors sorafenib sunitinib, dasatinib, pazopanib and a reference compound disclosed in WO 2009/071535 (compound #107) were diluted with PBS to a concentration ten-times higher than the desired starting concentration. Then, a Biomek 2000 liquid handling system was employed to serially dilute the compounds in a deep-well 384-well plate. From this plate, assay plates containing 5 µl compound per well were prepared with the Biomek 2000. Certain compounds precipitated when diluted with PBS, and these compounds were therefore prepared in a 96-well plate manually as described above using culture medium RPMI 1640 instead of PBS.

The compounds were also tested at five concentrations, with five times serial dilution on the following cell types: CCRF-CEM, hTERT-RPE1 (normal retinal epithelial cells), hRPTEpiC (normal renal cells), and peripheral blood mononuclear cells (PBMC). Each experiment was performed three times, except for PBMC and hRPTEpiC, which were performed twice. SI-values were calculated, graphs were plotted using GraphPadPrism 5.0 (GraphPad Software Inc. La Jolla, Calif.) and $IC_{50}$-values for each cell type and compound were determined from the curves.

The example compounds of the invention were active in the CCRF-CEM cell measurements, showing EC50 values less than 10 µM. Preferred compounds of the invention had EC50 values less than 1 µM. More preferred compounds of the invention had EC50 values less than 0.1 µM, and the reference compounds, sorafenib, sunitinib, dasatinib, pazopanib and WO 2009/071535 compound #107 had EC50 values of 8.3 µM, 14.1 µM, 9.7 µM, 25.9 µM, and 1-10 µM, respectively. Most of the compounds of the invention showed lower EC50 values than the reference compounds and data is presented in Table 1.

TABLE 1

| EC50 (µM) in CCRF-CEM cancer cells - leukemia | |
| --- | --- |
| Example number | CCRF-CEM EC50 (µM) |
| 1 | 4.1 |
| 2 | 0.14 |
| 3 | 0.29 |
| 4 | 0.028 |
| 5 | 0.015 |
| 6 | 2.9 |
| 7 | 0.14 |
| 8 | 3.1 |
| 9 | 0.038 |
| 10 | 0.28 |
| 11 | 0.15 |
| 12 | 0.13 |
| 13 | 0.019 |
| 14 | 0.021 |
| 15 | 0.027 |
| 16 | 0.94 |
| 17 | 1.4 |
| 18 | 0.42 |
| 19 | 0.032 |
| 20 | 0.14 |
| 21 | 0.059 |
| 22 | 3.4 |
| 23 | 0.059 |
| 24 | 1-10 |
| 25 | 1-10 |
| 26 | 0.65 |
| 27 | 0.019 |
| 28 | 0.058 |
| 29 | 0.057 |
| 30 | 3.0 |
| 47 | 0.33 |
| 48 | 1.3 |
| 49 | 0.10 |
| 50 | 0.18 |
| 51 | 0.076 |
| 52 | 0.43 |
| 53 | 0.033 |
| 54 | 0.0028 |
| 55 | 0.053 |
| 56 | 0.13 |
| 57 | 0.23 |
| 58 | 0.17 |
| 59 | 1-10 |
| 60 | 0.21 |
| 61 | 1-10 |
| 62 | 1-10 |
| 72 | <0.1 |
| 73 | <0.1 |
| 74 | <0.1 |
| 75 | <1 |
| 76 | <1 |
| 77 | <0.1 |
| 78 | <0.1 |
| 79 | <1 |
| 80 | <0.1 |
| 81 | <0.1 |
| 82 | <1 |
| 83 | <1 |
| 84 | <0.1 |
| 85 | <0.1 |
| 86 | <1 |
| 87 | <0.1 |
| 88 | <0.1 |
| 89 | <1 |
| 90 | <0.1 |
| Ref. 1 | 8.3 |
| Ref. 2 | 14.1 |
| Ref. 3 | 9.7 |
| Ref. 4 | 25.9 |
| Ref. 5 | 1-10 |

Ref. 1 denotes reference compound sorafenib
Ref. 2 denotes reference compound sunitinib
Ref. 3 denotes reference compound dasatinib
Ref. 4 denotes reference compound pazopanib
Ref. 5 WO 2009/071535 compound #107

Further, primary results also showed that the compounds of the invention exhibited an enhanced selectivity towards CCRF-CEM cells, compared to the tested hTERT-RPE1 (normal retinal epithelial cells), hRPTEpiC (normal renal cells), and peripheral blood mononuclear cells (PBMC).

The compounds of the invention were also tested on further cancer cell lines related to breast cancer (MDA-MB-231; see e.g. Cailleau, R., et al.; J. Natl. Cancer Inst., 1974, 53, 661-674), teniposide-resistant leukemia (CEM/VM1 see e.g. Danks, M., et al.; Cancer Res., 1987, 47, 1297-1301), leukemia (HL-60; see e.g. Collins, S., et al.; Nature, 1977, 270, 347-349), doxorubicin-resistant lung cancer (H69AR; see e.g. Mirski, S., et al.; Cancer Res., 1987, 47, 2594-2598), myeloma (RPMI 8226; see e.g. Matsuoka, Y., et al.; Proc. Soc. Exp. Biol. Med., 1967, 125, 1246-1250), doxorubicin-resistant myeloma (8226/Dox40; see e.g. Dalton, W., et al.; Blood, 1989, 15, 747-752), lymphoma (U-937, see e.g. Sundström, C., et al.; Int. J. Cancer, 1976, 17, 565-577), vincristin-resistant lymphoma (U-937-vcr; see e.g. Botling, J., et al.; Int. J. Cancer, 1994, 58, 269-274), ovarian cancer (A2780; see e.g. Hamilton, T., et al.; Semin. Oncol., 1984, 11, 285-298), doxorubicin-resistant ovarian cancer (A2780/Adr), cisplatin-resistant ovarian cancer (A2780/Cis; see e.g. Behrens, B., et al. Cancer Res. 1987, 47, 414-418), pancreatic cancer (PANC-1, BxPC-3, and MIA PaCa-2; see e.g. Lieber, M., et al.; Int. J. Cancer, 1975, 15, 741-747; Loor, R., et al.; Clin. Lab. Med., 1982, 2, 567-578; and Yunis, A., et al.; Int. J. Cancer, 1977, 19, 128-135) and prostate cancer (PC-3; see e.g. Kaighn, M., et al.; Invest. Urol., 1979, 17, 16-23). Representative results of these tests are presented in Table 2 and Table 3.

TABLE 2

EC50 (µM) in various cancer cell lines

| Ex. | MDA-MB-231 | CEM/VM1 | HL-60 | H69AR | RPMI 8226 | 8226/Dox40 | U-937 | U-937-vcr |
|---|---|---|---|---|---|---|---|---|
| 4 | 0.10 | 0.0066 | 0.0091 | 0.023 | 0.045 | 0.11 | 0.013 | 0.028 |
| 5 | 0.057 | 0.017 | 0.0082 | 0.094 | 0.042 | 0.16 | 0.022 | 0.020 |
| 9 | nt | 0.064 | nt | 0.17 | 0.17 | 0.20 | 0.080 | 0.046 |
| 13 | 0.38 | 0.038 | 0.020 | 0.12 | 0.12 | 0.18 | 0.030 | 0.029 |
| 14 | nt | 0.051 | nt | 0.20 | 0.21 | 0.28 | 0.073 | 0.044 |
| 15 | 0.15 | 0.071 | 0.031 | 0.12 | 1.4 | 4.3 | 0.037 | 0.069 |
| 19 | 1.9 | 0.062 | 0.092 | 0.94 | 7.8 | 30 | 0.10 | 0.78 |
| 27 | nt | 0.044 | nt | 0.063 | 0.11 | 0.30 | 0.041 | 0.062 |

"nt" denotes "not yet tested".

TABLE 3

EC50 (µM) in various cancer cell lines

| Ex. | A2780 | A2780/Adr | A2780/Cis | BxPC-3 | PANC-1 | MIA PaCa-2 | PC-3 |
|---|---|---|---|---|---|---|---|
| 4 | 0.033 | 0.14 | 0.025 | 0.037 | 1.6 | 0.014 | 0.24 |
| 5 | 0.051 | 0.18 | 0.033 | 0.055 | 0.43 | 0.018 | 0.15 |
| 9 | 0.21 | 0.82 | 0.20 | nt | nt | nt | nt |
| 13 | 0.064 | 0.33 | 0.073 | 0.13 | 0.86 | 0.054 | 0.38 |
| 14 | 0.11 | 0.44 | 0.063 | nt | nt | nt | nt |
| 15 | 0.055 | 0.98 | 0.096 | 0.12 | 1.4 | 0.058 | 0.31 |
| 19 | 0.13 | 2.0 | 0.23 | 0.91 | 5.2 | 0.031 | 2.1 |
| 27 | 0.074 | 0.44 | 0.062 | nt | nt | nt | nt |

"nt" denotes "not yet tested".

Example compounds were further tested in a tubulin polymerization assay kit from Cytoskeleton Inc (Denver, Colo., USA). Polymerization is followed by fluorescence enhancement due to the incorporation of a fluorescent reporter into microtubules as polymerization occurs. Vincristine and paclitaxel at 3 µM were used as positive controls for tubulin polymerization inhibition and stabilisation, respectively. All compounds were dissolved in DMSO, which was used as solvent control. For experiments, example compounds and control compounds were incubated with bovine tubulin protein in a cell-free environment and the fluorescence was then measured in a fluorometer (Fluostar Optima, BMG Labtech, Offenburg, Germany) at 360/450 nm every minute for a total of 60 mins. Selected example compounds were tested and showed inhibitory effects on tubulin polymerization.

Some example compounds were further tested in cell cycle experiments. In these the Click-iT® EdU Assay (Molecular Probes/Invitrogen) was used according to the instructions from the manufacturer. HCT 116 cells were plated at a density of 6000 cells per well and left to attach to the bottom of black glass-bottom 96-well PerkinElmer plates. Compounds were then added and incubated with the cells for 24 h. Ciclopirox at 10 µM was used as positive control for G1 arrest and vincristine at 10 µM was positive control for G2/M arrest. EdU (5-ethynyl-2'-deoxyuridine) solution for quantification of newly synthesized DNA was added directly after the compounds. On the next day, the cells were formaldehyde-fixed and permeabilized and the Click-iT reaction was performed. Finally, a DNA stain was added to label the cell nuclei.

Quantitative analysis was then performed in an ArrayScan VTI HCS reader (Thermo Fischer Cellomics) using the Target Activation Bioapplication software. A total of 1500 cells per well were analysed on the cellular level and data representing DNA content were plotted in histograms for each treatment condition. The average fluorescence intensity of the nuclear stain in each cell, with a bin width of 20, is plotted on the X-axis and the number of cells on the Y-axis. In the histogram, cells that are arrested in the G1 phase are located in the first peak to the left and cells that are arrested in G2/M phase are located in the second peak to the right. Selected example compounds were tested and most of them displayed a G2/M arrest that is typical for tubulin inhibitors.

Example compounds were further tested for induction of apoptosis in a Live cell imaging setup. The NucView™ 488 Caspase-3 Assay Kit for Live cells (Biotium, Inc. Hayward, Calif., USA) was used. HCT116 cells were plated the day before the experiment in black glass-bottom PerkinElmer plates and compounds with chosen concentrations were then added. Finally, the DEVD-NucView488 Caspase-3 substrate was added and the plate was placed in an IncuCyteFLR for live-cell imaging. When the substrate is cleaved by activated caspase-3, a dye is released which becomes fluorescent upon binding to DNA (see Cen, H., et al.; FASEB J., 2008, 22, 2243-2252). Staurosporin at 1 µM was used as a positive control for apoptosis. Selected example compounds were tested and all of them induced apoptosis at the chosen concentrations at varying time points.

The invention claimed is:

1. A compound of formula I or a pharmaceutically acceptable ester, solvate or salt thereof,

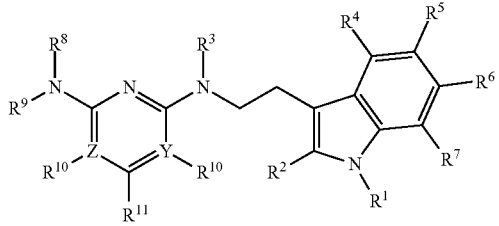

wherein

Z represents carbon or nitrogen;

Y represents carbon or nitrogen, wherein one of Z and Y represents nitrogen;

$R^1$, $R^3$, and $R^8$ are independently selected from the group consisting of hydrogen and $(C_1-C_4)$alkyl;

$R^2$ is selected from the group consisting of hydrogen, $(C_1-C_4)$alkyl, $(C_1-C_4)$alkyl-NH$(C_1-C_4)$alkyl, $(C_1-C_4)$alkyl-N[$(C_1-C_4)$alkyl]$_2$, and (CO)OH;

$R^4$, $R^5$, $R^6$, and $R^7$ are independently selected from the group consisting of hydrogen, halogen, hydroxy, amino, nitro, cyano, $(C_1-C_4)$alkyl, $(C_1-C_4)$alkyl-OH, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl]$_2$, $(C_1-C_4)$alkyl-NH(CO)$(C_1-C_4)$alkyl, (CO)OH, (CO)NH$_2$, (CO)NH$(C_1-C_4)$alkyl, (CO)N[$(C_1-C_4)$alkyl]$_2$, O$(C_1-C_4)$alkyl, O$(C_1-C_4)$alkyl$(C_2-C_5)$heterocyclyl, O$(C_1-C_4)$alkyl$(C_2-C_5)$heterocyclyl$(C_1-C_4)$alkyl, O$(C_1-C_4)$alkyl(CO)OH, O$(C_1-C_4)$alkyl(CO)NH$(C_1-C_4)$alkyl, O$(C_1-C_4)$alkyl(CO)N[$(C_1-C_4)$alkyl]$_2$, OCF$_3$, NH$(C_1-C_4)$alkyl, N[$(C_1-C_4)$alkyl ]$_2$, NH(CO)$(C_1-C_4)$alkyl, NHSO$_2(C_1-C_4)$alkyl, N[$(C_1-C_4)$alkyl]SO$_2(C_1-C_4)$alkyl, SH, S$(C_1-C_4)$alkyl, SO$_2$NH$_2$, SO$_2$NH$(C_1-C_4)$alkyl, and SO$_2$N[$(C_1-C_4)$alkyl]$_2$;

each $R^{10}$ is independently selected from the group consisting of hydrogen, amino, and $(C_1-C_4)$alkyl when Z or Y is carbon;

$R^{11}$ is selected from the group consisting of hydrogen, amino, $(C_1-C_4)$alkyl, $(C_1-C_4)$alkyl$(C_2-C_5)$heterocyclyl, $(C_1-C_4)$alkyl$(C_2-C_5)$heterocyclyl$(C_1-C_4)$alkyl, (CO)OH, (CO)NH$_2$, (CO)NH$(C_1-C_4)$alkyl, (CO)N[$(C_1-C_4)$alkyl]$_2$, (CO)$(C_1-C_4)$alkyl, $(C_2-C_5)$heterocyclyl, $(C_2-C_5)$heterocyclyl$(C_1-C_4)$alkyl, NH$(C_1-C_4)$alkyl, N[$(C_1-C_4)$alkyl]$_2$, NH(CO)$(C_1-C_4)$alkyl, NHSO$_2(C_1-C_4)$alkyl, N[$(C_1-C_4)$alkyl]SO$_2(C_1-C_4)$alkyl, SO$_2$NH$_2$, SO$_2$NH$(C_1-C_4)$alkyl, and SO$_2$N[$(C_1-C_4)$alkyl]$_2$;

$R^9$ represents

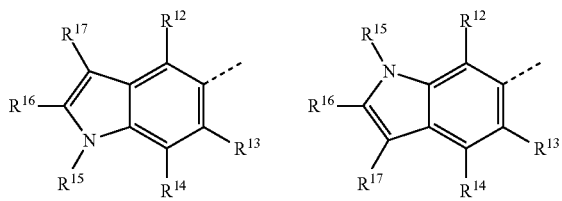

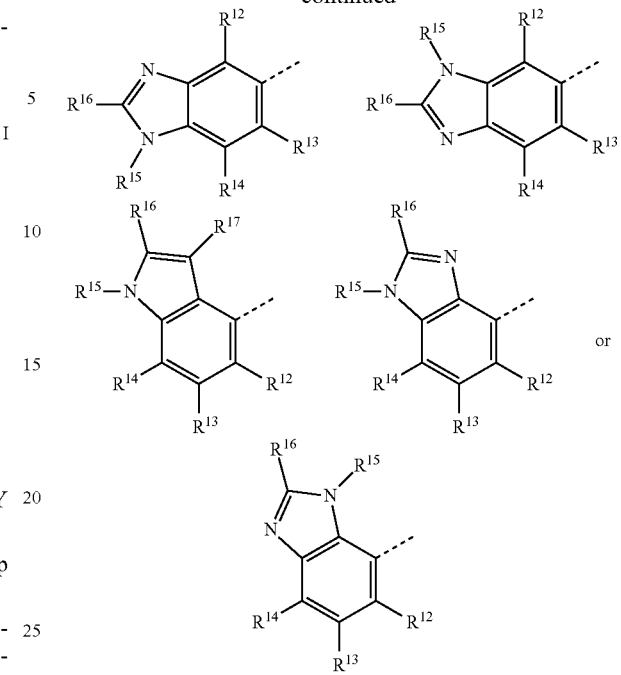

$R^{12}$, $R^{13}$, and $R^{14}$ are independently selected from the group consisting of hydrogen, halogen, hydroxy, $(C_1-C_4)$alkyl, O$(C_1-C_4)$alkyl, NH$(C_1-C_4)$alkyl, and N[$(C_1-C_4)$alkyl]$_2$;

$R^{15}$ is selected from hydrogen and $(C_1-C_4)$alkyl; and $R^{16}$ and $R^{17}$ are independently selected from the group consisting of hydrogen, halogen, $(C_1-C_4)$alkyl, $(C_1-C_4)$alkyl$(C_2-C_5)$heterocyclyl, $(C_1-C_4)$alkyl$(C_2-C_5)$heterocyclyl$(C_1-C_4)$alkyl, $(C_1-C_4)$alkyl(CO)OH, $(C_1-C_4)$alkyl(CO)NH$_2$, $(C_1-C_4)$alkyl(CO)NH$(C_1-C_4)$alkyl, $(C_1-C_4)$alkyl(CO)N[$(C_1-C_4)$alkyl]$_2$, $(C_1-C_4)$alkyl-OH, $(C_1-C_4)$alkyl-O$(C_1-C_4)$alkyl, $(C_1-C_4)$alkyl-NH$(C_1-C_4)$alkyl, $(C_1-C_4)$alkyl-N[$(C_1-C_4)$alkyl]$_2$, $(C_1-C_4)$alkyl-NH(CO)$(C_1-C_4)$alkyl, (CO)OH, (CO)NH$_2$, (CO)NH$(C_1-C_4)$alkyl, (CO)N[$(C_1-C_4)$alkyl]$_2$, (CO)$(C_1-C_4)$alkyl, (CO)$(C_2-C_5)$heterocyclyl, and (CO)$(C_2-C_5)$heterocyclyl)$(C_1-C_4)$alkyl.

2. The compound according to claim 1, wherein $R^1$ represents hydrogen.

3. The compound according to claim 1, wherein $R^2$, $R^3$, and $R^8$ are independently selected from the group consisting of hydrogen and methyl.

4. The compound according to claim 1, wherein $R^2$, $R^3$, and $R^8$ represent hydrogen.

5. The compound according to claim 1, wherein Z represents carbon and Y represents nitrogen.

6. The compound according to claim 1, wherein $R^4$, $R^5$, $R^6$, and $R^7$ are independently selected from the group consisting of hydrogen, halogen, hydroxy, $(C_1-C_4)$alkyl, O$(C_1-C_4)$alkyl, O$(C_1-C_4)$alkyl$(C_2-C_5)$heterocyclyl, and OCF$_3$.

7. The compound according to claim 1, wherein $R^5$ represents O$(C_1-C_4)$alkyl.

8. The compound according to claim 1, wherein $R^5$ is selected from the group consisting of methoxy, ethoxy and propoxy.

9. The compound according to claim 1, wherein $R^5$ is selected from the group consisting of methoxy and methyl.

10. The compound according to claim 1, wherein each $R^{10}$ is independently selected from the group consisting of hydrogen, $(C_1-C_4)$alkyl and NH$_2$ when Z or Y is carbon.

11. The compound according to claim 1, wherein each $R^{10}$ is independently selected from the group consisting of hydrogen and $(C_1-C_4)$alkyl when Z or Y is carbon.

12. The compound according to claim 1, wherein each $R^{10}$ is independently selected from the group consisting of hydrogen and methyl when Z or Y is carbon.

13. The compound according to claim 1, wherein $R^{11}$ is selected from the group consisting of hydrogen, $(C_1-C_4)$alkyl, $(CO)NH_2$, and $(C_2-C_5)$heterocyclyl$(C_1-C_4)$alkyl.

14. The compound according to claim 1, wherein $R^{11}$ is selected from the group consisting of hydrogen and methyl.

15. The compound according to claim 1, wherein $R^9$ is selected from the group consisting of

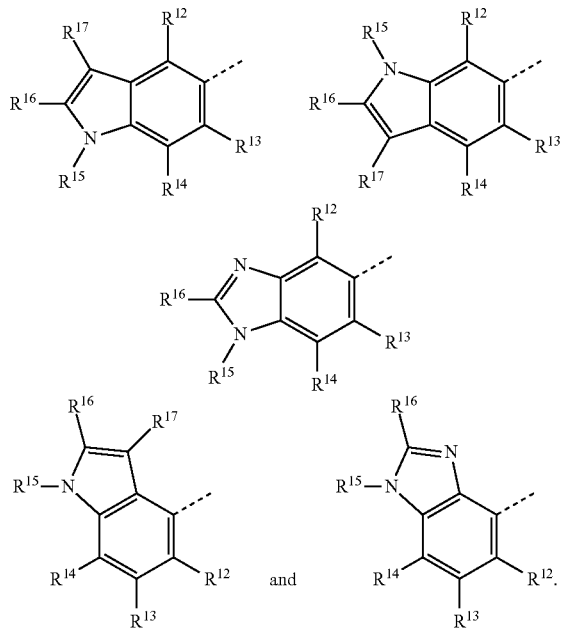

16. The compound according to claim 1, wherein $R^9$ is selected from the group consisting of

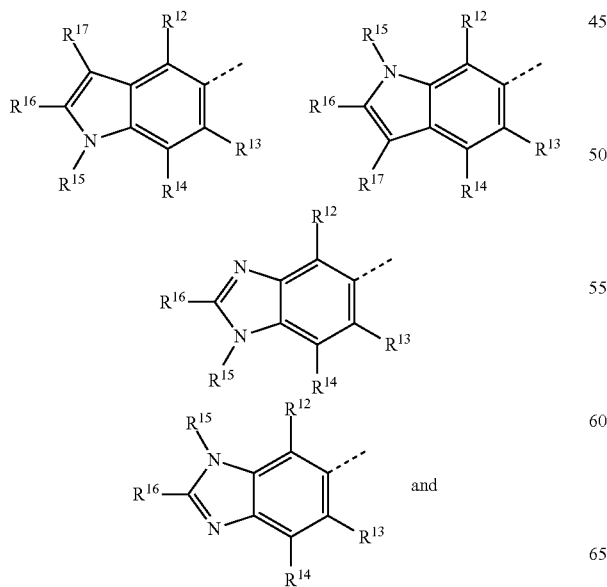

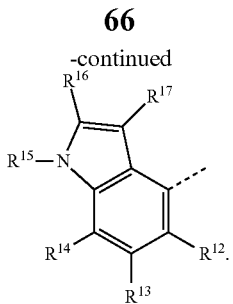

17. The compound according to claim 1, wherein $R^{12}$, $R^{13}$, and $R^{14}$ represent hydrogen.

18. The compound according to claim 1, wherein $R^{15}$ is selected from the group consisting of hydrogen and methyl.

19. The compound according to claim 1, wherein $R^{16}$ and $R^{17}$ are independently selected from the group consisting of hydrogen, $(C_1-C_4)$alkyl, $(C_1-C_4)$alkyl-OH, and $(CO)OH$.

20. The compound according to claim 19, wherein $R^{16}$ is an ester of $(CO)OH$, and is selected from the group consisting of $(CO)OCH_3$ and $(CO)OC_2H_5OH$.

21. The compound according to claim 1, wherein $R^{16}$ and $R^{17}$ are independently selected from the group consisting of hydrogen, methyl and $(C_1-C_4)$alkyl-OH.

22. The compound according to claim 1, wherein $R^{16}$ is selected from the group consisting of hydrogen, methyl, and $(C_1-C_4)$alkyl-OH.

23. The compound according to claim 1, wherein $R^{16}$ is selected from the group consisting of hydrogen, methyl and hydroxymethyl.

24. The compound according to claim 1, wherein $R^{17}$ is selected from the group consisting of hydrogen and methyl.

25. The compound according to claim 1, wherein Y represents carbon and Z represents nitrogen.

26. The compound according to claim 1, wherein
$R^4$ represents hydrogen;
$R^5$ is selected from the group consisting of halogen, methyl, $O(C_1-C_2)$alkyl, and $OCF_3$;
$R^6$ and $R^7$ are independently selected from the group consisting of hydrogen, methyl, and methoxy;
each $R^{10}$ is independently selected from the group consisting of hydrogen and methyl when Z or Y is carbon;
$R^{11}$ is selected from the group consisting of hydrogen, methyl, and $(CO)NH_2$;
$R^9$ is selected from the group consisting of

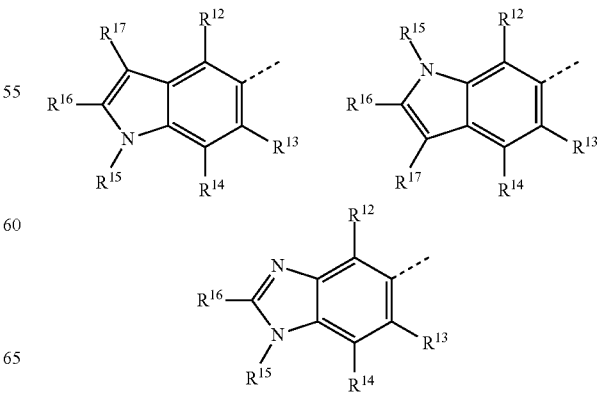

-continued

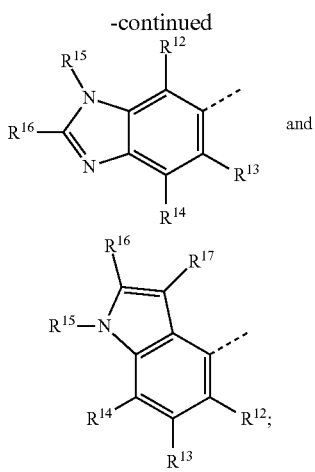
and

R[15] is selected from the group consisting of hydrogen and methyl; and

R[16] and R[17] are independently selected from the group consisting of hydrogen, methyl, and hydroxymethyl.

27. The compound according to claim 26, wherein R[16] represents methyl.

28. The compound according to claim 1, wherein

Z represents carbon and Y represents nitrogen;

R[1], R[2], R[3], R[8], R[12], R[13], and R[14] represent hydrogen;

R[4], R[5], R[6], and R[7] are independently selected from the group consisting of hydrogen, halogen, hydroxy, ($C_1$-$C_4$)alkyl, O($C_1$-$C_4$)alkyl, O($C_1$-$C_4$)alkyl($C_2$-$C_5$)heterocyclyl, and OCF$_3$;

each R[10] is independently selected from the group consisting of hydrogen and ($C_1$-$C_4$)alkyl when Z or Y is carbon;

R[11] is selected from the group consisting of hydrogen, ($C_1$-$C_4$)alkyl, (CO)NH$_2$, and ($C_2$-$C_5$)heterocyclyl($C_1$-$C_4$)alkyl;

R[9] is selected from the group consisting of

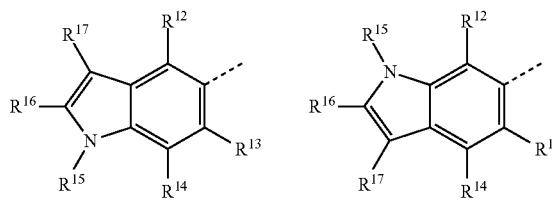

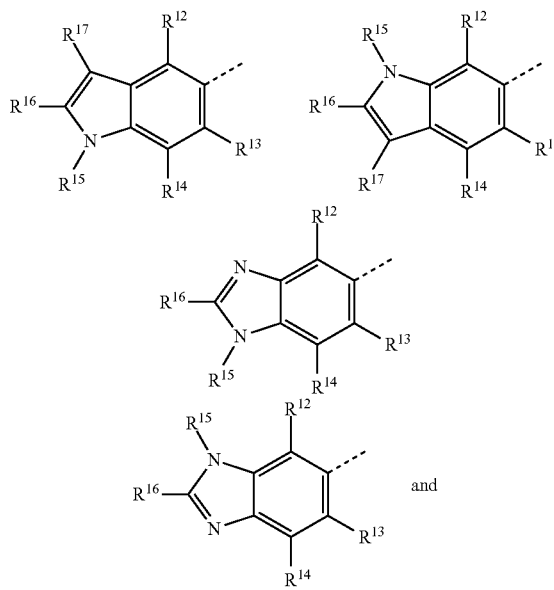

-continued

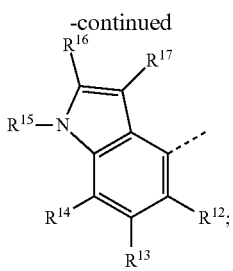

R[15] is selected from the group consisting of hydrogen and methyl;

and R[16] and R[17] are independently selected from the group consisting of hydrogen, ($C_1$-$C_4$)alkyl, ($C_1$-$C_4$)alkyl-OH, and (CO)OH.

29. The compound according to claim 28, wherein R[16] represents methyl.

30. The compound according to claim 26, wherein R[5] is selected from the group consisting of methoxy, methyl, and fluoro.

31. The compound according to claim 28, wherein R[11] is selected from the group consisting of hydrogen, methyl, and (CO)NH$_2$.

32. The compound according to claim 1, wherein

Z represents carbon and Y represents nitrogen;

R[1], R[10], R[12], R[13], R[14], and R[17] represent hydrogen;

R[2], R[3], R[7], R[8], and R[11] are independently selected from the group consisting of hydrogen and methyl;

R[4], R[5], and R[6] are independently selected from the group consisting of hydrogen, and O($C_1$-$C_4$)alkyl;

R[9] is selected from the group consisting of

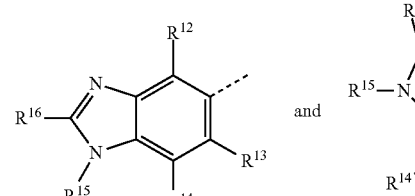

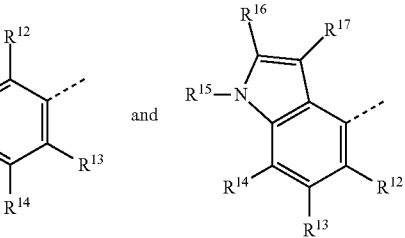

R[15] is selected from the group consisting of hydrogen and methyl; and

R[16] is selected from the group consisting of hydrogen, methyl, and hydroxymethyl.

33. The compound according to claim 1, wherein

Z represents carbon and Y represents nitrogen;

R[1], R[2], R[3], R[4], R[6], R[7], R[8], R[12], R[13], and R[14] represent hydrogen;

R[10], R[11], R[15], and R[17] are independently selected from the group consisting of hydrogen and methyl;

R[5] is selected from the group consisting of methoxy and ethoxy;

R⁹ is selected from the group consisting of

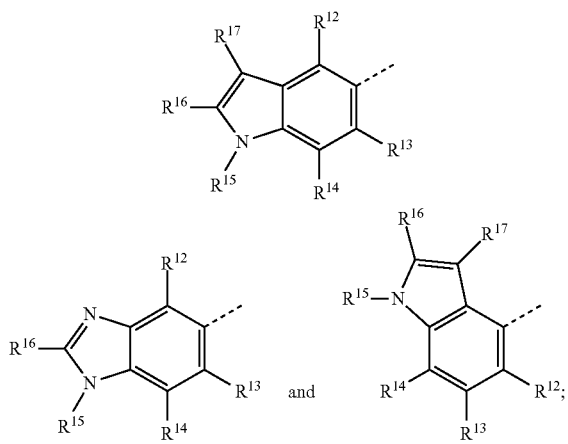

R¹⁶ is selected from the group consisting of hydrogen, methyl, and hydroxymethyl.

34. The compound according to claim 1, wherein
R¹, R², R³, R⁴, R⁶, R⁷, R⁸, R¹², R¹⁴, and R¹⁷ represent hydrogen;
each R¹⁰ is independently selected from the group consisting of hydrogen and amino;
R¹¹ is selected from the group consisting of hydrogen, (CO)NH₂, and (C₂-C₅)heterocyclyl(C₁-C₄)alkyl;
R⁵ is selected from the group consisting of methoxy, ethoxy, and hydroxy;
R¹⁵ is selected from the group consisting of hydrogen and methyl;
R¹⁶ is selected from the group consisting of hydrogen, methyl, and hydroxymethyl; and
R⁹ is selected from the group consisting of

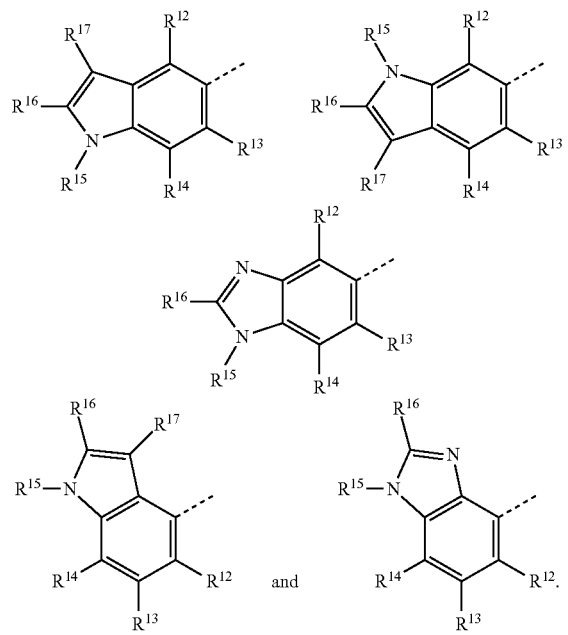

35. The compound according to claim 1, wherein
Z represents carbon or nitrogen;
Z represents carbon or nitrogen;
Y represents carbon or nitrogen, wherein one of Z and Y represents nitrogen;
R¹, R³, and R⁸ are independently selected from the group consisting of hydrogen and (C₁-C₄)alkyl;
R² is selected from the group consisting of hydrogen and (C₁-C₄)alkyl;
R⁴, R⁵, R⁶, and R⁷ are independently selected from the group consisting of hydrogen, halogen, hydroxy, (C₁-C₄)alkyl, and OCF₃, wherein one of R⁴, R⁵, R⁶, and R⁷ is not hydrogen;
each R¹⁰ is independently selected from the group consisting of hydrogen and amino, when Z or Y is carbon;
R¹¹ is selected from the group consisting of hydrogen, (C₁-C₄)alkyl(C₂-C₅)heterocyclyl, and (CO)NH₂;
R⁹ represents

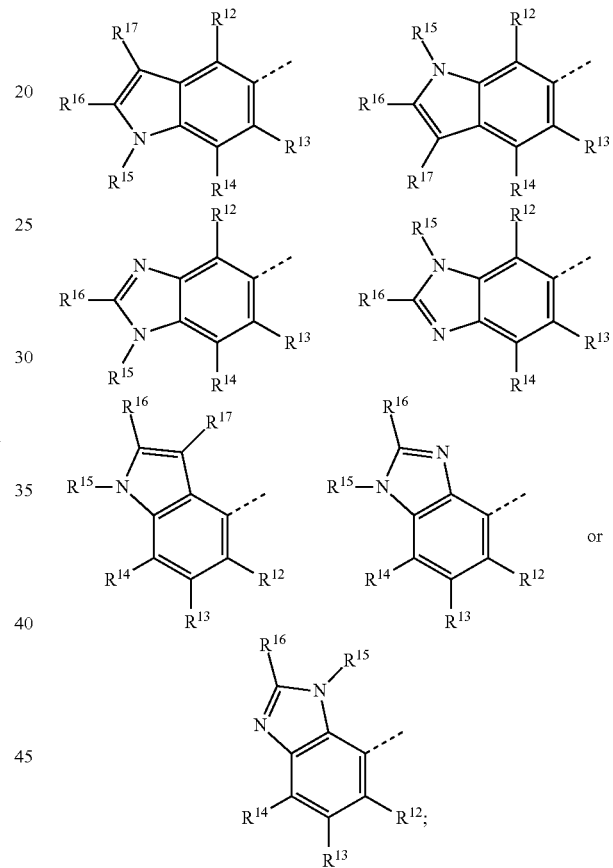

R¹², R¹³, and R¹⁴ are independently selected from the group consisting of hydrogen, halogen, hydroxy, (C₁-C₄)alkyl, O(C₁-C₄)alkyl, NH(C₁-C₄)alkyl, and N[(C₁-C₄)alkyl]₂;
R¹⁵ is selected from hydrogen and (C₁-C₄)alkyl; and
R¹⁶ and R¹⁷ are independently selected from the group consisting of hydrogen, halogen, (C₁-C₄)alkyl, (C₁-C₄)alkyl(C₂-C₅)heterocyclyl, (C₁-C₄)alkyl(C₂-C₅)heterocyclyl(C₁-C₄)alkyl, (C₁-C₄)alkyl(CO)OH, (C₁-C₄)alkyl(CO)NH₂, (C₁-C₄)alkyl(CO)NH(C₁-C₄)alkyl, (C₁-C₄)alkyl(CO)N[(C₁-C₄)alkyl]₂, (C₁-C₄)alkyl-OH, (C₁-C₄)alkyl-O(C₁-C₄)alkyl, (C₁-C₄)alkyl-NH(C₁-C₄)alkyl, (C₁-C₄)alkyl-N[(C₁-C₄)alkyl]₂, (C₁-C₄)alkyl-NH(CO)(C₁-C₄)alkyl, (CO)OH, (CO)NH₂, (CO)NH(C₁-C₄)alkyl, (CO)N[(C₁-C₄)alkyl]₂, (CO)(C₁-C₄)alkyl, (CO)(C₂-C₅)heterocyclyl, and (CO)(C₂-C₅)heterocyclyl(C₁-C₄)alkyl.

36. The compound according to claim 1, wherein

Z represents carbon or nitrogen;

Y represents carbon or nitrogen, wherein one of Z and Y represents nitrogen;

$R^1$, $R^2$, $R^3$ and $R^8$ are independently selected from the group consisting of hydrogen and $(C_1-C_4)$alkyl;

$R^4$, $R^5$, $R^6$ and $R^7$ are independently selected from the group consisting of hydrogen, halogen, hydroxy, $(C_1-C_4)$alkyl, $O(C_1-C_4)$alkyl, $O(C_1-C_4)$alkyl$(C_2-C_5)$heterocyclyl, and $OCF_3$;

$R^9$ represents

[structures]

each $R^{10}$ is independently selected from the group consisting of hydrogen, $(C_1-C_4)$alkyl and amino when Z or Y is carbon;

$R^{11}$ is selected from the group consisting of hydrogen, $(C_1-C_4)$alkyl, $(C_2-C_5)$heterocyclyl$(C_1-C_4)$alkyl and $(CO)NH_2$;

$R^{12}$, $R^{13}$ and $R^{14}$ are hydrogen;

$R^{15}$ and $R^{17}$ are independently selected from the group consisting of hydrogen and $(C_1-C_4)$alkyl; and $R^{16}$ is selected from the group consisting of hydrogen, $(C_1-C_4)$alkyl, $(CO)OH$, and $(C_1-C_4)$alkyl-OH.

37. The compound according to claim 1, wherein

Z represents carbon or nitrogen;

Y represents carbon or nitrogen, wherein one of Z and Y represents nitrogen;

$R^1$, $R^2$, $R^3$ and $R^8$ are independently selected from the group consisting of hydrogen and methyl;

$R^4$, $R^5$, $R^6$ and $R^7$ are independently selected from the group consisting of hydrogen, halogen, hydroxy, methyl, methoxy, ethoxy, propoxy, $O(C_1-C_4)$alkyl$(C_2-C_5)$heterocyclyl, and $OCF_3$;

$R^9$ represents

[structures]

each $R^{10}$ is independently selected from the group consisting of hydrogen, methyl and amino when Z or Y is carbon;

$R^{11}$ is selected from the group consisting of hydrogen, methyl, $(C_2-C_5)$heterocyclyl$(C_1-C_4)$alkyl and $(CO)NH_2$;

$R^{12}$, $R^{13}$ and $R^{14}$ are hydrogen;

$R^{15}$ and $R^{17}$ are independently selected from the group consisting of hydrogen and methyl; and $R^{16}$ is selected from the group consisting of hydrogen, methyl, $(CO)OH$, and $(C_1-C_4)$alkyl-OH.

38. The compound according to claim 1, said compound being selected from the group consisting of:

$N^2$-[2-(1H-indol-3-yl)ethyl]-$N^4$-(1H-indol-5-yl)pyrimidine-2,4-diamine;

$N^4$-(1H-indol-5-yl)-$N^2$-[2-(5-methoxy-1H-indol-3-yl)ethyl]pyrimidine-2,4-diamine;

$N^2$-[2-(1H-indol-3-yl)ethyl]-$N^4$-(2-methyl-1H-indol-5-yl)pyrimidine-2,4-diamine;

$N^2$-[2-(5-methoxy-1H-indol-3-yl)ethyl]-$N^4$-(2-methyl-1H-indol-5-yl)pyrimidine-2,4-diamine;

$N^2$-[2-(5-ethoxy-1H-indol-3-yl)ethyl]-$N^4$-(2-methyl-1H-indol-5-yl)pyrimidine-2,4-diamine;

$N^4$-(2-methyl-1H-indol-5-yl)-$N^2$-{2-[5-(2-morpholinoethoxy)-1H-indol-3-yl]ethyl}pyrimidine-2,4-diamine;

$N^4$-(2-methyl-1H-indol-5-yl)-$N^2$-{2-[5-(trifluoromethoxy)-1H-indol-3-yl]ethyl}pyrimidine-2,4-diamine;

3-{2-[4-(2-methyl-1H-indol-5-ylamino)pyrimidin-2-ylamino]ethyl}-1H-indol-5-ol;

$N^2$-[2-(5-methyl-1H-indol-3-yl)ethyl]-$N^4$-(2-methyl-1H-indol-5-yl)pyrimidine-2,4-diamine;

$N^2$-[2-(5-fluoro-1H-indol-3-yl)ethyl]-$N^4$-(2-methyl-1H-indol-5-yl)pyrimidine-2,4-diamine;

$N^2$-[2-(6-methoxy-1H-indol-3-yl)ethyl]-$N^4$-(2-methyl-1H-indol-5-yl)pyrimidine-2,4-diamine;

$N^2$-[2-(7-methoxy-1H-indol-3-yl)ethyl]-$N^4$-(2-methyl-1H-indol-5-yl)pyrimidine-2,4-diamine;

$N^4$-(1,2-dimethyl-1H-indol-5-yl)-$N^2$-[2-(5-methoxy-1H-indol-3-yl)ethyl]pyrimidine-2,4-diamine;
$N^4$-(2,3-dimethyl-1H-indol-5-yl)-$N^2$-[2-(5-methoxy-1H-indol-3-yl)ethyl]pyrimidine-2,4-diamine;
(5-{2-[2-(5-methoxy-1H-indol-3-yl)ethylamino]pyrimidin-4-ylamino}-1H-indol-2-yl)methanol;
methyl 5-{2-[2-(5-methoxy-1H-indol-3-yl)ethylamino]pyrimidin-4-ylamino}-1H-indole-2-carboxylate;
2-hydroxyethyl 5-{2-[2-(5-methoxy-1H-indol-3-yl)ethylamino]pyrimidin-4-ylamino}-1H-indole-2-carboxylate;
$N^4$-(1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzo[d]imidazol-5-yl)pyrimidine-2,4-diamine;
$N^4$-(1H-indol-6-yl)-$N^2$-[2-(5-methoxy-1H-indol-3-yl)ethyl]pyrimidine-2,4-diamine;
$N^4$-(1H-indol-4-yl)-$N^2$-[2-(5-methoxy-1H-indol-3-yl)ethyl]pyrimidine-2,4-diamine;
$N^4$-[2-(1H-indol-3-yl)ethyl]-$N^2$-(2-methyl-1H-indol-5-yl)pyrimidine-2,4-diamine;
$N^4$-[2-(5-methoxy-1H-indol-3-yl)ethyl]-$N^2$-(2-methyl-1H-indol-5-yl)pyrimidine-2,4-diamine;
$N^4$-[2-(1H-indol-3-yl)ethyl]-$N^2$-(1H-indol-6-yl)pyrimidine-2,4-diamine;
$N^4$-[2-(1H-indol-3-yl)ethyl]-$N^2$-(1H-indol-4-yl)pyrimidine-2,4-diamine;
$N^2$-[2-(1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-indol-5-yl)pyrimidine-2,4-diamine;
2-[2-(5-methoxy-1H-indol-3-yl)ethylamino]-6-(2-methyl-1H-indol-5-ylamino)pyrimidine-4-carboxamide;
$N^2$-[2-(5-methoxy-1H-indol-3-yl)ethyl]-5-methyl-$N^4$-(2-methyl-1H-indol-5-yl)pyrimidine-2,4-diamine; and
$N^2$-[2-(5-methoxy-1H-indol-3-yl)ethyl]-$N^4$-(2-methyl-1H-indol-5-yl)-6-(4-methylpiperazin-1-yl)pyrimidine-2,4-diamine;
or a pharmaceutically acceptable ester, solvate or salt thereof.

39. The compound according to claim 1, said compound being selected from the group consisting of:
$N^2$-[2-(4-methoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-[2-(5-propoxy-1H-indol-3-yl)ethyl]pyrimidine-2,4-diamine;
$N^2$-[2-(5-isopropoxy-1H-indol-3-yl)ethyl]-$N^4$-(2-methyl-1H-indol-5-yl)pyrimidine-2,4-diamine;
$N^2$-[2-(5,6-dimethoxy-1H-indol-3-yl)ethyl]-$N^4$-(2-methyl-1H-indol-5-yl)pyrimidine-2,4-diamine;
$N^2$-[2-(5-methoxy-7-methyl-1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(1-methyl-1H-benzo[d]imidazol-5-yl)pyrimidine-2,4-diamine;
$N^4$-(1,2-dimethyl-1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(1-methyl-1H-indol-4-yl)pyrimidine-2,4-diamine;
$N^2$-[2-(5-ethoxy-1H-indol-3-yl)ethyl]-6-methyl-$N^4$-(2-methyl-1H-indol-5-yl)pyrimidine-2,4-diamine;
$N^2$-[2-(5-methoxy-2-methyl-1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-benzo[d]imidazol-5-yl)pyrimidine-2,4-diamine;
$N^2$-[2-(5-ethoxy-1H-indol-3-yl)ethyl]-6-methyl-$N^4$-(2-methyl-1H-benzo[d]imidazol-5-yl)pyrimidine-2,4-diamine;
[5-(2-{[2-(5-methoxy-1H-indol-3-yl)ethyl][methyl]amino}pyrimidin-4-ylamino)-1H-indol-2-yl]methanol;
(5-{2-[2-(5-methoxy-1H-indol-3-yl)ethylamino]pyrimidin-4-ylamino}-1-methyl-1H-benzo[d]imidazol-2-yl)methanol;
$N^2$-[2-(5-methoxy-1H-indol-3-yl)ethyl]-$N^4$-methyl-$N^4$-(2-methyl-1H-indol-5-yl)pyrimidine-2,4-diamine; and
$N^4$-(1,2-dimethyl-1H-indol-5-yl)-$N^2$-[2-(5-methoxy-1H-indol-3-yl)ethyl]-$N^4$-methylpyrimidine-2,4-diamine;
or a pharmaceutically acceptable ester, solvate or salt thereof.

40. The compound according to claim 1, said compound being selected from the group consisting of:
[5-({2-[2-(5-ethoxy-1H-indol-3-yl)ethylamino]pyrimidin-4-yl}amino)-1H-indol-2-yl]methanol;
$N^2$-[2-(5-methoxy-1H-indol-3-yl)ethyl]-$N^4$-(2-methyl-1H-indol-6-yl)pyrimidine-2,4-diamine;
$N^2$-[2-(5-ethoxy-1H-indol-3-yl)ethyl]-$N^4$-(2-methyl-1H-indol-6-yl)pyrimidine-2,4-diamine;
$N^2$-[2-(5-methoxy-1H-indol-3-yl)ethyl]-$N^4$-(1-methylindol-6-yl)pyrimidine-2,4-diamine;
$N^2$-[2-(5-ethoxy-1H-indol-3-yl)ethyl]-$N^4$-(1-methylindol-6-yl)pyrimidine-2,4-diamine;
$N^2$-[2-(5-methoxy-1H-indol-3-yl)ethyl]-$N^4$-(2-methyl-1H-indol-4-yl)pyrimidine-2,4-diamine;
$N^2$-[2-(5-ethoxy-1H-indol-3-yl)ethyl]-$N^4$-(2-methyl-1H-indol-4-yl)pyrimidine-2,4-diamine;
3-[2-({4-[(1-methylindol-4-yl)amino]pyrimidin-2-yl}amino)ethyl]-1H-indol-5-ol;
$N^2$-[2-(5-ethoxy-1H-indol-3-yl)ethyl]-$N^4$-(1-methylindol-4-yl)pyrimidine-2,4-diamine;
$N^4$-(1,2-dimethylindol-4-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzimidazol-4-yl)pyrimidine-2,4-diamine;
$N^2$-[2-(5-ethoxy-1H-indol-3-yl)ethyl]-$N^4$-(2-methyl-1H-benzimidazol-4-yl)pyrimidine-2,4-diamine;
$N^4$-[2-(5-methoxy-1H-indol-3-yl)ethyl]-$N^2$-(1-methylindol-4-yl)pyrimidine-2,4-diamine;
2-[2-(5-ethoxy-1H-indol-3-yl)ethylamino]-6-[(2-methyl-1H-indol-5-yl)amino]pyrimidine-4-carboxamide;
6-[(1,2-dimethylbenzimidazol-5-yl)amino]-2-[2-(5-methoxy-1H-indol-3-yl)ethylamino]pyrimidine-4-carboxamide;
2-[2-(5-methoxy-1H-indol-3-yl)ethylamino]-6-[(1-methylindol-4-yl)amino]pyrimidine-4-carboxamide;
2-[2-(5-ethoxy-1H-indol-3-yl)ethylamino]-6-[(1-methylindol-4-yl)amino]pyrimidine-4-carboxamide;
$N^2$-[2-(5-methoxy-1H-indol-3-yl)ethyl]-$N^4$-(1-methylindol-4-yl)-6-(4-methylpiperazin-1-yl)pyrimidine-2,4-diamine; and
$N^2$-[2-(5-ethoxy-1H-indol-3-yl)ethyl]-$N^4$-(2-methyl-1H-indol-5-yl)pyrimidine-2,4,5-triamine;
or a pharmaceutically acceptable ester, solvate or salt thereof.

41. A method of treating a disease wherein inhibition of tubulin polymerization is beneficial, which comprises administering to a subject in need thereof, a therapeutically effective amount of a compound of formula I, according to claim 1, or a pharmaceutically acceptable ester, solvate or salt thereof.

42. A method of treating a disease wherein induction of apoptosis is beneficial, which comprises administering to a subject in need thereof, a therapeutically effective amount of a compound of formula I, according to claim 1, or a pharmaceutically acceptable ester, solvate or salt thereof.

43. A method of treating cancer, which comprises administering to a subject in need thereof, a therapeutically effective amount of a compound of formula I, according to claim 1, or a pharmaceutically acceptable ester, solvate or salt thereof.

44. The method according to claim 43, wherein said cancer is selected from the group consisting of leukemia, lymphoma, myeloma, breast cancer, ovarian cancer, prostate cancer, lung cancer, pancreatic cancer, and glioma.

45. A pharmaceutical composition comprising a compound according to claim 1, or a pharmaceutically acceptable ester, solvate or salt thereof, together with one or more of a pharmaceutically acceptable diluent and carrier.

* * * * *